(12) United States Patent
Choi et al.

(10) Patent No.: US 8,541,484 B2
(45) Date of Patent: Sep. 24, 2013

(54) PVA-PAA HYDROGELS

(75) Inventors: Jeeyoung Choi, Spartanburg, SC (US); Orhun K. Muratoglu, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 391 days.

(21) Appl. No.: 12/597,056

(22) PCT Filed: Apr. 24, 2008

(86) PCT No.: PCT/US2008/061388
§ 371 (c)(1),
(2), (4) Date: Dec. 9, 2009

(87) PCT Pub. No.: WO2008/131451
PCT Pub. Date: Oct. 30, 2008

(65) Prior Publication Data
US 2010/0105801 A1    Apr. 29, 2010

Related U.S. Application Data

(60) Provisional application No. 60/913,618, filed on Apr. 24, 2007, provisional application No. 60/969,831, filed on Sep. 4, 2007.

(51) Int. Cl.
*A61F 2/02*        (2006.01)
*B29C 35/16*       (2006.01)
*C08L 29/04*       (2006.01)
*C08F 16/06*       (2006.01)
*C08F 8/00*        (2006.01)

(52) U.S. Cl.
USPC ............. 523/115; 264/28; 424/425; 424/422; 424/423; 524/803; 525/56; 525/61

(58) Field of Classification Search
USPC .................... 523/115; 264/28; 424/425, 422, 424/423; 524/803; 525/56, 61
See application file for complete search history.

(56) References Cited

U.S. PATENT DOCUMENTS 4,663,358 A       5/1987   Hyon et al.
4,750,482 A  *    6/1988   Sieverding .................... 604/317

(Continued)

FOREIGN PATENT DOCUMENTS

JP      5-504689 A       7/1993
JP      2000-204165 A    7/2000

(Continued)

OTHER PUBLICATIONS

Jahan, et al., Combined Chemical and Mechanical Effects on Free Radicals in UHMWPE Joints During Implantation, Journal of Biomedical Materials Research, 1991, 25(8):1005-1017.

(Continued)

*Primary Examiner* — Michael Pepitone
(74) *Attorney, Agent, or Firm* — Quarles & Brady, LLP

(57) ABSTRACT

The invention provides fabricated PVA-hydrogels, PVA-hydrogel-containing compositions, and methods of making the same. The invention also provides methods of implanting or administering the PVA-hydrogels, or the PVA-hydrogel-containing compositions to treat a subject in need. Methods of cross-linking pre-solidified or pre-gelled hydrogel particles and making cross-linked PVA-hydrogels, and cross-linked PVA-hydrogel-containing compositions also are disclosed herein.

23 Claims, 30 Drawing Sheets

(56) References Cited

U.S. PATENT DOCUMENTS

| | | | |
|---|---|---|---|
| 4,920,158 | A | 4/1990 | Murray et al. |
| 5,522,898 | A | 6/1996 | Bao |
| 5,540,033 | A | 7/1996 | Fox et al. |
| 5,705,780 | A | 1/1998 | Bao |
| 5,846,214 | A * | 12/1998 | Makuuchi et al. .............. 602/52 |
| 5,879,400 | A | 3/1999 | Merrill et al. |
| 5,981,826 | A | 11/1999 | Ku et al. |
| 6,641,617 | B1 | 11/2003 | Merrill et al. |
| 6,852,772 | B2 | 2/2005 | Muratoglu et al. |
| 6,855,165 | B2 | 2/2005 | Fell et al. |
| 6,866,684 | B2 | 3/2005 | Fell et al. |
| 6,911,044 | B2 | 6/2005 | Fell et al. |
| 6,923,831 | B2 | 8/2005 | Fell et al. |
| 6,960,617 | B2 | 11/2005 | Omidian et al. |
| 2004/0092653 | A1 | 5/2004 | Ruberti et al. |
| 2004/0171740 | A1 | 9/2004 | Ruberti et al. |
| 2004/0220296 | A1 | 11/2004 | Lowman et al. |
| 2006/0079597 | A1 * | 4/2006 | Muratoglu et al. ........... 522/178 |

FOREIGN PATENT DOCUMENTS

| | | | |
|---|---|---|---|
| WO | WO9729793 | A1 | 8/1997 |
| WO | WO2006125082 | A2 | 11/2006 |
| WO | WO 2006132661 | A1 * | 12/2006 |
| WO | WO2006132661 | A1 | 12/2006 |

OTHER PUBLICATIONS

Kashiwabara, et al., Free Radicals and Crosslinking in Irradiated Polyethylene, Radiation Physics and Chemistry, 1991, 37(1):43-46.

Sutula, et al., The Otto Aufranc Award: Impact of Gamma Sterilization on Clinical Performance of Polyethylene in the Hip, Clinical Orthopaedics & Related Research, 1995, 319:28-40.

Tanaka, et al., Novel Hydrogels with Excellent Mechanical Performance, Progress in Polymer Science, 2005, 30 (1):1-9.

PCT International Search Report and Written Opinion, PCT/US2008/061388, Sep. 25, 2008.

PCT International Preliminary Report on Patentability, PCT/US2008/061388, Nov. 5, 2009.

European Patent Office, Extended European Search Report, Application No. 07784150.0, Jan. 13, 2010.

JPO English Language Machine Translation for JP 2000-204165, Apr. 2, 2013.

* cited by examiner

PVA-PAA HYDROGELS

This application is a 371 of International Application No. PCT/US2008/061388 filed Apr. 24, 2008, which claims priority to Provisional Application No. 60/913,618 filed Apr. 24, 2007 and Provisional Application No. 60/969,831 filed Sep. 4, 2007. The entire contents of the above-identified applications are hereby incorporated by reference.

FIELD OF THE INVENTION

The invention relates to manufacture of creep resistant and lubricious poly(vinyl alcohol)(PVA)-hydrogels, creep resistant and lubricious PVA-hydrogel-containing compositions, and methods of making fabricated PVA-hydrogels and PVA-hydrogel-containing compositions. The invention also relates to methods of using the fabricated creep resistant PVA-hydrogels and creep resistant PVA-hydrogel-containing compositions for osteochondral defect repair that require mechanical integrity, high water content, and excellent lubricity in order to fully function under the high stress environment in the joint space and withstand high loads of human joints.

BACKGROUND OF THE INVENTION

Biocompatible hydrogels as synthetic materials for osteochondral defect repair require mechanical integrity, high water content, and excellent lubricity to fully function under the high stress environment in the human joint spaces. PVA hydrogels are good candidates for such purposes, but currently available formulations do not provide enough mechanical strength and lubricity compatible to that of natural articular cartilage.

Most hydrogels systems available for articular cartilage replacement applications do not have required mechanical strength to withstand the high loads of the human joint. Various dehydration methods, described below, can be used together in combinations to alter the properties of hydrogels.

Solvent dehydration of hydrogels is described by Bao (U.S. Pat. No. 5,705,780). Bao describes immersion of PVA hydrogel into solvents such as ethanol/water mixture at room temperature to dehydrate PVA hydrogel without shape distortion.

Hyon and Ikada (U.S. Pat. No. 4,663,358) and Bao (U.S. Pat. No. 5,705,780) describe the use of water and organic solvent mixture to dissolve PVA powder and subsequently cooling the solution below room temperature and heating back up to room temperature to form a hydrogel. The hydrogel is then immersed in water to remove the organic solvent. Hyon and Ikada claim that PVA hydrogels thus formed are transparent, as opposed to the ones formed by freeze-thaw method that uses water only as the solvent to dissolve the PVA powder.

Bao (U.S. Pat. No. 5,522,898) describes dehydration methods that use air dehydration, vacuum dehydration, or partial humidity dehydration to control the rate of dehydration and prevent shape distortion of PVA hydrogels for use as prosthetic spinal devices to replace the nucleus pulposus. The starting gels of Bao are the freeze-thaw gels described in the U.S. Pat. No. 5,705,780.

Ku et al. (U.S. Pat. No. 5,981,826) describes a freeze-thaw method to form a PVA hydrogel by subjecting a PVA aqueous solution to freeze-thaw followed by immersion in water and additional cycles of freeze-thaw while immersed in water.

The creep resistance of PVA is currently achieved in the field by reducing the equilibrium water content (EWC) of the hydrogel, but which also reduces the lubricity of the hydrogel. Therefore, there remain long felt but an unmet need for, among other things, a creep resistant PVA-hydrogel, which also would retain the lubricity. Such a creep resistant PVA-hydrogel and methods of making such a composition was not known until the instant invention.

SUMMARY OF THE INVENTION

The present invention relates generally to creep resistant PVA-hydrogels, PVA-hydrogel-containing compositions, and methods of making PVA-hydrogels and PVA-hydrogel-containing compositions. The invention also relates to methods of using the creep resistant PVA-hydrogels and creep resistant PVA-hydrogel-containing compositions in treating a subject in need, for example, for osteochondral defect repair that require mechanical integrity, high water content, excellent lubricity to fully function under the high stress environment in the joint space and withstand high loads of human joints.

One aspect of the invention provides methods of making a PVA-hydrogel comprising: a) contacting an aqueous solution of poly(vinyl alcohol) (PVA) with an aqueous solution of poly(acrylic acid) (PAA) at a temperature above the room temperature, thereby forming a homogenous PVA-PAA solution; b) contacting the PVA-PAA solution with an aqueous solution of polyethylene glycol (PEG), thereby forming a homogenous PVA-PAA-PEG solution; and c) cooling the PVA-PAA-PEG solution to room temperature or below, thereby forming a PVA-hydrogel.

Another aspect of the invention provides methods of making a PVA-hydrogel comprising: a) contacting an aqueous solution of poly(vinyl alcohol) (PVA) with an aqueous solution of poly(acrylic acid) (PAA) at a temperature above the room temperature, thereby forming a homogenous PVA-PAA solution; b) pouring the PVA-PAA solution onto a mold (optionally pre-heated) followed by cooling down to room temperature, thereby allowing formation of the PVA-hydrogel; c) cooling the PVA-hydrogel by freezing at a temperature below 0° C.; d) thawing the PVA-hydrogel to a temperature above 0° C.; and e) immersing PVA-hydrogel in a PEG solution, thereby allowing diffusion of the PEG into the PVA-hydrogel.

Another aspect of the invention provides methods of making a PVA-hydrogel comprising: a) contacting an aqueous solution of poly(vinyl alcohol) (PVA) with an aqueous solution of poly(acrylic acid) (PAA) at a temperature above the room temperature, thereby forming a homogenous PVA-PAA solution; b) contacting the PVA-PAA solution with an aqueous solution of polyethylene glycol (PEG), thereby forming a homogenous PVA-PAA-PEG solution; c) pouring the PVA-PAA-PEG solution onto a mold (optionally pre-heated) followed by cooling down to room temperature, thereby allowing formation of the PVA-hydrogel; d) cooling the PVA-hydrogel by freezing at a temperature below 0° C.; and e) thawing the PVA-hydrogel to a temperature above 0° C.

According to one aspect of the invention, the mold is pre-heated to a temperature between about 1 and about 200° C., preferably between about 25° C. and about 150° C., more preferably about 90° C.

According to another aspect, the invention provides methods as described above, wherein the hydrogel comprises PVA-hydrogel, wherein the hydrogel comprises water and/or one or more other ingredients. The ingredients are PAA, PEG, and/or salt, proteoglycan, water soluble polymer, amino acid, alcohol, DMSO, water soluble vitamin, wherein in the ingredients are partially or completely soluble in water.

According to another aspect, the ingredients are PAA, and/or salt, proteoglycan, water soluble polymer, amino acid, alcohol, DMSO, water soluble vitamin, wherein in the ingredients are partially or completely soluble in water.

According to another aspect, the ingredients are PEG, wherein the PEG is in a solution of water, ethanol, ethylene glycol, DMSO, or another suitable solvent.

According to another aspect, the ingredients are non-volatile.

According to another aspect, the ingredients are at least partially miscible in water.

According to another aspect, the ingredients are selected from the group consisting of PEG, salt, NaCl, KCl, $CaCl_2$, vitamins, carboxylic acids, hydrocarbons, esters, and amino acids, PEG of different molecular weights or a blend of PEGs of different molecular weights, or any combination of the above.

According to another aspect, the water miscible polymer is PEO, Pluronic, amino acids, proteoglycans, polyvinylpyrrolidone, polysaccharides, dermatin sulfate, keratin sulfate, chondroitin sulfate, or dextran sulfate, or any combination of the above.

According to another aspect, at least 0.1% of the hydrogel's weight constitutes one or more non-volatile ingredient.

According to another aspect, the dehydration is carried out by placing the hydrogel in: a) a non-solvent, wherein i) the non-solvent is PEG, alcohols, acetones, saturated salinated water, vitamin, or carboxylic acid, aqueous solution of a salt of an alkali metal, or a combination thereof, and ii) the non-solvent contains more than one ingredients including water, PEG, vitamin, polymer, ester, proteoglycan, and carboxylic acid, or b) in a supercritical fluid.

According to another aspect, the dehydration is carried out by leaving the hydrogel in air, by placing the hydrogel in a vacuum at room temperature or at an elevated temperature, for example, at 40° C., above about 40° C., about 80° C., above 80° C., about 90° C., about 100° C., above 100° C., about 150° C., about 160° C., above 160° C., about 180° C., about 200° C., or above 200° C.

According to another aspect, the dehydration is carried out by heating the hydrogel in air or inert atmosphere (in presence of inert gas, such as nitrogen, argon, neon, or helium), or under vacuum at an elevated temperature, wherein the heating rate is slow or fast or the heating follows the vacuum or air dehydration.

According to another aspect, the dehydration is carried out in an atmosphere containing 100% air, 100% inert gas, a mixture of one or more inert gases containing 0.1% to 99.9% air, or a mixture of one or more inert gases mixed with 0.1% to 99.9% oxygen.

According to another aspect, the dehydrated hydrogel is re-hydrated by placing the dehydrated hydrogel: i) in water, saline solution, Ringer's solution, salinated water, buffer solution, and the like, or a combination thereof, ii) in a humid chamber, or iii) at room temperature or at an elevated temperature.

According to another aspect, the PVA-hydrogels made by above disclosed methods are re-hydrated to reach an equilibrium, wherein the PVA-hydrogels are re-hydrated in water or a salt solution.

In one aspect, the invention provides PVA-hydrogels comprising a polymer and water, wherein the PVA-hydrogels contain at least about 1% to about 50% equilibrium water content.

In another aspect, the invention provides PVA-hydrogels made by any of the above described processes, wherein the PVA-hydrogel is capable of re-hydration following dehydration, wherein the dehydration reduces the weight of the hydrogel; and the re-hydration results in increase in equilibrium water content in the re-hydrated hydrogel.

In another aspect, the PVA-hydrogels are of a biaxial orientation or of a uniaxial orientation, wherein the PVA-hydrogel has a high ultimate tensile strength.

Yet another aspect of the invention provides medical implants comprising a PVA-PAA-hydrogel, for example, an interpositional device, wherein the interpositional device a unispacer, wherein the unispacer is a free floating articular implant in human joints such as a knee, a hip, a shoulder, an elbow, or an upper or an extremity joint.

Yet another aspect of the invention provides medical implants comprising a PVA-PAA-PEG-hydrogel, for example, an interpositional device, wherein the interpositional device a unispacer, wherein the unispacer is a free floating articular implant in human joints such as a knee, a hip, a shoulder, an elbow, or an upper or an extremity joint.

According to another aspect, the invention provides PVA-hydrogels made by any of the above described processes, wherein pH-induced phase-separation of PVA-PAA solutions into the PVA-rich and PAA-rich domains prior to gelation increases creep resistance of PAA-containing PVA hydrogels.

According to another aspect, the invention provides PVA-hydrogels made by any of the above described processes, wherein certain pH value (which is the "miscibility transition inducing" pH ($pH_{mt}$)) varies depending on factors selected from the group consisting of the total polymer concentration, molecular weight of each polymer, PVA:PAA ratio, salt concentration or the ionic strength of the solution, and the like.

According to another aspect, the invention provides PVA-hydrogels made by any of the above described processes, wherein miscibility of PVA-PAA solutions prior to gelation is controlled by adjusting pH values of the PVA-PAA solutions below or above $pH_{mt}$.

According to another aspect, the invention provides PVA-hydrogels made by any of the above described processes, wherein the certain pH value (which is the "miscibility transition inducing" pH ($pH_{mt}$)) of a PVA-PAA solution containing 1.654 w/w % aqueous PAA solution and 25% total polymer having a PVA:PAA ratio of 19:1 is between about 3.0 and about 5.5.

According to another aspect, the invention provides PVA-hydrogels made by any of the above described processes, wherein the certain pH value (which is the "miscibility transition inducing" pH ($pH_{mt}$)) of a PVA-PAA solution containing 0.332 w/w % aqueous PAA solution and 25% total polymer having a PVA:PAA ratio of 99:1 is between about 1.5 and about 5.5.

Unless otherwise defined, all technical and scientific terms used herein in their various grammatical forms have the same meaning as commonly understood by one of ordinary skill in the art to which this invention belongs. Although methods and materials similar to those described herein can be used in the practice or testing of the present invention, the preferred methods and materials are described below. In case of conflict, the present specification, including definitions, will control. In addition, the materials, methods, and examples are illustrative only and are not limiting.

Further features, objects, advantages, and aspects of the present invention are apparent in the claims and the detailed description that follows. It should be understood, however, that the detailed description and the specific examples, while indicating preferred aspects of the invention, are given by way of illustration only, since various changes and modifications within the spirit and scope of the invention will become apparent to those skilled in the art from this detailed description.

C. in air (without argon gas purging), (C) 16 hour heating at 160° C. under argon gas, and (D) 1 hour heating at 200° C. under argon gas.

Figure 26:
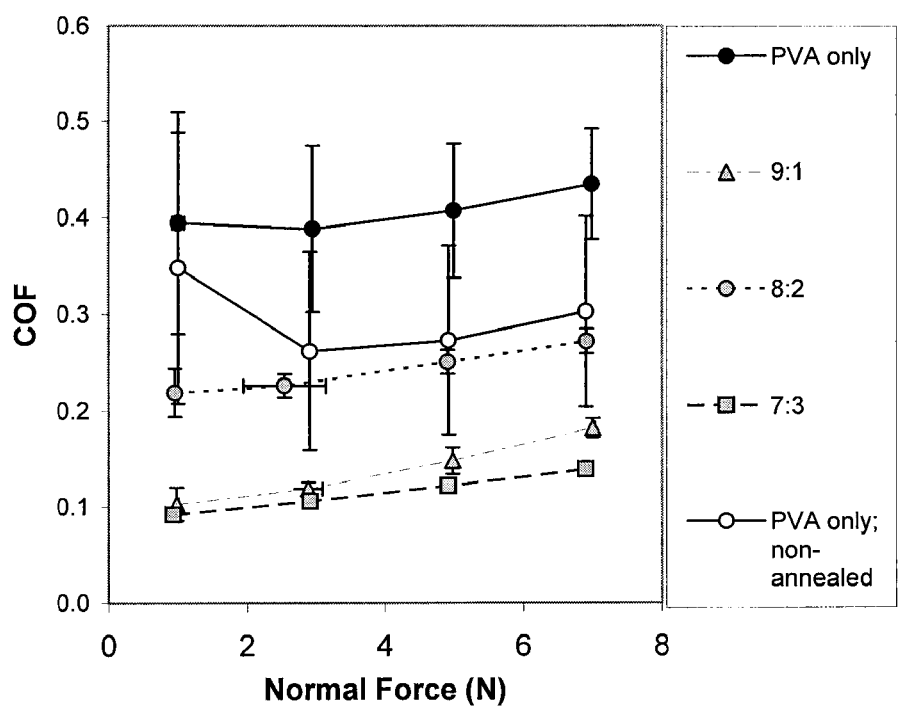

FIG. 26 shows the coefficient of friction (COF) of the PAA-containing PVA gels with various PVA:PAA ratio made by type 1 gel method. All gels were annealed for 1 hour at 160° C. under argon gas except for "PVA only; Non-annealed", which indicates the non-annealed hydrogels made with only PVA without PAA. "PVA only" indicates the annealed PVA gels made with only PVA without PAA. (A) PVA only, (B) 9:1 PVA:PAA, (C) 8:2 PVA;PAA, (D) 7:3 PVA:PAA, (E) PVA only; non-annealed.

Figure 27:
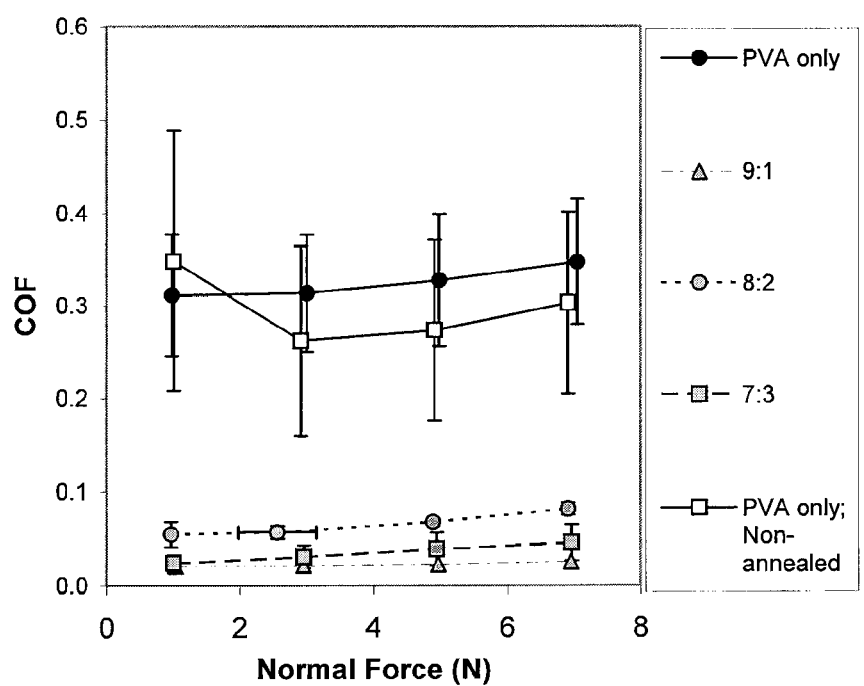

FIG. 27 shows the coefficient of friction (COF) of the PAA-containing PVA gels with various PVA:PAA ratio made by type 1 gel method. All gels were annealed for 1 hour at 160° C. under air except for "PVA only; Non-annealed", which indicates the non-annealed hydrogels made with only PVA without PAA. "PVA only" indicates the annealed PVA gels made with only PVA without PAA. (A) PVA only, (B) 9:1 PVA:PAA, (C) 8:2 PVA;PAA, (D) 7:3 PVA:PAA, (E) PVA only; non-annealed.

Figure 28:
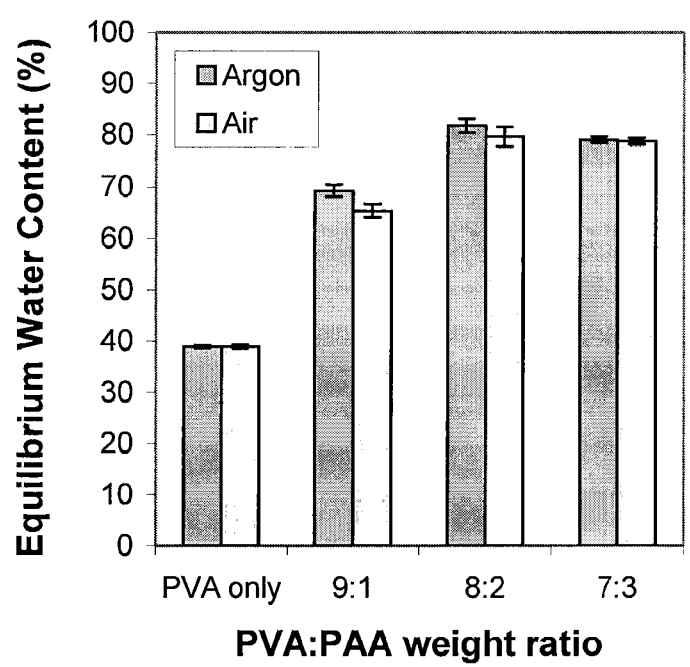

FIG. 28 shows the equilibrium water content (EWC) of the PAA-containing PVA gels with various PVA:PAA ratio made by type 1 gel method followed by annealing for 1 hour at 160° C. under argon gas or in air. "PVA only" indicates the annealed PVA gels made with only PVA without PAA. (A) PVA only, (B) 9:1 PVA:PAA, (C) 8:2 PVA;PAA, (D) 7:3 PVA:PAA.

Figure 29:
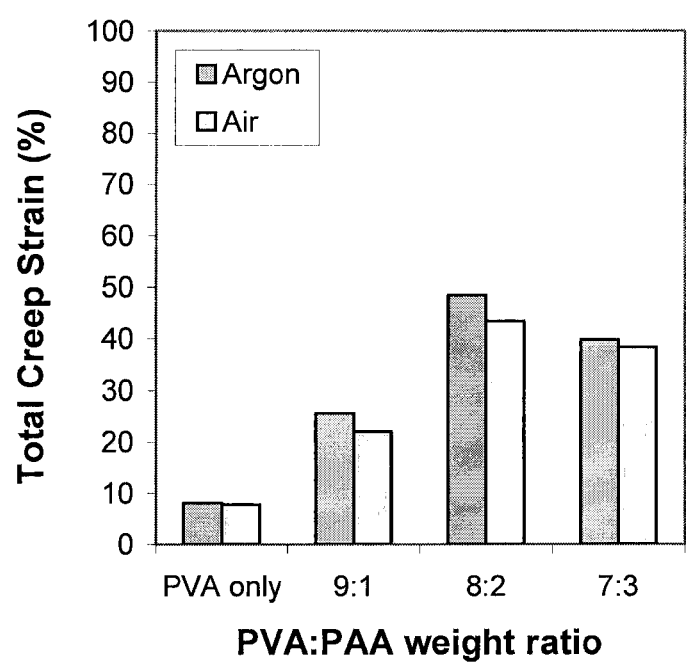

FIG. 29 shows the total creep strain (TCS) of the PAA-containing PVA gels with various PVA:PAA ratio made by type 1 gel method followed by annealing for 1 hour at 160° C. under argon gas or in air. "PVA only" indicates the annealed PVA gels made with only PVA without PAA. (A) PVA only, (B) 9:1 PVA:PAA, (C) 8:2 PVA;PAA, (D) 7:3 PVA:PAA.

DETAILED DESCRIPTION OF THE INVENTION

The present invention provides creep resistant PVA-hydrogels, which also retain lubricity, and methods of making creep resistant PVA-hydrogel for osteochondral defect repair, which possesses one or more of mechanical integrity, high water content, excellent lubricity to fully function under the high stress environment in the joint space and the ability to withstand high loads of human joints.

According to one embodiment of the invention, a second polymer is incorporated by physically blending with PVA and/or chemically tethering the molecules of the second polymer to PVA molecules in the hydrogel. The second polymer also can be polymerized in the presence of PVA molecules. A number of post-processing methods such as freeze-thaw, vacuum dehydration, solvent dehydration, heating, also can be used.

Increased hydrophilicity achieved by the addition of this second polymer results in increased water uptake, which improves surface lubricity of the PVA hydrogels. In cases where the second polymer has high ionic strength, electrostatic repulsion provides increased elasticity under compressive or tensile loading, similar to cartilage. The second polymer also can have chemical functional groups that can cross-link with each other or with the PVA molecules to form an interpenetrating network to reinforce the original PVA network structure. Polymers with weak acid or weak base functional groups also can be used to impart pH-sensitivity to the originally non-ionic PVA hydrogels. This is useful for pH-induced volume transition and complexation with dyes, drugs, and/or biological molecules.

In another embodiment, the invention provides methods of designing such systems. With PVA-hydrogels as a base hydrogel system, the newly incorporated hydrophilic entities are macromolecules with ionic chemical functionality or hydrogen bonding capability, namely, poly(acrylic acid) (PAA) and poly(allylamine hydrochloride) (PAH), PVA-PAA copolymer, poly(ethylene oxide) (PEO)-PAA copolymer, Poly(methacrylic acid) (PMAA), hyaluronic acid (HA), and polyvinylpyrrolidone (PVP). Methods for incorporating the new hydrophilic moieties include blends with PVA before gel formation and diffusion into PVA after gel formation. Methods for stabilizing the introduced new moieties inside the original gel network include, chemical cross-linking, irradiation, dehydration, and thermal treatment and combinations thereof. The incorporation of the second polymer in PVA can be non-uniform to impart, for example, non-uniform gradient properties to the final implant, such as different water content, creep strength, mechanical properties, and cross-link density, and the like.

Methods of Making PVA-PAA-PEG Gels:

1. Blending of PVA and PAA in Solution with PEG Addition.

In one embodiment, aqueous poly(acrylic acid) (PAA) solution is mixed with an aqueous solution of poly(vinyl alcohol) (PVA) at an elevated temperature above room temperature to form a homogenous PVA-PAA solution. PVA:PAA ratio can be about 99.9:0.1 to 5:5, for example, 99.5:0.5, 99:1, 79:1, 59:1, 39:1, 19:1, 9:1, 8:2, 7:3, 6:4, 5:5, or any ratio thereabout, or therebetween, with the total polymer content in the mixture at about 10%, 15%, 20%, 25%, 27%, 30%, 35%, 40%, 45%, 50%, or any value thereabout, therebetween, or higher. Polyethylene glycol (PEG) is added to the PVA-PAA hot (for example, about 90° C.) mixture to form a homogenous PVA-PAA-PEG solution and poured into a mold (optionally pre-heated) followed by cooling down to a lower temperature to form a gel.

2. Freeze-Thawing of PVA-PAA-PEG Gels.

In another embodiment, aqueous poly(acrylic acid) (PAA) solution is mixed into an aqueous solution of poly(vinyl alcohol) (PVA) at an elevated temperature above room temperature to form a homogenous PVA-PAA solution. PVA:PAA ratio can be about 99.9:0.1 to 5:5, for example, 99.5:0.5, 99:1, 79:1, 59:1, 39:1, 19:1, 9:1, 8:2, 7:3, 6:4, 5:5, or any ratio thereabout, or therebetween, with the total polymer content in the mixture at about 15%, 20%, 25%, 27%, 30%, 35%, 40%, 45%, any value thereabout, therebetween, or higher. Polyethylene glycol (PEG) is added to the PVA-PAA hot (for example, about 90° C.) mixture to form a homogenous PVA-PAA-PEG solution and poured into a mold (optionally pre-heated) followed by freezing at a temperature below 0° C. followed by thawing above 0° C. In some embodiments the freeze thaw cycles are repeated.

3. Freeze-Thawing of PVA-PAA Gels with PEG-Doping.

In another embodiment, aqueous poly(acrylic acid) (PAA) solution is mixed into an aqueous solution of poly(vinyl alcohol) (PVA) at an elevated temperature above room temperature to form a homogenous PVA-PAA solution. PVA:PAA ratio can be about 99.9:0.1 to 5:5, for example, 99.5:0.5, 99:1, 79:1, 59:1, 39:1, 19:1, 9:1, 8:2, 7:3, 6:4, 5:5, or any ratio thereabout, or therebetween, with the total polymer content in the mixture at about 10%, 15%, 20%, 25%, 27%, 30%, 35%, 40%, 45%, 50%, or any value thereabout, therebetween, or higher. The mixture is poured into a mold (optionally pre-heated) followed by freezing at a temperature below 0° C., followed by thawing above 0° C. The PVA-PAA gel is immersed in PEG to diffuse PEG into the gel. The gel either used in this form after re-hydration in water or saline, or it is subjected to further processing such as heating.

4. Diffusion of PEG into PVA-PAA Gels.

In another embodiment, aqueous polyacrylic acid (PAA) solution is mixed into an aqueous solution of poly(vinyl alcohol) (PVA) at an elevated temperature above room temperature to form a homogenous PVA-PAA solution. PVA:PAA ratio can be about 99.9:0.1 to 5:5, for example, 99.5:0.5, 99:1, 79:1, 59:1, 39:1, 19:1, 9:1, 8:2, 7:3, 6:4, 5:5, or any ratio thereabout, or therebetween, with the total polymer content in the mixture at about 10%, 15%, 20%, 25%, 27%, 30%, 35%, 40%, 45%, 50%, or any value thereabout, therebetween, or higher. The mixture is poured into a mold (optionally pre-heated) followed by freezing at a temperature below 0° C. followed by thawing above 0° C. The PVA-hydrogel is immersed in PEG to diffuse PEG into the gel while extracting some or all of the water.

5. Freeze-Thawing of PVA Gels Followed by Diffusion of PAA into PVA Gels.

In another embodiment, an aqueous poly(vinyl alcohol) (PVA) solution at an elevated temperature above room temperature is poured into a mold (optionally pre-heated) and cooled down below 0° C., followed by thawing at a temperature above 0° C. to form a PVA cryogel. The total PVA content in the gel can be about 10%, 15%, 20%, 25%, 27%, 30%, 35%, 40%, 45%, or any value thereabout, therebetween, or higher. The PVA cryogel is immersed in an aqueous solution of PAA to diffuse PAA into the gel. Vigorous agitation and/or elevated temperature is used to increase the diffusion rate. The diffusion rate also can be increased by immersing the gel in a supercritical fluid.

6. PAA Incorporated PVA Cyrogel Followed by PEG-Doping.

In another embodiment, an aqueous poly(vinyl alcohol) (PVA) solution at an elevated temperature above room temperature is poured into a mold (optionally pre-heated) and cooled down below 0° C., followed by thawing at a temperature above 0° C. to form a PVA cryogel. The total PVA content in the gel can be about 10%, 15%, 20%, 25%, 27%, 30%, 35%, 40%, 45%, or any value thereabout, therebetween, or higher. The PVA cryogel is immersed in an aqueous solution of PAA to diffuse PAA into the gel. Vigorous agitation and/or elevated temperature is used to increase the diffusion rate. The diffusion rate also can be increased by immersing the gel in a supercritical fluid. The gel then can be immersed in PEG to diffuse PEG into the gel while extracting some or all of the water out.

The hydrophilic entity incorporated in the PVA gels by any of the methods described above is not limited to PAA homopolymer, but can be other types of hydrophilic polymers with chemical functionality, namely, PVA-PAA copolymer, poly(ethylene oxide) (PEO)-PAA copolymer, Poly(methacrylic acid) (PMAA), polyvinylpyrrolidone (PVP), hyaluronic acid (HA), and poly(allylamine hydrochloride) (PAH). The freeze-thaw methods described in the above gels do not need to be limited to 1 cycle of freeze/thaw but can be more than one cycle, for example, 2, 3, 4, 5, 8, 10 or more cycles. In any of the above embodiments the final gel device can be dehydrated in a solvent or under vacuum and/or subsequently heated prior to final re-hydration in water or physiologic saline solution.

According to one embodiment, the mold in any of the above methods, is pre-heated to a temperature between about 1 and about 200° C., preferably between about 25° C. and about 150° C., more preferably about 90° C.

7. Mixing PVA Solutions with Other Ingredients.

Mixing can be done in various ways, for example,
  a) PVA solutions can be blended by mixing/stirring with other ingredients, as described herein, in a container, such as a beaker; and
  b) PVA solutions can be blended with other ingredients, as described herein, using a compounder.

In another embodiment, aqueous poly(acrylic acid) (PAA) solution is mixed with an aqueous solution of poly(vinyl alcohol) (PVA) at an elevated temperature above room temperature to form a homogenous PVA-PAA solution by blending in a container or by using a compounder along with other ingredients. According to one aspect of the invention, the hydrogel comprises water and/or one or more other ingredients, such as PAA, PEG (PEG is in a solution of water, ethanol, ethylene glycol, DMSO, or another suitable solvent), PEG of different molecular weights or a blend of PEGs of different molecular weights, salt, NaCl, KCl, $CaCl_2$, vitamins, carboxylic acids, hydrocarbons, esters, amino acids, proteoglycan, water soluble polymers, alcohol, wherein in the other ingredients are at least partially miscible or soluble in water.

The ingredients for mixing can be of any forms, such as powder, pellets, liquid, wax, paste, micro or nano-particles, or already gelled substances. Already gelled substances can be previously processed by post-gelling methods such as dehydration, rehydration, solvent-immersion, heat treatment, irradiation, and/or freeze-thawing.

Gelation:

According to some embodiments, gelation can be done by cooling down in presence of a gellant such as PEG; and/or freeze-thaw (for one or more cycles); and/or irradiation.

According to one aspect of the invention, irradiation of the solution is done to cause gelation. During irradiation, the solvent in the gel solution can be in any medium such as water, DI-water, saline, DMSO, ethanol, PEG, another suitable solvents, and any mixture of any of the above.

Irradiation:

According to another aspect, irradiation can be done on already gelled substances by mixing with gellants, or freeze-thawing. Gelled substances can be immersed in a medium such as water, DI-water, saline, DMSO, ethanol, PEG, and any suitable solvents, and any mixture of any of the above prior to or during irradiation. Gelled substances can be placed in an atmosphere containing air, inert gas, or vacuum for dehydration and further treated with annealing after irradiation.

According to another aspect, gelled substances can be dehydrated in air or in vacuum, after soaking in a medium such as water, DI-water, saline, DMSO, ethanol, PEG, and any suitable solvents, and any mixture of any of the above, then irradiated. Irradiated substances can be further dehydrated in air or in a vacuum at room temperature or at an elevated temperature.

According to another aspect, gelled substances can be dehydrated, and/or thermally annealed before irradiation.

According to another aspect, irradiation can be of any type, such as MIR, CISM, CIMA, WIAM, and the like, and sequential with any of the steps with annealing in between.

Methods and Sequence of Irradiation:

The selective, controlled manipulation of polymers and polymer alloys using radiation chemistry can, in another aspect, be achieved by the selection of the method by which the polymer is irradiated. The particular method of irradiation employed, either alone or in combination with other aspects of the invention, such as the polymer or polymer alloy chosen, contribute to the overall properties of the irradiated polymer.

Gamma irradiation or electron radiation may be used. In general, gamma irradiation results in a higher radiation penetration depth than electron irradiation. Gamma irradiation, however, generally provides low radiation dose rate and requires a longer duration of time, which can result in more in-depth and extensive oxidation, particularly if the gamma irradiation is carried out in air. Oxidation can be reduced or prevented by carrying out the gamma irradiation in an inert gas, such as nitrogen, argon, neon, or helium, or under vacuum. Electron irradiation, in general, results in more limited dose penetration depth, but requires less time and, therefore, reduces the risk of extensive oxidation if the irradiation is carried out in air. In addition if the desired dose levels are high, for instance 20 Mrad, the irradiation with gamma may take place over one day, leading to impractical production times. On the other hand, the dose rate of the electron beam can be adjusted by varying the irradiation parameters, such as conveyor speed, scan width, and/or beam power. With the appropriate parameters, a 20 Mrad melt-irradiation can be completed in for instance less than 10 minutes. The penetration of the electron beam depends on the beam energy measured by million electron-volts (MeV). Most polymers exhibit a density of about 1 g/cm$^3$, which leads to the penetration of about 1 cm with a beam energy of 2-3 MeV and about 4 cm with a beam energy of 10 MeV. If electron irradiation is preferred, the desired depth of penetration can be adjusted based on the beam energy. Accordingly, gamma irradiation or electron irradiation may be used based upon the depth of penetration preferred, time limitations and tolerable oxidation levels.

According to certain embodiments, the cross-linked polymeric material can have a melt history, meaning that the polymeric material is melted concurrently with or subsequent to irradiation for cross-linking. According to other embodiments, the cross-linked polymeric material has no such melt history.

Various irradiation methods including IMS, CIR, CISM, WIR, and WIAM are defined and described in greater detail below for cross-linked polymeric materials with a melt history, that is irradiated with concurrent or subsequent melting:

(i) Irradiation in the Molten State (IMS):

Melt-irradiation (MIR), or irradiation in the molten state ("IMS"), is described in detail in U.S. Pat. No. 5,879,400. In the IMS process, the polymer to be irradiated is heated to at or above its melting point. Then, the polymer is irradiated. Following irradiation, the polymer is cooled.

Prior to irradiation, the polymer is heated to at or above its melting temperature and maintained at this temperature for a time sufficient to allow the polymer chains to achieve an entangled state. A sufficient time period may range, for example, from about 5 minutes to about 3 hours.

Gamma irradiation or electron radiation may be used. In general, gamma irradiation results in a higher radiation penetration depth than electron irradiation. Gamma irradiation, however, generally provides low radiation dose rate and requires a longer duration of time, which can result in more in-depth oxidation, particularly if the gamma irradiation is carried out in air. Oxidation can be reduced or prevented by carrying out the gamma irradiation in an inert gas, such as nitrogen, argon, neon, or helium, or under vacuum. Electron irradiation, in general, results in more limited dose penetration depth, but requires less time and, therefore, reduces the risk of extensive oxidation if the irradiation is carried out in air. In addition if the desired dose levels are high, for instance 20 Mrad, the irradiation with gamma may take place over one day, leading to impractical production times. On the other hand, the dose rate of the electron beam can be adjusted by varying the irradiation parameters, such as conveyor speed, scan width, and/or beam power. With the appropriate parameters, a 20 Mrad melt-irradiation can be completed in for instance in less than 10 minutes. The penetration of the electron beam depends on the beam energy measured by million electron-volts (MeV). Most polymers exhibit a density of about 1 g/cm$^3$, which leads to the penetration of about 1 cm with a beam energy of 2-3 MeV and about 4 cm with a beam energy of 10 MeV. The penetration of e-beam is known to increase slightly with increased irradiation temperatures. If electron irradiation is preferred, the desired depth of penetration can be adjusted based on the beam energy. Accordingly, gamma irradiation or electron irradiation may be used based upon the depth of penetration preferred, time limitations and tolerable oxidation levels.

The temperature of melt-irradiation for a given polymer depends on the DSC (measured at a heating rate of 10° C./min during the first heating cycle) peak melting temperature ("PMT") for that polymer. In general, the irradiation temperature in the IMS process is at least about 2° C. higher than the PMT, more preferably between about 2° C. and about 20° C. higher than the PMT, and most preferably between about 5° C. and about 10° C. higher than the PMT.

Exemplary ranges of acceptable total dosages are disclosed in greater detail in U.S. Pat. Nos. 5,879,400, and 6,641,617, and International Application WO 97/29793. For example, preferably a total dose of about or greater than 1 MRad is used. More preferably, a total dose of greater than about 20 Mrad is used.

In electron beam IMS, the energy deposited by the electrons is converted to heat. This primarily depends on how well the sample is thermally insulated during the irradiation. With good thermal insulation, most of the heat generated is not lost to the surroundings and leads to the adiabatic heating of the polymer to a higher temperature than the irradiation temperature. The heating could also be induced by using a high enough dose rate to minimize the heat loss to the surroundings. In some circumstance, heating may be detrimental to the sample that is being irradiated. Gaseous by-products, such as hydrogen gas when the polymer is irradiated, are formed during the irradiation. During irradiation, if the heating is rapid and high enough to cause rapid expansion of the gaseous by-products, and thereby not allowing them to diffuse out of the polymer, the polymer may cavitate. The cavitation is not desirable in that it leads to the formation of defects (such as air pockets, cracks) in the structure that could in turn adversely affect the mechanical properties of the polymer and in vivo performance of the device made thereof.

The temperature rise depends on the dose level, level of insulation, and/or dose rate. The dose level used in the irradiation stage is determined based on the desired properties. In general, the thermal insulation is used to avoid cooling of the polymer and maintaining the temperature of the polymer at the desired irradiation temperature. Therefore, the temperature rise can be controlled by determining an upper dose rate for the irradiation.

In embodiments of the present invention in which electron radiation is utilized, the energy of the electrons can be varied to alter the depth of penetration of the electrons, thereby controlling the degree of cross-linking following irradiation. The range of suitable electron energies is disclosed in greater detail in U.S. Pat. Nos. 5,879,400, 6,641,617, and International Application WO 97/29793. In one embodiment, the energy is about 0.5 MeV to about 12 MeV. In another embodiment the energy is about 1 MeV to 10 MeV. In another embodiment, the energy is about 10 MeV.

(ii) Cold Irradiation (CIR):

Cold irradiation is described in detail in U.S. Pat. No. 6,641,617, U.S. Pat. No. 6,852,772, and WO 97/29793. In the cold irradiation process, a polymer is provided at room temperature or below room temperature. Preferably, the temperature of the polymer is about 20° C. Then, the polymer is irradiated. In one embodiment of cold irradiation, the polymer may be irradiated at a high enough total dose and/or at a fast enough dose rate to generate enough heat in the polymer to result in at least a partial melting of the crystals of the polymer.

Gamma irradiation or electron radiation may be used. In general, gamma irradiation results in a higher dose penetration depth than electron irradiation. Gamma irradiation, however, generally requires a longer duration of time, which can result in more in-depth oxidation, particularly if the gamma irradiation is carried out in air. Oxidation can be reduced or prevented by carrying out the gamma irradiation in an inert gas, such as nitrogen, argon, neon, or helium, or under vacuum. Electron irradiation, in general, results in more limited dose penetration depths, but requires less time and, therefore, reduces the risk of extensive oxidation. Accordingly, gamma irradiation or electron irradiation may be used based upon the depth of penetration preferred, time limitations and tolerable oxidation levels.

The total dose of irradiation may be selected as a parameter in controlling the properties of the irradiated polymer. In particular, the dose of irradiation can be varied to control the degree of cross-linking in the irradiated polymer. The preferred dose level depends on the molecular weight of the polymer and the desired properties that will be achieved following irradiation. In general, increasing the dose level with CIR would lead to an increase in wear resistance.

Exemplary ranges of acceptable total dosages are disclosed in greater detail in U.S. Pat. Nos. 6,641,617 and 6,852,772, International Application WO 97/29793, and in the embodiments below. In one embodiment, the total dose is about 0.5 MRad to about 1,000 Mrad. In another embodiment, the total dose is about 1 MRad to about 100 MRad. In yet another embodiment, the total dose is about 4 MRad to about 30 MRad. In still other embodiments, the total dose is about 20 MRad or about 15 MRad.

If electron radiation is utilized, the energy of the electrons also is a parameter that can be varied to tailor the properties of the irradiated polymer. In particular, differing electron energies will result in different depths of penetration of the electrons into the polymer. The practical electron energies range from about 0.1 MeV to 16 MeV giving approximate iso-dose penetration levels of 0.5 mm to 8 cm, respectively. A preferred electron energy for maximum penetration is about 10 MeV, which is commercially available through vendors such as Studer (Daniken, Switzerland) or E-Beam Services (New Jersey, USA). The lower electron energies may be preferred for embodiments where a surface layer of the polymer is preferentially cross-linked with gradient in cross-link density as a function of distance away from the surface.

(iii) Warm Irradiation (WIR):

Warm irradiation is described in detail in U.S. Pat. No. 6,641,617 and WO 97/29793. In the warm irradiation process, a polymer is provided at a temperature above room temperature and below the melting temperature of the polymer. Then, the polymer is irradiated. In one embodiment of warm irradiation, which has been termed "warm irradiation adiabatic melting" or "WIAM." In a theoretical sense, adiabatic heating means an absence of heat transfer to the surroundings. In a practical sense, such heating can be achieved by the combination of insulation, irradiation dose rates and irradiation time periods, as disclosed herein and in the documents cited herein. However, there are situations where irradiation causes heating, but there is still a loss of energy to the surroundings. Also, not all warm irradiation refers to an adiabatic heating. Warm irradiation also can have non-adiabatic or partially (such as about 10-75% of the heat generated is lost to the surroundings) adiabatic heating. In all embodiments of WIR, the polymer may be irradiated at a high enough total dose and/or a high enough dose rate to generate enough heat in the polymer to result in at least a partial melting of the crystals of the polymer.

The polymer may be provided at any temperature below its melting point but preferably above room temperature. The temperature selection depends on the specific heat and the enthalpy of melting of the polymer and the total dose level that will be used. The equation provided in U.S. Pat. No. 6,641,617 and International Application WO 97/29793 may be used to calculate the preferred temperature range with the criterion that the final temperature of polymer maybe below or above the melting point. Preheating of the polymer to the desired temperature may be done in an inert (such as under nitrogen, argon, neon, or helium, or the like, or a combination thereof) or non-inert environment (such as air).

In general terms, the pre-irradiation heating temperature of the polymer can be adjusted based on the peak melting temperature (PMT) measure on the DSC at a heating rate of 10° C./min during the first heat. In one embodiment the polymer is heated to about 20° C. to about PMT. In another embodiment, the polymer is pre-heated to about 90° C. In another embodiment, the polymer is heated to about 100° C. In another embodiment, the polymer is pre-heated to about 30° C. below PMT and 2° C. below PMT. In another embodiment, the polymer is pre-heated to about 12° C. below PMT.

In the WIAM embodiment of WIR, the temperature of the polymer following irradiation is at or above the melting temperature of the polymer. Exemplary ranges of acceptable temperatures following irradiation are disclosed in greater detail in U.S. Pat. No. 6,641,617 and International Application WO 97/29793. In one embodiment, the temperature following irradiation is about room temperature to PMT, or about 40° C. to PMT, or about 100° C. to PMT, or about 110° C. to PMT, or about 120° C. to PMT, or about PMT to about 200° C. These temperature ranges depend on the polymer's PMT—most hydrogels melt below 100° C. when fully hydrated but the PMT is much higher with reduced level of hydration. In another embodiment, the temperature following irradiation is about 145° C. to about 190° C. In yet another embodiment, the temperature following irradiation is about 145° C. to about 190° C. In still another embodiment, the temperature following irradiation is about 150° C.

In WIR, gamma irradiation or electron radiation may be used. In general, gamma irradiation results in a higher dose penetration depth than electron irradiation. Gamma irradiation, however, generally requires a longer duration of time, which can result in more in-depth oxidation, particularly if the gamma irradiation is carried out in air. Oxidation can be reduced or prevented by carrying out the gamma irradiation in an inert gas, such as nitrogen, argon, neon, or helium, or under vacuum. Electron irradiation, in general, results in more limited dose penetration depths, but requires less time and, therefore, reduces the risk of extensive oxidation. Accordingly, gamma irradiation or electron irradiation may be used based upon the depth of penetration preferred, time limitations and tolerable oxidation levels. In the WIAM embodiment of WIR, electron radiation is used.

The total dose of irradiation may also be selected as a parameter in controlling the properties of the irradiated polymer. In particular, the dose of irradiation can be varied to control the degree of cross-linking in the irradiated polymer. Exemplary ranges of acceptable total dosages are disclosed in greater detail in U.S. Pat. No. 6,641,617 and International Application WO 97/29793.

The dose rate of irradiation also may be varied to achieve a desired result. The dose rate is a prominent variable in the WIAM process. The preferred dose rate of irradiation would be to administer the total desired dose level in one pass under the electron-beam. One also can deliver the total dose level with multiple passes under the beam, delivering a (equal or unequal) portion of the total dose at each time. This would lead to a lower effective dose rate.

Ranges of acceptable dose rates are exemplified in greater detail in U.S. Pat. No. 6,641,617 and International Application WO 97/29793. In general, the dose rates will vary between 0.5 Mrad/pass and 50 Mrad/pass. The upper limit of the dose rate depends on the resistance of the polymer to cavitation/cracking induced by the irradiation.

If electron radiation is utilized, the energy of the electrons also is a parameter that can be varied to tailor the properties of the irradiated polymer. In particular, differing electron energies will result in different depths of penetration of the electrons into the polymer. The practical electron energies range from about 0.1 MeV to 16 MeV giving approximate iso-dose penetration levels of 0.5 mm to 8 cm, respectively. The preferred electron energy for maximum penetration is about 10 MeV, which is commercially available through vendors such as Studer (Daniken, Switzerland) or E-Beam Services New Jersey, USA). The lower electron energies may be preferred for embodiments where a surface layer of the polymer is preferentially cross-linked with gradient in cross-link density as a function of distance away from the surface.

(iv) Subsequent Melting (SM)—Substantial Elimination of Detectable Residual Free Radicals:

Depending on the polymer or polymer alloy used, and whether the polymer was irradiated below its melting point, there may be residual free radicals left in the material following the irradiation process. A polymer irradiated below its melting point with ionizing radiation contains cross-links as well as long-lived trapped free radicals. Some of the free radicals generated during irradiation become trapped in the crystalline regions and/or at crystalline lamellae surfaces leading to oxidation-induced instabilities in the long-term (see Kashiwabara, H. S. Shimada, and Y. Hori, *Radiat. Phys. Chem.*, 1991, 37(1): p. 43-46; Jahan, M. S. and C. Wang, *Journal of Biomedical Materials Research*, 1991, 25: p. 1005-1017; Sutula, L. C., et al., *Clinical Orthopedic Related Research*, 1995, 3129: p. 1681-1689.). The elimination of these residual, trapped free radicals through heating can be, therefore, desirable in precluding long-term oxidative instability of the polymer. Jahan M. S. and C. Wang, *Journal of Biomedical Materials Research*, 1991, 25: p. 1005-1017; Sutula, L. C., et al., *Clinical Orthopedic Related Research*, 1995, 319: p. 28-4.

Residual free radicals may be reduced by heating the polymer above the melting point of the polymer used. The heating allows the residual free radicals to recombine with each other. If for a given system the preform does not have substantially any detectable residual free radicals following irradiation, then a later heating step may be omitted. Also, if for a given system the concentration of the residual free radicals is low enough to not lead to degradation of device performance, the heating step may be omitted.

The reduction of free radicals to the point where there are substantially no detectable free radicals can be achieved by heating the polymer to above the melting point. The heating provides the molecules with sufficient mobility so as to eliminate the constraints derived from the crystals of the polymer, thereby allowing essentially all of the residual free radicals to recombine. Preferably, the polymer is heated to a temperature between the peak melting temperature (PMT) and degradation temperature ($T_d$) of the polymer, more preferably between about 3° C. above PMT and $T_d$, more preferably between about 10° C. above PMT and 50° C. above PMT, more preferably between about 10° C. and 12° C. above PMT and most preferably about 15° C. above PMT.

In certain embodiments, there may be an acceptable level of residual free radicals in which case, the post-irradiation annealing also can be carried out below the melting point of the polymer, the effects of such free radicals can be minimized or eliminated by an antioxidant.

(v) Sequential Irradiation:

The polymer is irradiated with either gamma or e-beam radiation in a sequential manner. With e-beam the irradiation is carried out with multiple passes under the beam and with gamma radiation the irradiation is carried out in multiple passes through the gamma source. Optionally, the polymer is thermally treated in between each or some of the irradiation passes. The thermal treatment can be heating below the melting point or at the melting point of the polymer. The irradiation at any of the steps can be warm irradiation, cold irradiation, or melt irradiation, as described above. For example the polymer is irradiated with 30 kGy at each step of the cross-linking and it is first heated to about 120° C. and then annealed at about 120° C. for about 5 hours after each irradiation cycle.

(vi) Blending and Doping:

As stated above, the cross-liked polymeric material can optionally have a melt history, meaning it is melted concurrent with or subsequent to irradiation. The polymeric material can be blended with an antioxidant prior to consolidation and irradiation. Also, the consolidated polymeric material can be doped with an antioxidant prior to or after irradiation, and optionally can have been melted concurrent with or subsequent to irradiation. Furthermore, a polymeric material can both be blended with an antioxidant prior to consolidation and doped with an antioxidant after consolidation (before or after irradiation and optional melting). The polymeric material can be subjected to extraction at different times during the process, and can be extracted multiple times as well.

Stabilization of PAA in System:

1. Dehydration in air, vacuum, inert gas, and/or solvents.

Once PVA gels containing PAA are made using any of the above methods described herein, the gels are dehydrated in one or combination of the following environments: in air, vacuum, inert gas, or organic solvents. For example, the gels are dehydrated in an atmosphere containing 100% air, 100% inert gas, a mixture of one or more inert gases mixed with 0.1% to 99.9% air, or a mixture of one or more inert gases containing 0.1% to 99.9% oxygen. Dehydration of PAA containing PVA gels can render PAA molecules physically trapped inside the PVA gel network by densification, pore collapse, or further PVA crystallization.

2. Dehydration in air, vacuum, inert gas at elevated temperature, such as below or above 80° C., for example above room temperature to about 100° C.

Once PVA gels containing PAA are made using any of the above methods, the gels are dehydrated in one or combination of the following environments: in air, vacuum, and/or inert gas at an elevated temperature below the melting point of the said gel. For example, the gels are dehydrated in an atmosphere containing 100% air, 100% inert gas, a mixture of one or more inert gases mixed with 0.1% to 99.9% air, or a mixture of one or more inert gases containing 0.1% to 99.9% oxygen. Dehydration of PAA containing PVA gels can render PAA molecules physically trapped inside the PVA gel network by densification, pore collapse, or further PVA crystallization.

3. Dehydration in air, vacuum, inert gas, solvents, followed by thermal treatment in vacuum, inert gas at temperature above or below 160° C., for example, above about 80° C. to about 260° C.

Once PVA gels containing PAA are made using any of the above methods 1-6, the gels are dehydrated in one or combination of the following environments: in air, vacuum, and/or inert gas, at an elevated temperature below the melting point of the said gel. For example, the gels are dehydrated in an atmosphere containing 100% air, 100% inert gas, a mixture of one or more inert gases mixed with 0.1% to 99.9% air, or a mixture of one or more inert gases containing 0.1% to 99.9% oxygen. Dehydration of PAA containing PVA gels can render PAA molecules physically trapped inside the PVA gel network by densification, pore collapse, or further PVA crystallization. Subsequent to dehydration, the said gel can be thermally treated in vacuum, or inert gas at an elevated temperature higher than 100° C., preferably above or below 160° C., for example, above 80° C. to about 260° C., for about an hour up to about 20 hours or longer. Such thermal treatments can improve mechanical strength of the gels by further increasing PVA crystallinity.

4. Thermal treatment under high pressure.

Thermal treatment method described above also can be done at an elevated pressure than the ambient atmosphere.

5. Cross-linking by anhydrides and esters.

Thermal treatment methods described above can chemically cross-link PAA chains by forming anhydrides between carboxylic acids thus making PAA-interpenetrating network with PVA network. Hydroxyl groups in PVA and carboxylic acids in PAA also can form esters during such thermal treatments.

6. Cross-linking by gamma, e-beam irradiation.

In some embodiments radiation cross-linking in the PAA containing PVA gels processed by methods described here are carried by gamma or e-beam irradiation. The cross-linking increases the wear resistance and creep resistance. The cross-linking can be carried out at any step of the processing/methods described herein.

7. Cross-linking by cross-linking agents.

Another type of chemical cross-liking method is using cross-linking agents such as ethyleneglycol dimethacrylate (EGDMA) to cross-link PAA chains in the PVA-PAA gels processed by methods described above. Cross-linkers such as glutaraldehyde and epichlorohydrin can cross-link PVA chains in the said gel to improve mechanical properties in addition to physical locking of the incorporated PAA in the said gel.

8. Cross-linking of PAA during pH-induced volume transition.

The charge density of the PAA chains is pH-tunable which enables systematic control of the electrostatic repulsion imparted from the anionic charges. By adjusting the charge density by lowering the pH of the PAA-containing gel well below its pKa values, one can increase the number of protonated carboxylates in PAA, which can bring PAA chains closer and also promote intramolecular or intermolecular hydrogen bonding in PAA. PAA chains at such a state are cross-linked among themselves or with neighboring PVA chains by any of the methods described above. Increasing the pH of the said gel back to physiological pH value deprotonates the non-cross-linked acid groups in PAA, whose electrostatic repulsion will benefit the mechanical integrity of the gels under repetitive loading condition expected in the joint space.

Structural Design for Gradient Properties from PAA Incorporation:

1. Controlled diffusion of PAA into the PVA cryogels for gradient distribution of PAA in the recipient gel.

The effects of incorporated PAA into the PVA gels can be controlled to result in a non-uniform gel with a gradient of properties, i.e., larger effects from the presence of PAA on the gel surface than the bulk of the gel by having a higher PAA concentration on the surface than the bulk. This is achieved by controlling and/or varying the diffusion rate. Diffusion rate will be faster with lower the molecular weight of PAA, with larger pores in the PVA, with increased porosity of PVA, with higher hydration of the PVA, and the like.

2. Layer-by-layer buildup to create "vertical" gradient properties.

PVA-PAA gels or PVA-PAA-PEG gels can be built up in a layer-by-layer fashion by sequentially molding different concentration solution in the mold to achieve gradient properties. The gradient is thus disposed in a direction perpendicular to the direction of deposit. A hot (for example, about 90° C.) PVA-PAA-PEG mixture solution is poured into a container up to a certain thickness to form the first layer. The solution in the mold is gelled by cooling down to the room temperature or lower temperature. Upon gelling, the first layer in the container is heated to a temperature below the melting temperature with no disruption of the formed layer. Another layer of solution is added from a hot PVA-PAA-PEG mixture to the first layer to ensure adhesion of the two layers. The second layer can be formed from same or different composition of the polymer solution, or a new component can be added in the mixture. The container is again cooled down to form a layered gel structure. This procedure can be repeated to the desired number of layers or thickness. Such layer-by-layer gel formation can be applied to PVA-PEG gels or PVA cryogel as well, followed by PAA diffusion.

3. Gradient effects of thermal treatment.

Thermal treatment on the PAA containing PVA gels can be deliberately controlled in a gradient manner by having one of the surfaces of the dehydrated gel in contact with higher temperature than the opposite surface of the said gel. The gel surface in contact with higher temperature will be affected more by heating, i.e., more cross-linking and higher crystallinity, lower water content, than the other surface in contact with lower temperature.

In other embodiments, creep resistant PVA-hydrogels can be prepared by several different ways, following various processing steps in different orders, for example:

Incorporation of acrylic acid (AA) monomer:
    Blending of PVA and AA in solution with PEG addition;
    Diffusion of AA into PVA-PEG gels;
    Freeze-thawing of PVA-AA gels;
    Freeze-thawing of PVA-AA-PEG gels;
    Freeze-thawing of PVA gels followed by diffusion of AA into PVA gels; and/or
    All of the above wherein the AA monomer is polymerized in situ.

Stabilization of PAA in system:
    Densification, collapsing pores (in DP samples) by dehydration.

Stabilization of AA in system:
    Dehydration in air, vacuum, inert gas, solvents;
    Dehydration in air, vacuum, inert gas at elevated temperature, such as below or above 80° C., for example above room temperature to about 100° C.;

Dehydration in air, vacuum, inert gas, solvents, followed by thermal treatment in vacuum, inert gas at temperature above or below 160° C., for example, above about 80° C. to about 260° C.;

All of the above under high pressure;

Cross-linking by heating—anhydrides, esters;

Cross-linking by gamma, e-beam irradiation;

Cross-linking by chemical agents—glutaraldehyde, epichlorohydrin, EGDMA; and/or

Densification, collapsing pores (in DP samples) by dehydration.

According to one embodiment, this invention provides fabricated PVA-hydrogels, PVA-hydrogel-containing compositions, and methods of making PVA-hydrogels and PVA-hydrogel-containing compositions. The invention also provides methods of using the fabricated PVA-hydrogels and PVA-hydrogel-containing compositions in treating a subject in need.

Hydrogels described in the prior art (see for example, U.S. Pat. Nos. 4,663,358, 5,981,826, and 5,705,780, US Published Application Nos. 20040092653 and 20040171740) can be used as starting materials for making PVA-hydrogels of the present invention by employing methods described herein for the first time. The PVA-hydrogels provided in the present invention can be used in a body to augment or replace any tissue such as cartilage, muscle, breast tissue, nucleus pulposus of the intervertebral disc, other soft tissue, interpositional devices that generally serves as a cushion within a joint, and the like.

PVA-hydrogels generally include polymer, polymer blends, or copolymers of polyvinyl alcohol (PVA), polyvinyl pyrrolidone (PVP), poly ethylene oxide (PEO), Polyacrylic acid (PAA), Poly(methacrylic acid) (PMAA), alginates, polysaccharides, polyoxyethylene-polyoxypropylene co-polymers, poly-N-alkylacrylamides, poly-N-isopropyl acrylamide (PNIAAm), chondroitin sulfate, dextran sulfate, dermatin sulfate, or combinations of two or more thereof.

PVA-hydrogels, as disclosed herein, comprised of uniformly distributed hydrogel molecules or hydrogel particles comprising polyvinyl alcohol (PVA) copolymerized and/or blended with at least one of the other polymers or gellants, for example, polyvinyl pyrrolidone (PVP), poly-N-isopropyl acrylamide (PNIPAAm), poly ethylene oxide (PEO), Polyacrylic acid (PAA), Poly(methacrylic acid) (PMAA), chondroitin sulfate, dextran sulfate, dermatin sulfate and the like, or combinations of two or more thereof.

According to one aspect of the invention, the PVA-hydrogels comprise polyvinyl alcohol (PVA) copolymerized and/or blended with at least one of the other polymers.

According to another aspect of the invention, the hydrogel solutions comprise polyvinyl alcohol (PVA), Polyacrylic acid (PAA), Poly(methacrylic acid) (PMAA), polyvinyl pyrrolidone (PVP), poly ethylene oxide (PEO), poly-N-isopropyl acrylamide (PNIAAm), or combinations of two or more thereof.

According to another aspect of the invention, the hydrogel solution is a polyvinyl alcohol (PVA) solution.

PVA-hydrogels of the invention can be used in a variety of fashions in joints in mammals such as human joints. For example, an interpositional device can be manufactured from the PVA-hydrogels, which meet required mechanical strength to withstand high loads of human joints, and can be used in articular cartilage replacement applications. The interpositional devices typically act as a cushion within the joint to minimize the contact of the cartilage surfaces to each other. This is beneficial in patients with arthritic joints. Early arthritic joints with cartilage lesions can be treated with such interpositional devices, which minimizes the contact between the damaged cartilage surfaces of the patient. The interpositional devices are described by Fell et al. (see U.S. Pat. Nos. 6,923,831, 6,911,044, 6,866,684, and 6,855,165). These devices can have a variety of shapes and sizes. For a hydrogel inter positional device to perform in vivo in the long-term, the device first needs to have a high creep resistance. This is to minimize the changes to the shape of the interpositional hydrogel device during in vivo use. PVA-hydrogel materials of the invention with increased stiffness display increased creep resistance. The hydrogel interpositional device according to the invention also have superior mechanical properties, such as toughness, wear resistance, high creep resistance, and the like.

Another method for the use of a hydrogel implant is through the filling of a cavity in the joint. The cavity can be an existing one or one that is prepared by a surgeon. A PVA-hydrogel plug can be inserted into the cavity. The hydrogel plug can be of any shape and size; for instance it can be cylindrical in shape. In some embodiments the plug can be oversized to be elevated from the surrounding cartilage surface. In other embodiments the plug can be undersized to stay recessed in the cavity. The over-sizing or under-sizing can be such that the plug can stand proud above the surrounding cartilage surface or recessed from the surrounding cartilage surface by about less than 1 mm, by about 1 mm, by more than about 1 mm, by about 2 mm, by about 3 mm, or by about more than 3 mm. In some embodiments the hydrogel plug can be slightly dehydrated to shrink its size and to allow an easy placement into the cavity. The hydrogel plug then can be hydrated and swollen in situ to cause a better fit into the cavity. The dehydrated and re-hydrated dimensions of the hydrogel plug can be tailored to obtain a good fit, under-sizing, or over-sizing of the plug after re-dehydration and re-swelling. The re-dehydration in situ can also be used to increase the friction fit between the plug and the cavity. This can be achieved by tailoring the dimensions and the extent of dehydration such that upon re-dehydration the cross-section of the plug can be larger than the cross-section of the cavity; by for instance about 1 mm, less than 1 mm, or more than 1 mm. In some embodiments the cavity can be filled with an injectable hydrogel system known in the art, such as the one described by Ruberti and Braithwaite (see US Published Application Nos. 20040092653 and 20040171740), Muratoglu et al. (International Application WO 2006/125082), Lowman (US Published Application No. 20040220296), and other injectable systems.

The present invention also provides methods of fabricating PVA-hydrogel systems to obtain PVA-hydrogels that can maintain shape under the high stress of human joints. According to one aspect of the invention, the PVA-hydrogels are obtained by improving the stiffness, toughness and strength of hydrogels to increase resistance to creep and resistance to wear. The invention provides dehydration methods useful for improving the mechanical properties of the hydrogel. Various dehydration methods, described above, can be used together in combinations to improve the properties of hydrogels. Any of the dehydration methods can be used either by itself or in combination with the other dehydration methods to improve the mechanical properties of hydrogels.

In the case of extreme dehydration of the PVA-hydrogel, it can be important for some of the applications to subsequently re-hydrate the PVA-hydrogel at least to some extent to regain the lubrication imparted by the presence of water for some of the embodiments. If the heat dehydration is carried out starting with a hydrogel that contains water and one or more other ingredient(s), which are in most embodiments non volatile such as low molecular weight PEG, and others such as PVP, PEO, PAA, PMAA, chondrotin sulfate, the dehydrated hydrogel is easily re-hydrated to varying levels. According to one aspect of the invention, the level of re-hydration following heat dehydration depends on the concentration of other ingredient(s) in the water phase of the initial hydrogel before dehydration. In contrast, if the starting hydrogel contains no other ingredients but water, then the extent of re-hydration subsequent to heat dehydration is substantially reduced compared to the re-hydration levels of the hydrogels dehydrated in the presence other ingredient(s). The presence of the other ingredient(s) other than water also has implication on the creep behavior of the hydrogel following heat dehydration and subsequent re-hydration. The hydrogel is more viscoelastic when it is heat treated in the presence of other ingredient(s).

According to another aspect, PVA-hydrogels containing a low molecular weight ingredient, such as PEG, retain their opacity during heat dehydration. In contrast, PVA-hydrogels containing no such ingredients and heat dehydrated under identical conditions lose their opacity and turn transparent, an indication for the loss of the molecular porosity. The molecular porosity is thought to be the free space in the structure where the water molecules penetrate the hydrogel, thus hydrating it. The loss of the opacity upon heat dehydration of hydrogels not containing any such ingredient can be the reason for their substantially reduced ability to re-hydrate. According to one aspect on the invention, the non-volatile ingredient remains in the hydrogel structure during heat dehydration and prevents the collapse of the molecular porosity, and thus allowing these hydrogels to re-hydrate following heat dehydration.

The invention also provides freeze-thaw prepared PVA-PAA (FT-PVA-PAA) hydrogels, wherein the PVA-PAA-hydrogel is further treated by heating at around 160° C. Upon re-hydration, the heated gels remain transparent forming an elastic and tough, almost rubber-like material. While this material is useful in some application, it may not be for applications requiring high water content in the hydrogel. The extent of re-hydration is further tailored in the heated FT-PVA-PAA by adding an ingredient such as PEG into the water phase prior to the heating.

In another embodiment, the PVA-hydrogel implant is packaged and sterilized. The packaging can be such that the hydrogel device is immersed in an aqueous solution to prevent dehydration until implantation, such as during sterilization and storage. The aqueous solution can be water, deionized water, saline solution, Ringer's solution, or salinated water. The aqueous solution also can be a solution of polyethylene glycol in water. The solution can be of less than 5% (wt) in PEG, about 5% (wt), more than about 5% (wt), about 10% (wt), about 15% (wt), about 20% (wt), about 30% (wt), about 50% (wt), about 90% (wt) or about 100% (wt). The hydrogel device also can be sterilized and stored in a non-volatile solvent or non-solvent.

The sterilization of the PVA-hydrogel implant can be carried out through gamma sterilization, heat, gas plasma sterilization, or ethylene oxide sterilization, for example. According to one embodiment, the hydrogel is sterilized by autoclave. The sterilization is carried out at the factory; or alternatively, the implant is shipped to the hospital where it is sterilized by autoclave. Some hospitals are fitted with ethylene oxide sterilization units, which also is used to sterilize the hydrogel implant.

In one embodiment, the hydrogel implant is sterilized after packaging. In other embodiments the hydrogel implant is sterilized and placed in a sterile aqueous solution.

In another embodiment, PVA-PAA-hydrogel is prepared using the freeze-thaw method starting with an aqueous PVA solution (at least about 10% (wt) PVA, above about 15% (wt) PVA, about 20% (wt) PVA, about 25% (wt) PVA, about 27% (wt) PVA, about 30% (wt) PVA, about 35% (wt) PVA, about 40% (wt) PVA, about 45% (wt) PVA, above about 50% (wt) PVA) and subjecting it to freeze-thaw cycles (at least 1 cycle, more than 1, 2, 3, 4, 5, 6, 7, 8, 9, 10 or more cycles). The freeze-thaw cycle is defined as cooling the PVA solution below 0° C. and heating it back up above 0° C. The PVA-PAA-hydrogel is then subjected to dehydration. Subsequently, the dehydrated hydrogel is placed in saline solution for re-hydration. This process results in very little re-hydrated PVA-PAA-hydrogel with high mechanical strength.

In another embodiment, the invention provides a process of modification of PVA-hydrogels to increase water content, improve lubricity, with least compromise with mechanical strength, such as creep resistance by addition of hydrophilic ionic molecules such as PAA by methods of blending prior to gelling and/or diffusion into the formed gel.

In another embodiment, the invention provides a process incorporation of solvents such as PEG during subsequent processing on PVA-PAA gels to prevent loss of mechanical integrity and maintain high water affinity by methods of blending PEG during PVA-PAA gel formation; diffusing PEG into the PVA-PAA gels; and/or diffusing PEG simultaneously or sequentially as PAA into the PVA gels.

In one embodiment of the invention, the PVA:PAA ratio can be about 99.9:0.1 to 5:5, for example, 99.5:0.5, 99:1, 79:1, 59:1, 39:1, 19:1, 9:1, 8:2, 7:3, 6:4, 5:5, or any ratio thereabout, or therebetween, with the total polymer content in the mixture at about 10%, 15%, 20%, 25%, 27%, 30%, 35%, 40%, 45%, 50%, or any value thereabout, therebetween, or higher. In another embodiment, the composition ratio of PAA to PVA in the final gel content can be about 0.1% to 90%. In another embodiment, the polymer content of the basal PVA-PAA hydrogel can be 10% up to 90%. Average molecular weight of PAA for blending or diffusion can be about 2,000 up to 1 million.

According to one aspect of the invention, PAA diffusion can be done by immersing basal PVA gels in aqueous PAA solutions or in mixture solutions with PEG or other solvents such as alcohol, DMSO, NaCl solution, $CaCl_2$ solution, saline, ringer's solution, phosphate buffered saline, super-critical fluid, and the like. PAA diffusion can be done at an elevated temperature, such as below or above 80° C., for example above room temperature to about 100° C. PAA diffusion can be done in PAA solutions with concentrations ranging from about 0.1% to 70%.

In another embodiment, the invention provides a process of controlled diffusion of PAA into the PVA gels for gradient distribution of PAA in the recipient gel. PAA containing PVA gels can be dehydrated in air, vacuum, inert gas, solvents for physical fixation of PAA in the PVA gel at room temperature, or at an elevated temperature, such as below or above 80° C., for example above room temperature to about 100° C. Thermal treatment following dehydration on PAA containing PVA gels can be done in vacuum, inert gas, at an elevated temperature, for example, higher than 100° C., preferably above or below 160° C., for example, above about 80° C. to about 260° C., for 1 hour up to 20 hours or longer for irreversibly linking PAA in the hydrogel network and improve creep resistance. Thermal annealing following dehydration on PAA containing PVA gels in vacuum or inert gas also can be done by heating at heating rates such as about 0.01° C./min, about 0.1° C./min, about 1° C./min, or about 10° C./min, starting at room temperature or at an elevated temperature, such as below or above 80° C., for example above room temperature to about 100° C., up to a final temperature higher than about 100° C., preferably above or below 160° C., for example, above about 80° C. to about 260° C., for about one hour up to 24 hours or longer.

Thermal annealing, a post-gelation toughening method to improve the creep resistance in physically cross-linked PVA hydrogels, can cause changes in the EWC and lubricity of PVA hydrogels. By blending PAA in PVA solutions prior to gelation, thus to form PAA-containing PVA hydrogels, hydrophilicity and compressive strength of the PVA gels can be increased by imparting negative charges into the non-charged PVA gel matrix. Thermal annealing process on PVA-PAA hydrogels also can make gels brittle due to thermally-induced cross-linking of the PAA and PVA chains, especially when the annealing is carried out in air. However, according to an aspect of the invention, the presence of low molecular weight PEG, such as PEG400, during the thermal annealing, can alleviate these problems. PEG400 molecules, for example, residing in PAA-containing PVA hydrogels can alleviate or prohibit esterification that occurs between the hydroxyl groups of PVA and the carboxylic acids of PAA during thermal annealing by screening such functional groups of PVA and PAA in the vicinity. According to another aspect of the invention, presence of PEG during thermal annealing can significantly improve the surface lubricity of the PAA containing PVA hydrogels.

In another embodiment, presence of PEG during thermal annealing can significantly improve the surface lubricity of the PAA containing PVA hydrogels. PEG can protect the pores in the gels from collapsing during the annealing process so that the preserved pores can retain water content easily upon rehydration, which is favorable for surface lubrication. PEG is known to undergo thermo-oxidative degradation in the presence of air. During thermal degradation in air, PEG reacts with oxygen and forms thermally labile α-hydroperoxide, which can produce low molecular weight esters such as formic ester. Such degradation process of PEG in air can be further facilitated when carboxylic groups from other polymeric components co-exist in the gel, which can be, for example, poly(acrylic acid) in the present invention. Thermal degradation products or derivatives of PEG can react with PVA or PAA in the gels during the annealing process to create more negatively charged groups on the gel, which can further improve surface lubricity of the gels.

Two types of gels, for example, PEG-doped (Type 1) and PEG-blended (Type 2) with different blending ratios of PVA:PAA can be used.

Type 1—PEG-Doped Gels:

PVA-PAA solution is poured into pre-heated glass sheet molds and subjected to three freeze-thaw cycles (about 16 hour-freezing at −17° C. and about 8 hour-thawing at room temperature). Subsequently, the molded gels are immersed in 100% PEG (PEG-doping by immersion) followed by vacuum dehydration and annealing at about 160° C. under inert environment (such as in argon) in a self-pressurized vessel or in air for about one hour or more.

Type 2—PEG-Blended Gels:

About 15 w/w % PEG (with respect to the total PEG and the amount of water in the PVA-PAA mixture) is pre-heated at about 90° C. and added to a hot PVA-PAA mixture to form PVA-PAA-PEG homogeneous solution. Resulting homogeneous polymer blend is poured into a pre-heated glass mold. Subsequently, the molded gel is subjected to three freeze-thaw cycles followed by vacuum dehydration and annealing at about 160° C. under inert environment (such as in argon) in a self-pressurized vessel or in air for about one hour or more.

Each gel sheet is immersed in deionized (DI) water to remove residual PEG and to reach an equilibrated rehydration.

The non-annealed "PVA only" (that is, PVA with no PAA) gels in both Types 1 and 2 are made by rehydrating the gels in DI water immediately upon removal from the molds after completion of the freeze-thaw cycles.

According to another aspect of invention, combination of the PEG doping step with the presence of PAA in the PVA hydrogels can increase equilibrium water content and lower the coefficient of friction in PVA hydrogels. For example, during the PEG-doping step as described in Type 1 gels, PEG can diffuse in and fill the micro- and nano-pores existing in the PAA-containing PVA hydrogel gels upon gelation, subsequently protect the pores from collapsing during annealing. Upon rehydration following the annealing process, the preserved pores can accelerate water absorbency in the PVA-PAA gels, resulting in higher EWC and improved surface lubricity than non PEG-doped PVA-PAA gels where the pores are presumably collapsed.

In another embodiment, PVA:PAA ratio can be in about 99.9:0.1 to 5:5, for example, 99.5:0.5, 99:1, 79:1, 59:1, 39:1, 19:1, 9:1, 8:2, 7:3, 6:4, 5:5, or any ratio thereabout, or therebetween, with the total polymer content in the mixture at about 10%, 15%, 20%, 25%, 27%, 30%, 35%, 40%, 45%, 50%, any value thereabout, therebetween, or higher.

According to another aspect of invention, pH-induced phase-separation of PVA-PAA solutions into the PVA-rich and PAA-rich domains prior to gelation can increase creep resistance of PAA-containing PVA hydrogels. PAA is known to lower crystallization of PVA due to hindrance of carboxylic groups when coexisting with PVA in the molecular level. Since the mechanical strength of the PVA hydrogel comes from degree of PVA crystallinity in the physically crosslinked PVA hydrogels, the presence of PAA chains that hinders crystallization of PVA chains nearby can compromise the mechanical strength of the PVA hydrogels. However, the presence of PAA increases the equilibrium water content and provides high surface lubricity in annealed PVA hydrogels. Therefore, if PAA chains are separated from PVA chains in the immiscible blends of PVA and PAA, PVA chains in the separated PVA domains can further crystallize without disturbance from PAA through thermal annealing process, while PAA chains still can maintain high water retainability which imparts surface lubricity upon rehydration. The carboxylic acid groups in PAA chains are almost 100% protonated at lower pH values than pH 1.5. Carboxylic acids in PAA actively form hydrogen-bonds with hydroxyl groups in PVA chains to promote miscibility among PVA and PAA chains at the acidic regime with low pH. However, when PAA molecules are partially ionized with increasing pH, the hydrogen bonds between PAA and PVA chains start to break, lowering the miscibility of PVA and PAA, finally leading to an immiscible solution of PVA-PAA mixture.

With further increase of solution pH above a certain pH value (which is the "miscibility transition inducing" pH ($pH_{mt}$)), at which the intermolecular interaction between PVA and PAA no longer favors PVA-PAA complex configuration, PVA-PAA mixture finally becomes an immiscible solution. For example, for making PAA-containing PVA hydrogel with 25% total polymer of 19:1 PVA:PAA ratio, the native pH of an aqueous PAA (1.654 w/w %) solution prior to dissolving PVA powder is about 3.0 at room temperature. Such composition without any additional pH-adjustment forms a completely clear miscible PVA-PAA solution with added PVA at 90° C. On the other hand, when the pH of 1.654 w/w % PAA solution is increased to a value of pH 5.5 prior to addition of PVA powder, the final PVA-PAA mixture turns into a slightly opaque immiscible blend. Therefore, the $pH_{mt}$ at which PVA-PAA solutions with 25% total polymer having a PVA:PAA ratio of 19:1 turn from miscible to immiscible blends can be a value between about 3.0 and about 5.5. The $pH_{mt}$ can vary depending on several factors such as the total polymer concentration, molecular weight of each polymer, PVA:PAA ratio, salt concentration or ionic strength of the solution and the like. By adjusting the pH values of the PVA-PAA solutions below or above the $pH_{mt}$, the miscibility of PVA-PAA solutions can be manipulated prior to gelation. Hence the molecular interaction among PVA and PAA chains during the gelation and the post-gelation process can be controlled by pH of the solution. Once the PAA-rich and PVA-rich domains are phase-separated in the immiscible PVA-PAA solution above the $pH_{mt}$, crystallization of PVA chains are less likely to be affected by the hindrance of PAA chains, thereby ultimately improving the creep resistance of the PAA containing PVA hydrogels through achieving high degree of PVA crystallinity.

According to another aspect of the invention, above described processes also can be carried under high pressure environment. The thermal treatment method described herein also can be carried out at an elevated pressure than the ambient atmosphere.

According to another aspect of the invention, cross-linking of PAA in PVA gels with or without PEG can be done by gamma or e-beam irradiation. Cross-linking of PAA in PVA gels with or without PEG can be done by chemical cross-liking method using cross-linking agents such as ethyleneglycol dimethacrylate (EGDMA). Cross-linking density of PAA in PVA gels can be controlled through pH-adjustment prior to cross-linking by altering the number of protonated carboxylates in PAA chains.

According to another aspect of the invention, "vertical" gradient properties of the final gel can be formed by composition control, for example, a) Layer-by-layer buildup of PVA-PAA gels with varying composition ratio of PVA to PAA in each layer by adding one layer at a time in repeated freeze-thawing process; b) Layer-by-layer buildup of PVA-PAA-PEG gels with varying composition ratio of PVA to PAA or PVA to PEG in each layer by adding one layer at a time in repeated freeze-thawing process or theta-gelling process; and c) co-extrusion to form layers of PVA/PAA and/or PV/PEG/PAA of different concentrations.

According to another aspect of the invention, the "vertical" gradient properties of the final gel can be also formed by heating condition control by a) having one of the surfaces of the dehydrated gel in contact with higher temperature than the opposite surface of the said gel; and b) having only one of the surfaces of the non-PEG containing dehydrated gel in contact with PEG during heating; and c) having one of the surfaces of the non-PEG containing, dehydrated gel in contact with PEG and higher temperature than the opposite surfaces of the said gel.

In one embodiment of the invention, PEG is used as a non-volatile non-solvent for PVA hydrogels. DMSO is used instead of water in preparing the aqueous PVA-PAA-solution, the precursor to the hydrogel.

In one embodiment of the invention, PEG solution is a solution of PEG in a solvent (preferably water, ethanol, ethylene glycol, DMSO, or others). The solution concentration can be anywhere between 0.1% (wt) PEG and 99.9% (wt) PEG. The PEG in the solution can be of different molecular weights (preferably 300, 400, or 500 g/mol, more than 300 g/mol, 1000 g/mol, 5000 g/mol or higher). The PEG in the solution can be a blend of different average molecular weight PEGs.

In another embodiment, PEG containing PVA-PAA-hydrogel is prepared using the freeze-thaw method starting with an aqueous PVA solution (at least about 10% (wt) PVA, about 15% (wt) PVA, about 20% (wt) PVA, about 25% (wt) PVA, about 27% (wt) PVA, about 30% (wt) PVA, about 35% (wt) PVA, about 40% (wt) PVA, about 45% (wt) PVA, about above 50% (wt) PVA) and subjecting it to freeze-thaw cycles (at least 1 cycle, more than 1, 2, 3, 4, 5, 6, 7, 8, 9, 10 or more cycles). At this step the PVA-PAA-hydrogel can be optionally placed in saline to reach full hydration. Subsequently, the gel is placed in a low molecular weight PEG solution. This is to dope the hydrogel with the non-solvent PEG. The duration of PEG solution soak can be varied to either reach a uniform equilibrium PEG content throughout the hydrogel or to reach a non-uniform PEG distribution (by shortening the soak duration). The latter results in PEG-rich skin and a gradient of PEG concentration within the PVA-PAA-hydrogel.

In another embodiment, PEG containing PVA hydrogel is prepared by starting with an aqueous PVA solution (at least about 10% (wt) PVA, above about 15% (wt) PVA, about 20% (wt) PVA, about 25% (wt) PVA, about 27% (wt) PVA, about 30% (wt) PVA, about 35% (wt) PVA, about 40% (wt) PVA, about 45% (wt) PVA, about above 50% (wt) PVA) and mixing it with a low molecular weight PEG solution at an elevated temperature (above room temperature or above 50° C.). Upon cooling down to room temperature, the mixture forms a PVA-PAA-hydrogel containing water and the non-solvent PEG. In another embodiment, the hot PVA-PAA/PEG mixture is not cooled to room temperature but instead is subjected to freeze-thaw cycles.

In another embodiment, PVA-PAA-hydrogel is heat dehydrated. The PVA-PAA-hydrogel contains PEG during heat dehydration (or heating). The heat dehydration is carried out at about 40° C., at above about 40° C., at about 80° C., at above 80° C., at 90° C., at about 100° C., at above 100° C., at about 150° C., at about 160° C., at above 160° C., at about 180° C., at above 180° C., at about 200° C., or at above 200° C. In another embodiment, the dehydration is carried out at about 40° C., about 80° C., about 90° C., about 100° C., about 150° C., about 160° C., about 180° C., about 200° C., or above 200° C. The duration and the temperature of the thermal treatment depends on the size and hydration level of the hydrogel, for example, the duration can be for about an hour or less, about 5 hours, about 10 hours, about 24 hours, several days, or a few weeks. The heat dehydration can be carried out in any environment, preferably in an inert gas like nitrogen or argon or in vacuum. The heat dehydration also can be carried out in air or acetylene gas or mixture of a number of gases. The heat dehydration can be carried out either by placing the hydrogel in an already heated environment to achieve a higher rate of heat dehydration or by heating the hydrogel slowly to achieve a slower rate of heat dehydration. The rate of heat dehydration can be such that the hydrogel loses weight from removal of water at a rate of 1% weight loss per day, 10% weight loss per day, 50% weight loss per day, 1% weight loss per hour, 10% weight loss per hour, 50% weight loss per hour, 1% weight loss per minute, 5% weight loss per minute, 10% weight loss per minute, 50% weight loss per minute or any amount thereabout or therebetween. The rate of heat dehydration depends on the rate at which the temperature is raised and the size of the hydrogel. Prior to heat dehydration, the hydration level of the hydrogel can be reduced by vacuum dehydration. Subsequent to the heat dehydration the hydrogel is placed in saline solution for re-hydration. This results in good levels of re-hydration in the PVA hydrogel resulting in high mechanical strength and good lubrication when articulating against human cartilage or other hydrophilic surfaces.

This hydrogel is expected to maintain its hydrogen bonded structure, thus is not be subject to dissolution over long-term in water, saline or bodily fluid.

Although the description and examples are given for a PVA-hydrogel systems, but can be applied to any hydrogel system of a polymeric structure, that is, with long-chain molecules. Therefore, the invention provides hydrogel systems that includes, but not limited to, PVA as the base material.

According to one aspect of the invention, polyvinyl alcohol (PVA) can be used as the base hydrogel. The base PVA-hydrogel can be prepared by the well-known freeze-thaw method by subjecting a PVA solution (PVA can be dissolved in solvents such as water or DMSO) to one or multiple cycles of freeze-thaw. PVA solution used in the freeze-thaw method can contain another ingredient like PEG. The base PVA-hydrogel also can be prepared by radiation cross-linking of a PVA solution. Another method of preparing the PVA-hydrogel can be used to blend a PVA solution with a gellant such as (PEG) at an elevated temperature and cooling down to room temperature.

In one embodiment, the hydrogel can be of any shape, such a cubical shape, cylindrical shape, rectangular prism shape, or implant shape.

In another embodiment, NIPAAm can be used as the base hydrogel. The base NIPAAm hydrogel can be prepared by radiation cross-linking of a NIPAAm solution. Alternatively, the methods described by Lowman et al. can be used.

In another embodiment, a topological gel (TP) can be used as the base hydrogel. The base TP hydrogel can be prepared by methods described by Tanaka et al. (see *Progress in Polymer Science*, 2005, 30: 1-9). The polymer chains in TP gels are flexibly bound by cross-linkers that are sliding along the individual chain.

In the following embodiments, a nanocomposite (NC) gel structure can be used as the base hydrogel. The base NC hydrogel can be prepared by methods described by Tanaka et al. (see *Prog. Polym. Sci.* 2005, 30: 1-9).

In some of the embodiments a dehydrated hydrogel can be used as the base hydrogel. The level of dehydration can be controlled such that the base hydrogel contains between 99% and 1% water, more preferably between 99% and 5% water, more preferably between 99% and 25% water, more preferably between 99% and 50% water, more preferably between 99% and 75% hydrogel, more preferably about 70% (wt) water, or 80% (wt) water.

The water content of the hydrogel can be determined by measuring the weight change of between its equilibrium hydration level and its dehydrated level.

In some embodiments, a hot solution of PVA/PAA/PEG in water is cooled down to room temperature and is used in its "as-gelled" form.

According to one aspect of the invention, the PVA-PAA-PEG-hydrogel is immersed in water, deionized water, saline solution, phosphate buffered saline solution, Ringer's solution or salinated water to remove the PEG. The process is called the dePEGing process. During dePEGing the hydrogel also absorbs water approaching equilibrium water content. Therefore, dePEGing also can be a re-hydration process.

In another embodiment, the dehydrated hydrogel is re-hydrated. In some of the embodiments, the re-hydrated hydrogel contains less water than the hydrogel did before the dehydration step.

In some embodiments, the hydrogel dimensions are large enough so as to allow the machining of a medical device.

Dehydration of the hydrogel can be achieved by a variety of methods. For instance, the hydrogel can be placed in vacuum at room temperature or at elevated temperatures to drive out the water and cause dehydration. The amount of vacuum can be reduced by adding air or inert gas to the vacuum chamber where the hydrogel is placed during dehydration. Dehydration of the hydrogel also can be achieved by keeping it in air or inert gas at room temperature or at an elevated temperature. Dehydration in air or inert gas also can be carried out at temperatures lower than room temperature. In many embodiments, if the dehydration is carried out at elevated temperatures, it is necessary to keep the temperature below the melting point of the hydrogel. However, the melting point of the hydrogel can increase during the dehydration step and make it possible to go to higher temperatures as the dehydration evolves. Dehydration of the hydrogel also can be carried out by placing the hydrogel in a solvent. In this case the solvent drives the water out of the hydrogel. For example, placing of PVA-PAA-hydrogel in a low molecular weight PEG (higher than 100 g/mol, about 300-400 g/mol, about 500 g/mol) can cause dehydration of the PVA-PAA-hydrogel. In this case the PEG can be used as pure or in a solution. The higher the PEG concentration the higher the extent of dehydration. The solvent dehydration also can be carried out at elevated temperatures. These dehydration methods can be used in combination with each other.

Re-hydration of the hydrogel can be done in water containing solutions such as, saline, water, deionized water, salinated water, or an aqueous solution or DMSO.

In some embodiments, the hydrogel is shaped into a medical device and subsequently dehydrated. The dehydrated implant is then re-hydrated. The initial size and shape of the medical implant is tailored such that the shrinkage caused by the dehydration and the swelling caused by the subsequent re-hydration (in most embodiments the dehydration shrinkage is larger than the re-hydration swelling) result in the desired implant size and shape that can be used in a human joint.

In certain embodiments, the PVA-PAA-hydrogel can be machined into a desired shape to act as medical device, such as a kidney shaped interpositional device for the knee, a cup shaped interpositional device for the hip, a glenoid shaped interpositional device for the shoulder, other shapes for interpositional devices for any human joint. Also the machining of the PVA-PAA-hydrogel can result in a cylindrical, cuboid, or other shapes to fill cartilage defects either present in the joint or prepared by the surgeon during the operation.

The PVA-PAA-hydrogel medical device can be an interpositional device such as a unispacer, to act as a free floating articular implant in a human joint, such as the knee joint, the hip joint, the shoulder joint, the elbow joint, and the upper and lower extremity joints.

In some of the embodiments, the PVA-PAA-hydrogel is placed in 100% PEG to dehydrate the hydrogel. Subsequently the dehydrated gel is placed in saline solution for re-hydration. This process decreases the equilibrium water content in the gel, and hence further improves the mechanical properties of the hydrogel.

In other embodiments, the PVA-PAA-hydrogel is placed in a PEG-water solution for controlled dehydration followed by re-hydration in saline. The concentration of the PEG-water solution can be tailored to achieve desired level of dehydration of the hydrogel. Higher dehydrations provide more improvements in mechanical properties and at lower dehydrations the improvement is less. In some applications, it is desirable to achieve a lower stiffness; therefore a lower PEG and/or water concentration solution can be used for the dehydration process.

In some embodiments the PVA-PAA-hydrogel is dehydrated in vacuum at room temperature or at an elevated temperature. The vacuum dehydration can be carried out at about 10° C., above about 10° C., about 20° C., about 30, 40, 50, 60, 75, 80, 90° C., about 100° C. or above 100° C., or at 130° C. or any temperature thereabout or therebetween.

In some embodiments the vacuum dehydration of the PVA-PAA-hydrogel is first carried out at room temperature until a desired level of dehydration is reached; thereafter the temperature is increased to further dehydrate the hydrogel. The temperature is increased, preferably to above about 100° C., to above or below 160° C., for example, above about 80° C. to about 260° C.

In some embodiments, the PVA-PAA-hydrogel is heated in air or inert gas or partial vacuum of inert gas for dehydration.

In some of these embodiments, the PVA-PAA-hydrogel is vacuum dehydrated before heating in air or inert gas.

In some embodiments, the heating of the PVA-PAA-hydrogel is carried out slowly; for example at less than about 1° C./min, at more than about 1° C./min, at 2, 5, 10° C./min or faster. Slower heating rates results in stronger gels than higher heating rates with some of the PVA-hydrogel formulations.

In most embodiments the finished medical device is packaged and sterilized.

In some of the embodiments the hydrogel is subjected to dehydration steps. The dehydration is carried out in air or in vacuum or at an elevated temperature (for instance heating at above or below 160° C., for example, above about 80° C. to about 260° C.). The dehydration causes loss of water hence a reduction in volume accompanied by a reduction in weight. The weight loss is due to loss of water. The reduction in volume on the other hand could be due to the loss of water or further crystallization of the hydrogel. In some embodiments the dehydration is carried out by placing the hydrogel in a low molecular weight polymer (for instance placing a PVA-PAA-hydrogel in a PEG solution). In some cases the dehydration is caused by loss of water, but in most cases, there is also uptake of the non-solvent by the hydrogel. Therefore, the weight change of the hydrogel is the sum of loss of water and uptake of the non-solvent. The change in volume in this case is due to loss of water, uptake of the non-solvent, further crystallization of the hydrogel, or partial collapse of the porous structure of the non-solvent that is not occupying the space that water was filling in the pores.

In some of the embodiments, the hydrogel is attached to a metal piece. The metal piece is a porous backside surface that is used for bone-in-growth in the body to fix the hydrogel implant in place. The metal piece attachment to the hydrogel can be achieved by having a porous surface on the substrate where it makes contact with the hydrogel; the porous surface can be infiltrated by the gelling hydrogel solution (for instance a hot PVA-PAA and/or PEG mixture in water); when the solution forms a hydrogel, the hydrogel can be interconnected with the metal piece by filling the porous space.

In some embodiments, there can be more than one metal piece attached to the hydrogel for fixation with the hydrogel in the body to multiple locations.

In some embodiments, the hydrogel/metal piece construct can be used during the processing steps described above, such as solvent dehydration, non-solvent dehydration, irradiation, packaging, sterilization, and the like.

In some of the embodiments the hydrogel contains hyaluronic acid (HA), either by having HA present in the solutions used to make the hydrogel and/or by diffusing HA into the hydrogel. In some of the embodiments the HA-containing hydrogel is irradiated. The irradiation can be carried out before, after, or during the processing steps such as vacuum dehydration, non-solvent dehydration, re-hydration, and/or heating. The irradiation cross-links the hydrogel matrix and in some embodiments also forms covalent bonds with the HA. Addition HA to some of the hydrogels increases the lubricity of the hydrogel implant. It can be beneficial for the PVA-PAA-hydrogels to contain substantially reduced water content.

In some embodiments, the hydrated hydrogel implants are slightly heated at the surface to partially melt the hydrogel and allow it to reform with more uptake and lubricity.

In some embodiments, a microwave oven can be used to prepare the PVA solution. The PVA powder is place in water and the mixture is heated in a microwave oven to form a solution.

In some of the embodiments the heat dehydration or heating of the hydrogel is carried out in a microwave oven.

According to one embodiment of the invention, PVA-PAA-gel is prepared by a process comprising the steps of: providing polymeric material such as PVA powder; mixing with water at temperature above the room temperature (such as at about 50° C.-60° C.), thereby forming a solution; subjecting the solution to at least one freeze-thaw cycle or heating to a temperature below the melting temperature such as about 80° C.; cooling the heated solution to an ambient temperature such as room temperature, thereby forming a hydrogel (which is generally uniform, may also contain hydrogel particles); and/or dehydrating the hydrogel, thereby forming the PVA-PAA-hydrogel.

Embodiments and aspects of the invention also include:

1. PVA-hydrogels that are capable of re-hydration following dehydration, wherein the PVA-hydrogel is capable of re-hydration following dehydration, wherein a) the dehydration reduces the weight of the hydrogel, for example, by more than about 34%; and b) the re-hydration results increase in equilibrium water content in the re-hydrated hydrogel, for example, at least about 46%.

2. PVA-hydrogels with biaxial orientation.

3. PVA-hydrogels with uniaxial orientation.

4. PVA-hydrogels with a high ultimate tensile strength.

5. Dehydration of a PVA-hydrogel containing water and/or one or more other ingredients (for example, PEG or Salt), wherein a. the ingredient is non-volatile such as PEG;

b. the ingredient is at least partially miscible with water;

c. at least 0.1% of the hydrogel's weight constitutes one or more non-volatile ingredients, such as PEG, hydrocarbons, and the like;

d. the ingredients are water miscible polymer such as PEO, Pluronic, amino acids, proteoglycans, polyvinylpyrrolidone, polysaccharides, dermatin sulfate, keratin sulfate, chondroitin sulfate, dextran sulfate, and the like;

e. the ingredient is selected from the group of PEG, salt, NaCl, KCl, $CaCl_2$, vitamins, carboxylic acids, hydrocarbons, esters, amino acids, and the like;

f. the ingredient is PEG, wherein i. PEG of different molecular weights, or ii. blends of PEGs, g. the dehydration is carried out by placing in a non-solvent, wherein i. the non-solvent is selected from PEG, alcohols (such as isopropyl alcohol), acetones, saturated salinated water, aqueous solution of a salt of an alkali metal, vitamins, carboxylic acids, and the like, or ii. the non-solvent contains more than one ingredients such as water, PEG, vitamins, polymers, proteoglycans, carboxylic acids, esters, and the like.

h. the dehydration is carried out by leaving the hydrogel in air;
i. the dehydration is carried out by placing the hydrogel in vacuum;
j. the dehydration is carried out by placing the hydrogel in vacuum at room temperature;
k. the dehydration is carried out by placing the hydrogel in vacuum at an elevated temperature;
l. the dehydration is carried out by heating the hydrogel in air or inert gas to elevated temperature, wherein
  i. the heating rate is slow,
  ii. the heating rate is fast, or
  iii. the heating follows the vacuum or air dehydration; and
m. the dehydrated hydrogel is re-hydrated
  i. by placing in water, saline solution, Ringer's solution, salinated water, buffer solution, and the like,
  ii. by placing in a relative humidity chamber, or
  iii. by placing at room temperature or at an elevated temperature.

Each composition and attendant aspects, and each method and attendant aspects, which are described above can be combined with another in a manner consistent with the teachings contained herein. According to the embodiments of the inventions, all methods and the steps in each method can be applied in any order and repeated as many times in a manner consistent with the teachings contained herein.

DEFINITIONS

The term "supercritical fluid" refers to what is known in the art, for example, supercritical propane, acetylene, carbon dioxide ($CO_2$). In this connection the critical temperature is that temperature above which a gas cannot be liquefied by pressure alone. The pressure under which a substance may exist as a gas in equilibrium with the liquid at the critical temperature is the critical pressure. Supercritical fluid condition generally means that the fluid is subjected to such a temperature and such a pressure that a supercritical fluid and thereby a supercritical fluid mixture is obtained, the temperature being above the supercritical temperature, which for $CO_2$ is 31.3° C., and the pressure being above the supercritical pressure, which for $CO_2$ is 73.8 bar.

The term "heating" refers to thermal treatment of the polymer at or to a desired heating temperature. In one aspect, heating can be carried out at a rate of about 10° C. per minute to the desired heating temperature. In another aspect, the heating can be carried out at the desired heating temperature for desired period of time. In other words, heated polymers can be annealed or continued to heat at the desired temperature for a desired period of time. Heating time at or to a desired heating temperature can be at least 1 minute to 48 hours to several weeks long. In one aspect the heating time is about 1 hour to about 24 hours. Heating temperature refers to the thermal condition for heating in accordance with the invention.

The term "annealing" refers to heating the hydrogels below its peak melting point. Annealing time can be at least 1 minute to several days long. In one aspect the annealing time is about 4 hours to about 48 hours, preferably 24 to 48 hours and more preferably about 24 hours. "Annealing temperature" refers to the thermal condition for annealing in accordance with the invention. In certain embodiments, the term "annealing" refer as a type of thermal treatment.

At any step of manufacture, the hydrogel can be irradiated by e-beam or gamma to cross-link. The irradiation can be carried out in air, in inert gas, in sensitizing gas, or in a fluid medium such as water, saline solution, polyethylene-glycol solution, and the like. The radiation dose level is between one kGy and 10,000 kGy, preferably 25 kGy, 40 kGy, 50 kGy, 200 kGy, 250 kGy, or above.

The terms "about" or "approximately" in the context of numerical values and ranges refers to values or ranges that approximate or are close to the recited values or ranges such that the invention can perform as intended, such as having a desired degree of cross-linking, creep resistance, lubricity and/or toughness, as is apparent to the skilled person from the teachings contained herein. This is due, at least in part, to the varying properties of polymer compositions. Thus these terms encompass values beyond those resulting from systematic error. These terms make explicit what is implicit.

"Irradiation", in one aspect of the invention, the type of radiation, preferably ionizing, is used. According to another aspect of the invention, a dose of ionizing radiation ranging from about 25 kGy to about 1000 kGy is used. The radiation dose can be about 25 kGy, about 50 kGy, about 65 kGy, about 75 kGy, about 100 kGy, about 150, kGy, about 200 kGy, about 300 kGy, about 400 kGy, about 500 kGy, about 600 kGy, about 700 kGy, about 800 kGy, about 900 kGy, or about 1000 kGy, or above 1000 kGy, or any value thereabout or therebetween. Preferably, the radiation dose can be between about 25 kGy and about 150 kGy or between about 50 kGy and about 100 kGy. These types of radiation, including gamma and/or electron beam, kills or inactivates bacteria, viruses, or other microbial agents potentially contaminating medical implants, including the interfaces, thereby achieving product sterility. The irradiation, which may be electron or gamma irradiation, in accordance with the present invention can be carried out in air atmosphere containing oxygen, wherein the oxygen concentration in the atmosphere is at least 1%, 2%, 4%, or up to about 22%, or any value thereabout or therebetween. In another aspect, the irradiation can be carried out in an inert atmosphere, wherein the atmosphere contains gas selected from the group consisting of nitrogen, argon, helium, neon, or the like, or a combination thereof. The irradiation also can be carried out in a sensitizing gas such as acetylene or mixture or a sensitizing gas with an inert gas or inert gases. The irradiation also can be carried out in a vacuum. The irradiation can also be carried out at room temperature, or at between room temperature and the melting point of the polymeric material, or at above the melting point of the polymeric material. Subsequent to the irradiation step the hydrogel can be melted or heated to a temperature below its melting point for annealing. These post-irradiation thermal treatments can be carried out in air, PEG, solvents, non-solvents, inert gas and/or in vacuum. Also the irradiation can be carried out in small increments of radiation dose and in some embodiments these sequences of incremental irradiation can be interrupted with a thermal treatment. The sequential irradiation can be carried out with about 1, 10, 20, 30, 40, 50, 100 kGy, or higher radiation dose increments. Between each or some of the increments the hydrogel can be thermally treated by melting and/or annealing steps. The thermal treatment after irradiation is mostly to reduce or to eliminate the residual free radicals in the hydrogels created by irradiation, and/or eliminate the crystalline matter, and/or help in the removal of any extractables that may be present in the hydrogel.

In accordance with another aspect of this invention, the irradiation may be carried out in a sensitizing atmosphere. This may comprise a gaseous substance which is of sufficiently small molecular size to diffuse into the polymer and which, on irradiation, acts as a polyfunctional grafting moiety. Examples include substituted or unsubstituted polyunsaturated hydrocarbons; for example, acetylenic hydrocarbons such as acetylene; conjugated or unconjugated olefinic hydrocarbons such as butadiene and (meth)acrylate monomers; sulphur monochloride, with chloro-tri-fluoroethylene (CTFE) or acetylene being particularly preferred. By "gaseous" is meant herein that the sensitizing atmosphere is in the gas phase, either above or below its critical temperature, at the irradiation temperature.

"Metal Piece", in accordance with the invention, the piece forming an interface with polymeric material is, for example, a metal. The metal piece in functional relation with polymeric material, according to the present invention, can be made of a cobalt chrome alloy, stainless steel, titanium, titanium alloy or nickel cobalt alloy, for example.

"Non-metallic Piece", in accordance with the invention, the piece forming an interface with polymeric material is, for example, a non-metal. The non-metal piece in functional relation with polymeric material, according to the present invention, can be made of ceramic material, for example.

An atmosphere or an environment that refers to or includes "air" will have a mixture of reactive and inert gases. Air contains nitrogen, oxygen, $CO_2$, traces of other gases, including other inert gases (for example, noble gases), water vapor, etc.

An inert atmosphere refers to an environment that contains one or more inert gases (for example, nitrogen, argon, helium, or neon) of sufficient purity that the atmosphere is inert and gases of such purity are commercially available. An "inert atmosphere" or "inert environment" typically has no more than about 1% oxygen and more preferably, provides a condition that allows free radicals in polymeric materials to form cross links without problematic oxidation during sterilization. An inert atmosphere is used to avoid some deleterious effects of $O_2$, which could, depending on conditions, cause problematic oxidation of the device. Inert gasses, such as nitrogen, argon, helium, or neon, can be used when sterilizing polymeric medical implants with ionizing radiation.

Inert atmospheric conditions such as nitrogen, argon, helium, neon, or vacuum are also used for sterilizing interfaces of in medical implants by ionizing radiation.

Inert conditions also can refer to use of an inert fluid, inert gas, or inert liquid medium, such as silicon oil.

The term "vacuum" refers to an environment having no appreciable amount of gas. A vacuum is used to avoid $O_2$. A vacuum condition can be used for sterilizing implants by ionizing radiation. A vacuum condition can be created using a commercially available vacuum pump. A vacuum condition also can be used when sterilizing interfaces in medical implants by ionizing radiation.

"Sterilization", one aspect of the present invention discloses a process of sterilization of medical implants containing PVA-hydrogels, such as PVA-PAA-hydrogels. The process comprises sterilizing the medical implants by ionizing sterilization with gamma or electron beam radiation, for example, at a dose level ranging from about 25-70 kGy, or by gas sterilization with ethylene oxide or gas plasma.

Another aspect of the present invention discloses a process of sterilization of medical implants containing PVA-hydrogels, such as PVA-PAA-hydrogels. The process comprises sterilizing the medical implants by ionizing sterilization with gamma or electron beam radiation, for example, at a dose level ranging from 25-200 kGy. The dose level of sterilization is higher than standard levels used in irradiation. This is to allow cross-linking or further cross-linking of the medical implants during sterilization.

The term "contact" includes physical proximity with or touching, mixing or blending of one ingredient with another. For example, a PVA solution in contacted with a PAA solution.

The term "hydrogel" or the term "PVA-hydrogels", as described herein, encompasses all PVA-based hydrogels, "PVA-PAA-hydrogels", "PVA-PAA-PEG-hydrogels", "PVA-PEG-PAA-hydrogels" and all other hydrogel compositions disclosed herein, including de-hydrated hydrogels. PVA-hydrogels are networks of hydrophilic polymers containing absorbed water that can absorb a large amounts of energy, such as mechanical energy, before failure.

The term "creep resistance" (adj. creep resistant) generally refers to the resistance to continued extension or deformation, which results from the viscoelastic flow of the polymer chains under continuous load.

The term "lubricity" (adj. lubricious) generally refers to a physical properties of a hydrogel, for example, it is a measure of the slipperiness of a hydrogel surface, which also relates to the hydrophilicity of the same surface.

Each composition and attendant aspects, and each method and attendant aspects, which are described above can be combined with another in a manner consistent with the teachings contained herein. According to the embodiments of the inventions, all methods and the steps in each method can be applied in any order and repeated as many times in a manner consistent with the teachings contained herein.

The invention is further described by the following examples, which do not limit the invention in any manner.

EXAMPLES

Determination of the Equilibrium Water Content (EWC) in a Hydrogel

Following method was used to determine the equilibrium water content (EWC) in a hydrogel. The specimens were first immersed in saline solution with agitation for removal of any unbound molecules and for equilibrium hydration. To determine when the gels reached equilibrium hydration, their weight changes were recorded daily and the saline solution was replaced with fresh saline solution. After the equilibrium hydration level was reached, the equilibrium hydration weights of the specimens were recorded. Subsequently, the gel specimens were dried in an air convection oven at 90° C. until no significant changes in weight were detected. The EWC in a gel was then calculated by the ratio of the difference between the hydrated and dehydrated weights to the weight at equilibrated hydration state.

Example 1

15% Total Polymer of 7:3 PVA:PAA Ratio with 15% PEG; 3 Freeze-Thaw Cycles

PVA (MW=115,000 g/mol (99.7% hydrolyzed), Scientific Polymer Products, Ontario, N.Y.) was mixed into an aqueous solution of PAA (MW=200,000 g/mol, Polysciences) at 90° C. to form a homogenous PVA-PAA solution. The PVA:PAA ratio was 7:3 with 15 w/w % total polymer content in the blend. Subsequently, pre-heated polyethylene glycol (MW=400) (PEG400) of 15 w/w % of PEG with respect to the total PEG and water amount in the mixture was added to the solution with vigorous mechanical stirring at 90° C. to form a homogenous PVA-PAA-PEG solution. Resulting clear solution was degassed to remove air bubbles and poured into a hot glass mold and sealed with a glass cover. This mold was kept between two stainless steel blocks that were previously heated to 90° C. The mold then was placed in a −17° C. freezer for 16 hours, and subsequently thawed at room temperature for 8 hours. This process completed one cycle of freeze-thaw procedure. Upon completion of 3 freeze-thaw cycles, the resulting hydrogel sheet was removed from the mold and immersed in saline until equilibrium re-hydration. The equilibrium water content of the final gel was 89.63±0.17%.

Example 2

15% Total Polymer of 7:3 PVA:PAA Ratio with 15% PEG; 3 Freeze-Thaw Cycles; Vacuum-Dehydrated

PVA (MW=115,000 g/mol (99.7% hydrolyzed), Scientific Polymer Products, Ontario, N.Y.) was mixed into an aqueous solution of PAA (MW=200,000 g/mol, Polysciences) at 90° C. to form a homogenous PVA-PAA solution. The PVA:PAA ratio was 7:3 with 15 w/w % total polymer content in the blend. Subsequently, pre-heated polyethylene glycol (MW=400) (PEG400) of 15 w/w % of PEG with respect to the total PEG and water amount in the mixture was added to the solution with vigorous mechanical stirring at 90° C. to form a homogenous PVA-PAA-PEG solution. Resulting clear solution was degassed to remove air bubbles and poured into a hot glass mold and sealed with a glass cover. This mold was kept between two stainless steel blocks that were previously heated to 90° C. The mold then was placed in a −17° C. freezer for 16 hours, and subsequently thawed at room temperature for 8 hours. This process completed one cycle of freeze-thaw procedure. Upon completion of 3 freeze-thaw cycles, the resulting hydrogel sheet was removed from the mold and dehydrated under vacuum at room temperature until the weight changes of the hydrogel due to dehydration reached equilibrium. The vacuum-dehydrated gel was then immersed in saline until equilibrium re-hydration. The equilibrium water content of the final gel was 89.17±0.11%.

Example 3

15% Total Polymer of 7:3 PVA:PAA Ratio with 15% PEG; 3 Freeze-Thaw Cycles; Vacuum-Dehydrated; Heated

PVA (MW=115,000 g/mol (99.7% hydrolyzed), Scientific Polymer Products, Ontario, N.Y.) was mixed into an aqueous solution of PAA (MW=200,000 g/mol, Polysciences) at 90° C. to form a homogenous PVA-PAA solution. The PVA:PAA ratio was 7:3 with 15 w/w % total polymer content in the blend. Subsequently, pre-heated polyethylene glycol (MW=400) (PEG400) of 15 w/w % of PEG with respect to the total PEG and water amount in the mixture was added to the solution with vigorous mechanical stirring at 90° C. to form a homogenous PVA-PAA-PEG solution. Resulting clear solution was degassed to remove air bubbles and poured into a hot glass mold and sealed with a glass cover. This mold was kept between two stainless steel blocks that were previously heated to 90° C. The mold then was placed in a −17° C. freezer for 16 hours, and subsequently thawed at room temperature for 8 hours. This process completed one cycle of freeze-thaw procedure. Upon completion of 3 freeze-thaw cycles, the resulting hydrogel sheet was removed from the mold and dehydrated under vacuum at room temperature until the weight changes of the hydrogel due to dehydration reached equilibrium. After vacuum dehydration, the hydrogel specimen was heated at 160° C. in an argon-filled closed chamber already heated to 160° C. for one hour. The heated gel was then immersed in saline until equilibrium re-hydration. The equilibrium water content of the final gel was 72.93±1.04%.

Figure 1:
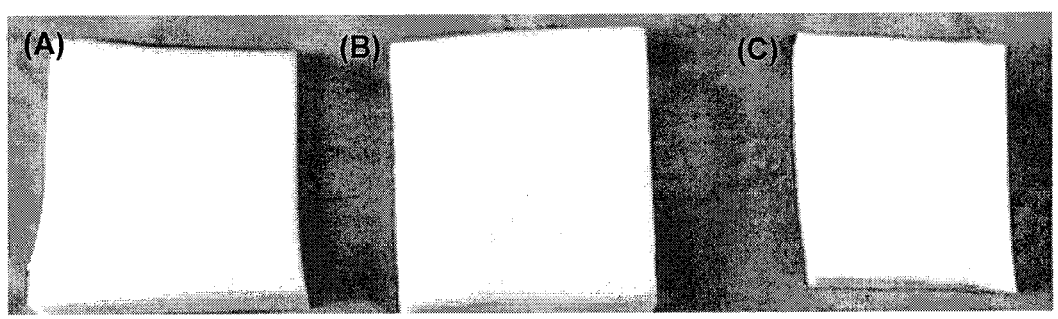
FIG. 1 shows the PVA-PAA hydrogels formed from 15% solid PVA-PAA-PEG blends with 15% PEG by 3 cycle freeze-thawing after various processing described in Examples 1-3: 1(A) After re-hydration in saline (Example 1), 1(B) After vacuum dehydration followed by re-hydration in saline (Example 2), and 1(C) After vacuum dehydration and subsequent heating followed by re-hydration in saline (Example 3).

The PVA-PAA hydrogels formed from 15% solid PVA-PAA-PEG blends with 15% PEG by 3 cycle freeze-thawing after various processing described in Examples 1-3 are shown in FIG. 1, as FIG. 1(A) After re-hydration in saline (Example 1), FIG. 1(B) After vacuum dehydration followed by re-hydration in saline (Example 2), and FIG. 1(C) After vacuum dehydration and subsequent heating followed by re-hydration in saline (Example 3).

Example 4

15% Total Polymer of 7:3 PVA:PAA Ratio with 15% PEG; 3 Freeze-Thaw Cycles; dePEGed; Vacuum-Dehydrated; Heated

PVA (MW=115,000 g/mol (99.7% hydrolyzed), Scientific Polymer Products, Ontario, N.Y.) was mixed into an aqueous solution of PAA (MW=200,000 g/mol, Polysciences) at 90° C. to form a homogenous PVA-PAA solution. The PVA:PAA ratio was 7:3 with 15 w/w % total polymer content in the blend. Subsequently, pre-heated polyethylene glycol (MW=400) (PEG400) of 15 w/w % of PEG with respect to the total PEG and water amount in the mixture was added to the solution with vigorous mechanical stirring at 90° C. to form a homogenous PVA-PAA-PEG solution. Resulting clear solution was degassed to remove air bubbles and poured into a hot glass mold and sealed with a glass cover. This mold was kept between two stainless steel blocks that were previously heated to 90° C. The mold then was placed in a −17° C. freezer for 16 hours, and subsequently thawed at room temperature for 8 hours. This process completed one cycle of freeze-thaw procedure. Upon completion of 3 freeze-thaw cycles, the hydrogel was removed from the mold and placed in a saline solution for "dePEGing" process, which removes the residual PEG in the gel by exchanging with water during re-hydration in saline. The dePEGed PVA-PAA gel was then dehydrated under vacuum at room temperature until the weight changes of the hydrogel due to dehydration reached equilibrium. After vacuum dehydration, the hydrogel specimen was heated at 160° C. in an argon-filled closed chamber already heated to 160° C. for one hour. The heated gel was then immersed in saline until equilibrium re-hydration. The equilibrium water content of the final processed gel was 42.40±0.48%.

Table 1 shows the weight changes and equilibrium water content (EWC) of PVA-PAA hydrogels formed from 15% solid PVA-PAA-PEG blends with 15% PEG by 3 cycle freeze-thawing at each stage of processing from Examples 1-4.

TABLE 1

Weight changes and equilibrium water content (EWC) of PVA-PAA-hydrogels.

| Measurements made | Weight Changes with respect to the as-gelled state (%) | EWC (%) |
| --- | --- | --- |
| As-gelled | 0.0 | Not measured |
| After re-hydration in saline (Example 1) | 13.93 | 89.63 ± 0.17 |
| After vacuum dehydration | −72.73 | Not measured |
| After vacuum dehydration followed by re-hydration in saline (Example 2) | 14.93 | 89.17 ± 0.11 |

TABLE 1-continued

Weight changes and equilibrium water content (EWC) of PVA-PAA-hydrogels.

| Measurements made | Weight Changes with respect to the as-gelled state (%) | EWC (%) |
|---|---|---|
| After vacuum dehydration and subsequent heating | −72.72 | Not measured |
| After vacuum dehydration and subsequent heating followed by re-hydration in saline (Example 3) | −49.03 | 72.93 ± 1.04 |
| After dePEGing in saline and subsequent vacuum dehydration | −86.79 | Not measured |
| After dePEGing in saline and subsequent vacuum dehydration and heating | −87.36 | Not measured |
| After dePEGing in saline and subsequent vacuum dehydration and heating followed by re-hydration in saline (Example 4) | −80.66 | 42.20 ± 0.48 |

Table 1 also shows that in the presence of PEG, heating only reduced the EWC to 73%, whereas in the absence of PEG, the reduction was much higher (EWC=42%). PEG protected the pores from collapsing during the thermal treatment.

Example 5

15% Total Polymer of 7:3 PVA:PAA Ratio with No PEG; 3 Freeze-Thaw Cycles

PVA (MW=115,000 g/mol (99.7% hydrolyzed), Scientific Polymer Products, Ontario, N.Y.) was mixed into an aqueous solution of PAA (MW=200,000 g/mol, Polysciences) at 90° C. to form a homogenous PVA-PAA solution. The PVA:PAA ratio was 7:3 with 15 w/w % total polymer content in the blend. Resulting clear solution was degassed to remove air bubbles and poured into a hot glass mold and sealed with a glass cover. This mold was kept between two stainless steel blocks that were previously heated to 90° C. The mold then was placed in a −17° C. freezer for 16 hours, and subsequently thawed at room temperature for 8 hours. This process completed one cycle of freeze-thaw procedure. Upon completion of 3 freeze-thaw cycles, the resulting hydrogel sheet was removed from the mold and immersed in saline until equilibrium re-hydration. The equilibrium water content of the final processed gel was 84.11±6.77%.

Example 6

15% Total Polymer of 7:3 PVA:PAA Ratio with No PEG; 3 Freeze-Thaw Cycles; Vacuum-Dehydrated PVA (MW=115,000 g/mol (99.7% hydrolyzed), Scientific Polymer Products, Ontario, N.Y.) was mixed into an aqueous solution of PAA (MW=200,000 g/mol, Polysciences) at 90° C. to form a homogenous PVA-PAA solution. The PVA:PAA ratio was 7:3 with 15 w/w % total polymer content in the blend. Resulting clear solution was degassed to remove air bubbles and poured into a hot glass mold and sealed with a glass cover. This mold was kept between two stainless steel blocks that were previously heated to 90° C. The mold then was placed in a −17° C. freezer for 16 hours, and subsequently thawed at room temperature for 8 hours. This process completed one cycle of freeze-thaw procedure. Upon completion of 3 freeze-thaw cycles, the resulting hydrogel sheet was removed from the mold and dehydrated under vacuum at room temperature until the weight changes of the hydrogel due to dehydration reached equilibrium. After vacuum dehydration, the gel was immersed in saline until equilibrium re-hydration. The equilibrium water content of the final processed gel was 73.98±0.14%.

Example 7

15% Total Polymer of 7:3 PVA:PAA Ratio with No PEG; 3 Freeze-Thaw Cycles; Vacuum-Dehydrated; Heated PVA (MW=115,000 g/mol (99.7% hydrolyzed), Scientific Polymer Products, Ontario, N.Y.) was mixed into an aqueous solution of PAA (MW=200,000 g/mol, Polysciences) at 90° C. to form a homogenous PVA-PAA solution. The PVA:PAA ratio was 7:3 with 15 w/w % total polymer content in the blend. Resulting clear solution was degassed to remove air bubbles and poured into a hot glass mold and sealed with a glass cover. This mold was kept between two stainless steel blocks that were previously heated to 90° C. The mold then was placed in a −17° C. freezer for 16 hours, and subsequently thawed at room temperature for 8 hours. This process completed one cycle of freeze-thaw procedure. Upon completion of 3 freeze-thaw cycles, the resulting hydrogel sheet was removed from the mold and dehydrated under vacuum at room temperature until the weight changes of the hydrogel due to dehydration reached equilibrium. After vacuum dehydration, the hydrogel specimen was heated at 160° C. in an argon-filled closed chamber already heated to 160° C. for one hour. The heated gel was then immersed in saline until equilibrium re-hydration. The equilibrium water content of the final processed gel was 36.50±0.37%.

Example 8

15% Total Polymer of 7:3 PVA:PAA Ratio with No PEG; 3 Freeze-Thaw Cycles; PEG400-Immersed PVA (MW=115,000 g/mol (99.7% hydrolyzed), Scientific Polymer Products, Ontario, N.Y.) was mixed into an aqueous solution of PAA (MW=200,000 g/mol, Polysciences) at 90° C. to form a homogenous PVA-PAA solution. The PVA:PAA ratio was 7:3 with 15 w/w % total polymer content in the blend. Resulting clear solution was degassed to remove air bubbles and poured into a hot glass mold and sealed with a glass cover. This mold was kept between two stainless steel blocks that were previously heated to 90° C. The mold then was placed in a −17° C. freezer for 16 hours, and subsequently thawed at room temperature for 8 hours. This process completed one cycle of freeze-thaw procedure. Upon completion of 3 freeze-thaw cycles, the resulting hydrogel sheet was removed from the mold and immersed in 100% PEG400 with agitation until the weight changes of the hydrogel due to PEG immersion reached equilibrium. Subsequently, the PEG-dehydrated PVA-PAA gel was immersed in saline until equilibrium re-hydration. The equilibrium water content of the final processed gel was 85.54±0.11%.

Figure 2:
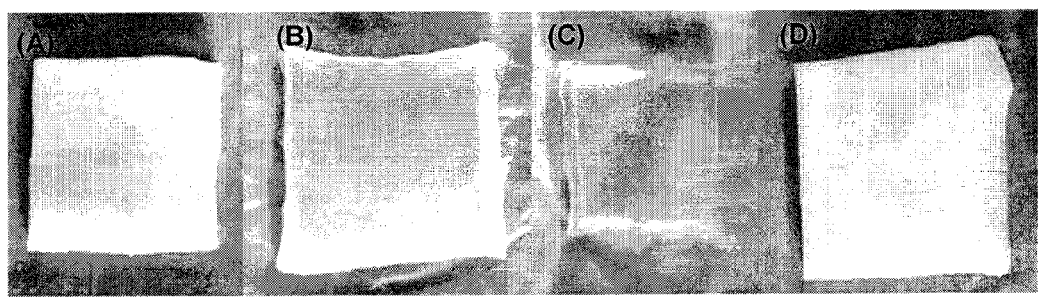
FIG. 2 depicts the PVA-PAA hydrogels formed from 15% solid PVA-PAA blends by 3 cycle freeze-thawing after various processing described in Examples 5-8: 2(A) After re-hydration in saline (Example 5), 2(B) After vacuum dehydration followed by re-hydration in saline (Example 6), 2(C) After vacuum dehydration and subsequent heating followed by re-hydration in saline (Example 7), and 2(D) After immersing in 100% PEG400 followed by re-hydration in saline (Example 8).

The PVA-PAA hydrogels formed from 15% solid PVA-PAA blends by 3 cycle freeze-thawing after various processing described in Examples 5-8 are shown in FIG. 2, as FIG. 2(A) After re-hydration in saline (Example 5), FIG. 2(B) After vacuum dehydration followed by re-hydration in saline (Example 6), FIG. 2(C) After vacuum dehydration and subsequent heating followed by re-hydration in saline (Example 7), and FIG. 2(D) After immersing in 100% PEG400 followed by re-hydration in saline (Example 8).

Example 9

15% Total Polymer of 7:3 PVA:PAA Ratio with No PEG; 3 Freeze-Thaw Cycles; PEG400-Immersed; Vacuum-Dehydrated PVA (MW=115,000 g/mol (99.7% hydrolyzed), Scientific Polymer Products, Ontario, N.Y.) was mixed into an aqueous solution of PAA (MW=200,000 g/mol, Polysciences) at 90° C. to form a homogenous PVA-PAA solution. The PVA:PAA ratio was 7:3 with 15 w/w % total polymer content in the blend. Resulting clear solution was degassed to remove air bubbles and poured into a hot glass mold and sealed with a glass cover. This mold was kept between two stainless steel blocks that were previously heated to 90° C. The mold then was placed in a −17° C. freezer for 16 hours, and subsequently thawed at room temperature for 8 hours. This process completed one cycle of freeze-thaw procedure. Upon completion of 3 freeze-thaw cycles, the resulting hydrogel sheet was removed from the mold and immersed in 100% PEG400 with agitation until the weight changes of the hydrogel reached equilibrium. Subsequently, the PEG-doped PVA-PAA gel was dehydrated under vacuum at room temperature. After vacuum dehydration, the gel was immersed in saline until equilibrium re-hydration. The equilibrium water content of the final processed gel was 83.81%.

Example 10

15% Total Polymer of 7:3 PVA:PAA Ratio with No PEG; 3 Freeze-Thaw Cycles; PEG400-Immersed; Vacuum-Dehydrated; Heated PVA (MW=115,000 g/mol (99.7% hydrolyzed), Scientific Polymer Products, Ontario, N.Y.) was mixed into an aqueous solution of PAA (MW=200,000 g/mol, Polysciences) at 90° C. to form a homogenous PVA-PAA solution. The PVA:PAA ratio was 7:3 with 15 w/w % total polymer content in the blend. Resulting clear solution was degassed to remove air bubbles and poured into a hot glass mold and sealed with a glass cover. This mold was kept between two stainless steel blocks that were previously heated to 90° C. The mold then was placed in a −17° C. freezer for 16 hours, and subsequently thawed at room temperature for 8 hours. This process completed one cycle of freeze-thaw procedure. Upon completion of 3 freeze-thaw cycles, the resulting hydrogel sheet was removed from the mold and immersed in 100% PEG400 with agitation until the weight changes of the hydrogel reached equilibrium. Subsequently, the PEG-doped PVA-PAA gel was dehydrated under vacuum at room temperature. After vacuum dehydration, the gel was heated at 160° C. in an argon-filled closed chamber already heated to 160° C. for one hour. The heated gel was then immersed in saline until equilibrium re-hydration. The equilibrium water content of the final processed gel was 69.34±1.28%.

Table 2 shows the weight changes and equilibrium water content (EWC) of PVA-PAA hydrogels formed from 15% solid PVA-PAA blends by 3 cycle freeze-thawing at each stage of processing from Examples 5-10.

TABLE 2

Weight changes and equilibrium water content (EWC) of PVA-PAA-hydrogels.

| Measurements made | Weight Changes (%) | EWC (%) |
|---|---|---|
| As-gelled | 0.0 | Not measured |
| After re-hydration in saline (Example 5) | 5.25 | 84.11 ± 6.77 |
| After vacuum dehydration | −83.61 | Not measured |
| After vacuum dehydration followed by re-hydration in saline (Example 6) | −45.36 | 73.98 ± 0.14 |
| After vacuum dehydration and subsequent heating | −83.49 | Not measured |
| After vacuum dehydration and subsequent heating followed by re-hydration in saline (Example 7) | −76.63 | 36.50 ± 0.37 |
| After immersing in 100% PEG400 | −61.23 | Not measured |
| After immersing in 100% PEG400 followed by re-hydration in saline (Example 8) | −13.13 | 85.54 ± 0.11 |
| After immersing in 100% PEG400 and subsequent vacuum dehydration | −62.61 | Not measured |
| After immersing in 100% PEG400 and subsequent vacuum dehydration followed by re-hydration in saline (Example 9) | −16.40 | 83.81 |
| After immersing in 100% PEG400 and subsequent vacuum dehydration and heating | −65.57 | Not measured |
| After immersing in 100% PEG400 and subsequent vacuum dehydration and heating followed by re-hydration in saline (Example 10) | −48.51 | 69.34 ± 1.04 |

As observed in Examples 1-4, when present, PEG protected the pores from collapsing during the thermal treatment.

Example 11

30% Total Polymer of 7:3 PVA:PAA Ratio with 15% PEG; Room Temp Gelling; Vacuum-Dehydrated PVA (MW=115,000 g/mol (99.7% hydrolyzed), Scientific Polymer Products, Ontario, N.Y.) was mixed into an aqueous solution of PAA (MW=50,000 g/mol, Polysciences) at 90° C. to form a homogenous PVA-PAA solution. The PVA:PAA ratio was 7:3 with 30 w/w % total polymer content in the blend. Subsequently, pre-heated polyethylene glycol (MW=400) (PEG400) of 15 w/w % of PEG with respect to the total PEG and water amount in the mixture was added to the solution with vigorous mechanical stirring at 90° C. to form a homogenous PVA-PAA-PEG solution. The resulting clear solution was degassed to remove air bubbles and poured into a hot glass mold and sealed with a glass cover. This mold was kept between two stainless steel blocks that were previously heated to 90° C. The mold then was slowly cooled down to room temperature for 24 hours. Upon gelling, the resulting hydrogel sheet was removed from the mold and dehydrated under vacuum at room temperature. After vacuum dehydration, the gel was immersed in saline until equilibrium re-hydration. The equilibrium water content of the final processed gel was 74.57±0.32%.

Example 12

30% Total Polymer of 7:3 PVA:PAA Ratio with 15% PEG; Room Temperature Gelling; Vacuum-Dehydrated; Heated PVA (MW=115,000 g/mol (99.7% hydrolyzed), Scientific Polymer Products, Ontario, N.Y.) was mixed into an aqueous solution of PAA (MW=50,000 g/mol, Polysciences) at 90° C. to form a homogenous PVA-PAA solution. The PVA:PAA ratio was 7:3 with 30 w/w % total polymer content in the blend. Subsequently, pre-heated polyethylene glycol (MW=400) (PEG400) of 15 w/w % of PEG with respect to the total PEG and water amount in the mixture was added to the solution with vigorous mechanical stirring at 90° C. to form a homogenous PVA-PAA-PEG solution. Resulting clear solution was degassed to remove air bubbles and poured into a hot glass mold and sealed with a glass cover. This mold was kept between two stainless steel blocks that were previously heated to 90° C. The mold then was slowly cooled down to room temperature for 24 hours. Upon gelling, the resulting hydrogel sheet was removed from the mold and dehydrated under vacuum at room temperature. After vacuum dehydration, the gel was heated at 160° C. in an argon-filled closed chamber already heated to 160° C. for one hour. The heated gel was then immersed in saline until equilibrium re-hydration. The equilibrium water content of the final processed gel was 57.66±1.40%.

Example 13

27% Total Polymer of 7:3 PVA:PAA Ratio with 15% PEG; Room Temp Gelling; Vacuum-Dehydrated PVA (MW=115,000 g/mol (99.7% hydrolyzed), Scientific Polymer Products, Ontario, N.Y.) was mixed into an aqueous solution of PAA (MW=200,000 g/mol, Polysciences) at 90° C. to form a homogenous PVA-PAA solution. The PVA:PAA ratio was 7:3 with 27 w/w % total polymer content in the blend. Subsequently, pre-heated polyethylene glycol (MW=400) (PEG400) of 15 w/w % of PEG with respect to the total PEG and water amount in the mixture was added to the solution with vigorous mechanical stirring at 90° C. to form a homogenous PVA-PAA-PEG solution. Resulting clear solution was degassed to remove air bubbles and poured into a hot glass mold and sealed with a glass cover. This mold was kept between two stainless steel blocks that were previously heated to 90° C. The mold then was slowly cooled down to room temperature for 24 hours. Upon gelling, the resulting hydrogel sheet was removed from the mold and dehydrated under vacuum at room temperature. After vacuum dehydration, the gel was immersed in saline until equilibrium re-hydration. The equilibrium water content of the final processed gel was 77.17±0.05%.

Example 14

27% Total Polymer of 7:3 PVA:PAA Ratio with 15% PEG; Room Temp Gelling; Vacuum-Dehydrated; Heated PVA (MW=115,000 g/mol (99.7% hydrolyzed), Scientific Polymer Products, Ontario, N.Y.) was mixed into an aqueous solution of PAA (MW=200,000 g/mol, Polysciences) at 90° C. to form a homogenous PVA-PAA solution. The PVA:PAA ratio was 7:3 with 27 w/w % total polymer content in the blend. Subsequently, pre-heated polyethylene glycol (MW=400) (PEG400) of 15 w/w % of PEG with respect to the total PEG and water amount in the mixture was added to the solution with vigorous mechanical stirring at 90° C. to form a homogenous PVA-PAA-PEG solution. Resulting clear solution was degassed to remove air bubbles and poured into a hot glass mold and sealed with a glass cover. This mold was kept between two stainless steel blocks that were previously heated to 90° C. The mold then was slowly cooled down to room temperature for 24 hours. Upon gelling, the resulting hydrogel sheet was removed from the mold and dehydrated under vacuum at room temperature. After vacuum dehydration, the gel was heated at 160° C. in an argon-filled closed chamber already heated to 160° C. for one hour. The heated gel was then immersed in saline until equilibrium re-hydration. The equilibrium water content of the final processed gel was 57.58±0.92%.

Table 3 shows the weight changes and equilibrium water content (EWC) of PVA-PAA hydrogels formed from 27% solid PVA-PAA-PEG blends with 15% PEG by 1 day room temperature gelling at each stage of processing from Examples 11-13.

Example 15

27% Total Polymer of 7:3 PVA:PAA Ratio with 20% PEG; 3 Freeze-Thaw Cycles

PVA (MW=115,000 g/mol (99.7% hydrolyzed), Scientific Polymer Products, Ontario, N.Y.) was mixed into an aqueous solution of PAA (MW=200,000 g/mol, Polysciences) at 90° C. to form a homogenous PVA-PAA solution. The PVA:PAA ratio was 7:3 with 27 w/w % total polymer content in the blend. Subsequently, pre-heated polyethylene glycol (MW=400) (PEG400) of 20 w/w % of PEG with respect to the total PEG and water amount in the mixture was added to the solution with vigorous mechanical stirring at 90° C. to form a homogenous PVA-PAA-PEG solution. Resulting clear solution was degassed to remove air bubbles and poured into a hot glass mold and sealed with a glass cover. This mold was kept between two stainless steel blocks that were previously heated to 90° C. The mold then was placed in a −17° C. freezer for 16 hours, and subsequently thawed at room temperature for 8 hours. This process completed one cycle of freeze-thaw procedure. Upon completion of 3 freeze-thaw cycles, the resulting hydrogel sheet was removed from the mold and immersed in saline until equilibrium re-hydration. The equilibrium water content of the final processed gel was 83.33±0.09%.

TABLE 3

Weight changes and equilibrium water content (EWC) of PVA-PAA-hydrogels.

| Measurements made | Weight Changes (%) | EWC (%) |
|---|---|---|
| As-gelled | 0.00 | Not measured |
| After vacuum dehydration | −59.22 | Not measured |
| After vacuum dehydration followed by re-hydration in saline (Example 13) | 2.49 | 77.17 ± 0.05 |
| After vacuum dehydration and subsequent heating | −60.04 | |
| After vacuum dehydration and subsequent heating followed by re-hydration in saline (Example 14) | −38.00 | 57.58 ± 0.92 |

Example 16

27% Total Polymer of 7:3 PVA:PAA Ratio with 20% PEG; 3 Freeze-Thaw Cycles; Vacuum-Dehydrated PVA (MW=115,000 g/mol (99.7% hydrolyzed), Scientific Polymer Products, Ontario, N.Y.) was mixed into an aqueous solution of PAA (MW=200,000 g/mol, Polysciences) at 90° C. to form a homogenous PVA-PAA solution. The PVA:PAA ratio was 7:3 with 27 w/w % total polymer content in the blend. Subsequently, pre-heated polyethylene glycol (MW=400) (PEG400) of 20 w/w % of PEG with respect to the total PEG and water amount in the mixture was added to the solution with vigorous mechanical stirring at 90° C. to form a homogenous PVA-PAA-PEG solution. Resulting clear solution was degassed to remove air bubbles and poured into a hot glass mold and sealed with a glass cover. This mold was kept between two stainless steel blocks that were previously heated to 90° C. The mold then was placed in a −17° C. freezer for 16 hours, and subsequently thawed at room temperature for 8 hours. This process completed one cycle of freeze-thaw procedure. Upon completion of 3 freeze-thaw cycles, the resulting hydrogel sheet was removed from the mold and dehydrated under vacuum at room temperature. After vacuum dehydration, the gel was immersed in saline until equilibrium re-hydration. The equilibrium water content of the final processed gel was 83.25±0.27%.

Example 17

27% Total Polymer of 7:3 PVA:PAA Ratio with 20% PEG; 3 Freeze-Thaw Cycles; Vacuum-Dehydrated; Heated PVA (MW=115,000 g/mol (99.7% hydrolyzed), Scientific Polymer Products, Ontario, N.Y.) was mixed into an aqueous solution of PAA (MW=200,000 g/mol, Polysciences) at 90° C. to form a homogenous PVA-PAA solution. The PVA:PAA ratio was 7:3 with 27 w/w % total polymer content in the blend. Subsequently, pre-heated polyethylene glycol (MW=400) (PEG400) of 20 w/w % of PEG with respect to the total PEG and water amount in the mixture was added to the solution with vigorous mechanical stirring at 90° C. to form a homogenous PVA-PAA-PEG solution. Resulting clear solution was degassed to remove air bubbles and poured into a hot glass mold and sealed with a glass cover. This mold was kept between two stainless steel blocks that were previously heated to 90° C. The mold then was placed in a −17° C. freezer for 16 hours, and subsequently thawed at room temperature for 8 hours. This process completed one cycle of freeze-thaw procedure. Upon completion of 3 freeze-thaw cycles, the resulting hydrogel sheet was removed from the mold and dehydrated under vacuum at room temperature. After vacuum dehydration, the gel was heated at 160° C. in an argon-filled closed chamber already heated to 160° C. for one hour. The heated gel was then immersed in saline until equilibrium re-hydration. The equilibrium water content of the final processed gel was 66.72±0.19%.

Table 4 shows the weight changes and equilibrium water content (EWC) of PVA-PAA hydrogels formed from 27% solid PVA-PAA-PEG blends with 20% PEG by 3 cycle freeze-thawing at each stage of processing from Examples 15-17.

Example 18

27% Total Polymer of 7:3 PVA:PAA Ratio with 20% PEG; Room Temp Gelling

PVA (MW=115,000 g/mol (99.7% hydrolyzed), Scientific Polymer Products, Ontario, N.Y.) was mixed into an aqueous solution of PAA (MW=200,000 g/mol, Polysciences) at 90° C. to form a homogenous PVA-PAA solution. The PVA:PAA ratio was 7:3 with 27 w/w % total polymer content in the blend. Subsequently, pre-heated polyethylene glycol (MW=400) (PEG400) of 20 w/w % of PEG with respect to the total PEG and water amount in the mixture was added to the solution with vigorous mechanical stirring at 90° C. to form a homogenous PVA-PAA-PEG solution. Resulting clear solution was degassed to remove air bubbles and poured into a hot glass mold and sealed with a glass cover. This mold was kept between two stainless steel blocks that were previously heated to 90° C. The mold then was slowly cooled down to room temperature for 24 hours. Upon gelling, the resulting hydrogel sheet was removed from the mold and immersed in saline until equilibrium re-hydration. The equilibrium water content of the final processed gel was 91.61±0.06%.

TABLE 4

Weight changes and equilibrium water content (EWC) of PVA-PAA-hydrogels.

| Measurements made | Weight Changes (%) | EWC (%) |
|---|---|---|
| As-gelled | 0.00 | Not Measured |
| After re-hydration in saline (Example 15) | 31.33 | 83.33 ± 0.09 |
| After vacuum dehydration | −58.38 | Not Measured |
| After vacuum dehydration followed by re-hydration in saline (Example 16) | 30.08 | 83.25 ± 0.27 |
| After vacuum dehydration and subsequent heating | −59.19 | Not Measured |
| After vacuum dehydration and subsequent heating followed by re-hydration in saline (Example 17) | −23.77 | 66.72 ± 0.19 |

Example 19

27% Total Polymer of 7:3 PVA:PAA Ratio with 20% PEG; Room Temp Gelling; Vacuum-Dehydrated PVA (MW=115,000 g/mol (99.7% hydrolyzed), Scientific Polymer Products, Ontario, N.Y.) was mixed into an aqueous solution of PAA (MW=200,000 g/mol, Polysciences) at 90° C. to form a homogenous PVA-PAA solution. The PVA:PAA ratio was 7:3 with 27 w/w % total polymer content in the blend. Subsequently, pre-heated polyethylene glycol (MW=400) (PEG400) of 20 w/w % of PEG with respect to the total PEG and water amount in the mixture was added to the solution with vigorous mechanical stirring at 90° C. to form a homogenous PVA-PAA-PEG solution. Resulting clear solution was degassed to remove air bubbles and poured into a hot glass mold and sealed with a glass cover. This mold was kept between two stainless steel blocks that were previously heated to 90° C. The mold then was slowly cooled down to room temperature for 24 hours. Upon gelling, the resulting hydrogel sheet was removed from the mold and dehydrated under vacuum at room temperature. After vacuum dehydration, the gel was immersed in saline until equilibrium re-hydration. The equilibrium water content of the final processed gel was 82.12±0.10%.

Example 20

27% Total Polymer of 7:3 PVA:PAA Ratio with 20% PEG; Room Temp Gelling; Vacuum-Dehydrated; Heated PVA (MW=115,000 g/mol (99.7% hydrolyzed), Scientific Polymer Products, Ontario, N.Y.) was mixed into an aqueous solution of PAA (MW=200,000 g/mol, Polysciences) at 90° C. to form a homogenous PVA-PAA solution. The PVA:PAA ratio was 7:3 with 27 w/w % total polymer content in the blend. Subsequently, pre-heated polyethylene glycol (MW=400) (PEG400) of 20 w/w % of PEG with respect to the total PEG and water amount in the mixture was added to the solution with vigorous mechanical stirring at 90° C. to form a homogenous PVA-PAA-PEG solution. Resulting clear solution was degassed to remove air bubbles and poured into a hot glass mold and sealed with a glass cover. This mold was kept between two stainless steel blocks that were previously heated to 90° C. The mold then was slowly cooled down to room temperature for 24 hours. Upon gelling, the resulting hydrogel sheet was removed from the mold and dehydrated under vacuum at room temperature. After vacuum dehydration, the gel was heated at 160° C. in an argon-filled closed chamber already heated to 160° C. for one hour. The heated gel immersed in saline until equilibrium re-hydration. The equilibrium water content of the final processed gel was 63.71±0.42%.

TABLE 5

Weight changes and equilibrium water content (EWC) of PVA-PAA-hydrogels.

| Measurements made | Weight Changes (%) | EWC (%) |
|---|---|---|
| As-gelled | 0.00 | Not Measured |
| After re-hydration in saline (Example 18) | 127.33 | 91.61 ± 0.06 |
| After vacuum dehydration | −58.70 | Not Measured |
| After vacuum dehydration followed by re-hydration in saline (Example 19) | 21.44 | 82.12 ± 0.10 |
| After vacuum dehydration and subsequent heating | −60.06 | Not Measured |
| After vacuum dehydration and subsequent heating followed by re-hydration in saline (Example 20) | −29.54 | 63.71 ± 0.42 |

Table 5 shows the weight changes and equilibrium water content (EWC) of PVA-PAA hydrogels formed from 27% solid PVA-PAA-PEG blends with 20% PEG by 1 day room temperature gelling at each stage of processing from Examples 18-20.

Example 21

27% Total Polymer of 7:3 PVA:PAA Ratio with No PEG; 3 Freeze-Thaw Cycles; Vacuum-Dehydrated PVA (MW=115,000 g/mol (99.7% hydrolyzed), Scientific Polymer Products, Ontario, N.Y.) was mixed into an aqueous solution of PAA (MW=200,000 g/mol, Polysciences) at 90° C. to form a homogenous PVA-PAA solution. The PVA:PAA ratio was 7:3 with 27 w/w % total polymer content in the blend. Resulting clear solution was degassed to remove air bubbles and poured into a hot glass mold and sealed with a glass cover. This mold was kept between two stainless steel blocks that were previously heated to 90° C. The mold then was placed in a −17° C. freezer for 16 hours, and subsequently thawed at room temperature for 8 hours. This process completed one cycle of freeze-thaw procedure. Upon completion of 3 freeze-thaw cycles, the resulting hydrogel sheet was removed from the mold and dehydrated under vacuum at room temperature until the weight changes of the hydrogel due to dehydration reached equilibrium. After vacuum dehydration, the gel was immersed in saline until equilibrium re-hydration. The equilibrium water content of the final processed gel was 71.67±1.00%.

Example 22

27% Total Polymer of 7:3 PVA:PAA Ratio with No PEG; 3 Freeze-Thaw Cycles; PEG400-Immersed PVA (MW=115,000 g/mol (99.7% hydrolyzed), Scientific Polymer Products, Ontario, N.Y.) was mixed into an aqueous solution of PAA (MW=200,000 g/mol, Polysciences) at 90° C. to form a homogenous PVA-PAA solution. The PVA:PAA ratio was 7:3 with 27 w/w % total polymer content in the blend. Resulting clear solution was degassed to remove air bubbles and poured into a hot glass mold and sealed with a glass cover. This mold was kept between two stainless steel blocks that were previously heated to 90° C. The mold then was placed in a −17° C. freezer for 16 hours, and subsequently thawed at room temperature for 8 hours. This process completed one cycle of freeze-thaw procedure. Upon completion of 3 freeze-thaw cycles, the resulting hydrogel sheet was removed from the mold and immersed in 100% PEG400 with agitation until the weight changes of the hydrogel due to PEG immersion reached equilibrium. Subsequently, the PEG-dehydrated PVA-PAA gel was immersed in saline until equilibrium re-hydration. The equilibrium water content of the final processed gel was 76.21±0.10%.

Example 23

7:3 27% Total Polymer of 7:3 PVA:PAA Ratio with No PEG; 3 Freeze-Thaw Cycles; PEG400-Immersed; Vacuum-Dehydrated PVA (MW=115,000 g/mol (99.7% hydrolyzed), Scientific Polymer Products, Ontario, N.Y.) was mixed into an aqueous solution of PAA (MW=200,000 g/mol, Polysciences) at 90° C. to form a homogenous PVA-PAA solution. The PVA:PAA ratio was 7:3 with 27 w/w % total polymer content in the blend. Resulting clear solution was degassed to remove air bubbles and poured into a hot glass mold and sealed with a glass cover. This mold was kept between two stainless steel blocks that were previously heated to 90° C. The mold then was placed in a −17° C. freezer for 16 hours, and subsequently thawed at room temperature for 8 hours. This process completed one cycle of freeze-thaw procedure. Upon completion of 3 freeze-thaw cycles, the resulting hydrogel sheet was removed from the mold and immersed in 100% PEG400 with agitation until the weight changes of the hydrogel reached equilibrium. Subsequently, the PEG-doped PVA-PAA gel was dehydrated under vacuum at room temperature. After vacuum dehydration, the gel was immersed in saline until equilibrium re-hydration. The equilibrium water content of the final processed gel was 74.64±0.19%.

Example 24

27% Total Polymer of 7:3 PVA:PAA Ratio with No PEG; 3 Freeze-Thaw Cycles; PEG400-Immersed; Vacuum-Dehydrated; Heated PVA (MW=115,000 g/mol (99.7% hydrolyzed), Scientific Polymer Products, Ontario, N.Y.) was mixed into an aqueous solution of PAA (MW=200,000 g/mol, Polysciences) at 90° C. to form a homogenous PVA-PAA solution. The PVA:PAA ratio was 7:3 with 27 w/w % total polymer content in the blend. Resulting clear solution was degassed to remove air bubbles and poured into a hot glass mold and sealed with a glass cover. This mold was kept between two stainless steel blocks that were previously heated to 90° C. The mold then was placed in a −17° C. freezer for 16 hours, and subsequently thawed at room temperature for 8 hours. This process completed one cycle of freeze-thaw procedure. Upon completion of 3 freeze-thaw cycles, the resulting hydrogel sheet was removed from the mold and immersed in 100% PEG400 with agitation until the weight changes of the hydrogel reached equilibrium. Subsequently, the PEG-doped PVA-PAA gel was dehydrated under vacuum at room temperature. After vacuum dehydration, the gel was heated at 160° C. in an argon-filled closed chamber already heated to 160° C. for one hour. The heated gel was then immersed in saline until equilibrium re-hydration. The equilibrium water content of the final processed gel was 55.68±1.52%.

TABLE 6

Weight changes and equilibrium water content (EWC) of PVA-PAA-hydrogels.

| Measurements made | Weight Changes (%) | EWC (%) |
|---|---|---|
| After Freeze-thaw process | 0.0 | Not measured |
| After vacuum dehydration | −67.32 | Not measured |
| After vacuum dehydration followed by re-hydration in saline | −2.65 | 71.67 ± 1.00 |
| After immersing in 100% PEG400 | −53.38 | Not measured |
| After immersing in 100% PEG400 followed by re-hydration in saline | 18.54 | 76.21 ± 0.10 |
| After immersing in 100% PEG400 and subsequent vacuum dehydration | −56.09 | Not measured |
| After immersing in 100% PEG400 and subsequent vacuum dehydration followed by re-hydration in saline | 12.39 | 74.64 ± 0.19 |
| After immersing in 100% PEG400 and subsequent vacuum dehydration and heating | −57.29 | Not measured |
| After immersing in 100% PEG400 and subsequent vacuum dehydration and heating followed by re-hydration in saline | −30.92 | 55.68 ± 1.52 |

Table 6 shows the weight changes and equilibrium water content (EWC) of PVA-PAA hydrogels formed from 27% solid PVA-PAA blends by 3 cycle freeze-thawing at each stage of processing from Examples 21-24.

Example 25

Creep Test of PVA Gels Produced by Examples 1-24

Hydrogel sheet samples from above examples were machined with a 17 mm diameter trephine and were allowed to equilibrate in saline solution at 40° C. for at least 24 hours prior to the start of the creep test.

The hydrogel creep test was done on a MTS (Eden Prairie, Minn.) 858 Mini Bionix servohydraulic machine. Cylindrical hydrogel specimens, approximately 17 mm in diameter and between 5-10 mm in height, were placed between stainless steel compression plates for testing. Prior to the start of the test, the top and bottom compression plates were brought together and the LVDT displacement was zeroed at this position. After placing the specimen on the bottom plate, the top plate was lowered until it made contact with the top surface of the creep specimen. The displacement reading from the LVDT on the MTS was recorded as the height of the specimen. The compressive load was initially ramped at a rate of 50 Newton/minute (N/min) to a creep load of 100 Newton (N). This load was maintained constant for 10 hours. The load was subsequently reduced at a rate of 50 N/min to a recovery load of 10 N. This load was also held constant for 10 hours. Time, displacement and load values were recorded once every 2 seconds during the loading and unloading cycles. The data was plotted as compressive strain vs. time to compare the creep behavior of different hydrogel formulations described above (see FIG. 3).

Figure 3:
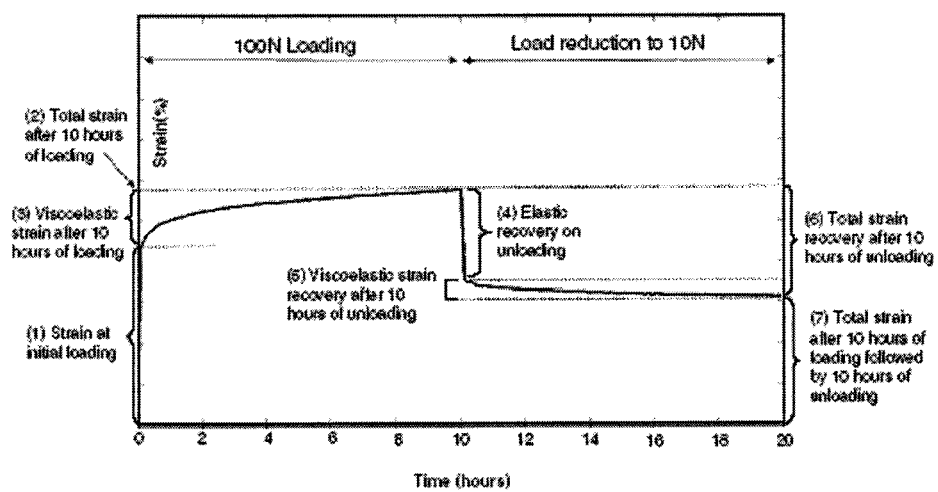
FIG. 3 illustrates creep behavior in Strain vs. Time plots for the 10 hour loading and 10 hour unloading cycles respectively.

Creep strain was calculated as (1) the strain at the completion of ramp-up to 100 N load, (2) the total strain after 10 hours of loading, (3) the viscoelastic strain after 10 hours of loading, (4) the elastic recovery upon unloading from 100 to 10 N, (5) the viscoelastic strain recovery after 10 hours of unloading under 10 N, (6) the total strain recovery after 10 hours of unloading under 10 N, and (7) the total strain after 10 hours of loading followed by 10 hours of unloading under 10 N (see FIG. 3). FIG. 3 shows creep behavior is characterized in the Strain vs. Time plots for the 10 hour loading and 10 hour unloading cycles respectively. Table 7 shows the elastic and viscoplastic strains achieved during the loading and unloading stages of the creep experiments with the hydrogel samples used in example 25.

TABLE 7

Elastic and viscoplastic strains observed during the loading and unloading stages of the creep experiments.

| Sample Number | Sample (all samples were hydrated in saline at room temperature to achieve equilibrium hydration levels and then conditioned in 40° C. saline for at least 24 hours prior to testing) | Strain on Initial Loading (%) | Total Strain after 10 hours of Loading (%) |
|---|---|---|---|
| 1 | 15% 7:3 PVA:PAA (200 K); 15% PEG; 3FT; vac-deh (Example 2) | 10.9 | 25.5 |
| 2 | 15% 7:3 PVA:PAA (200 K); 15% PEG; 3FT; vac-deh; heated (Example 3) | 18.4 | 36.2 |
| 3 | 15% 7:3 PVA:PAA (200 K); 15% PEG; 3FT; dePEGed; vac-deh; heated (Example 4) | 8.9 | 12.0 |
| 4 | 15% 7:3 PVA:PAA (200 K); No PEG; 3FT; vac-deh (Example 6) | 34.1 | 42.3 |
| 5 | 15% 7:3 PVA:PAA (200 K); No PEG; 3FT; PEG-imm (Example 8) | 57.1 | 71.9 |
| 6 | 15% 7:3 PVA:PAA (200 K); No PEG; 3FT; PEG-imm; vac-deh; heated (Example 10) | 10.9 | 25.5 |
| 7 | 30% 7:3 PVA:PAA (50 K); 15% PEG; RT 1 day; vac-deh: heated (Example 12) | 11.4 | 15.7 |
| 8 | 27% 7:3 PVA:PAA (200 K); 20% PEG; 3FT; vac-deh; heated (Example 17) | 27.2 | 40.8 |

TABLE 7-continued

Elastic and viscoplastic strains observed during the loading and unloading stages of the creep experiments.

| | | | |
|---|---|---|---|
| 9 | 27% 7:3 PVA:PAA (200 K); 20% PEG; RT 1 day; vac-deh; heated (Example 19) | 22.7 | 32.6 |
| 10 | 27% 7:3 PVA:PAA (200 K); No PEG; 3FT; PEG-imm; vac-deh; heated (Example 24) | 9.8 | 14.3 |

| Sample Number | Viscoelastic Strain after 10 hours of Loading (%) | Elastic Recovery on Unloading (%) | Viscoelastic Strain Recovery after 10 hours of Unloading (%) | Total Strain Recovery after 10 hours of Unloading (%) | Total Strain after 10 hours of Loading followed by 10 hours of Unloading (%) |
|---|---|---|---|---|---|
| 1 | 14.5 | 7.5 | 6.8 | 14.3 | 11.1 |
| 2 | 17.8 | 14.3 | 9.1 | 23.4 | 12.8 |
| 3 | 3.1 | 4.3 | 3.6 | 7.9 | 4.1 |
| 4 | 8.2 | 20.6 | 6.0 | 26.5 | 15.8 |
| 5 | 14.8 | 15.5 | 2.0 | 17.5 | 54.4 |
| 6 | 14.5 | 7.5 | 6.8 | 14.3 | 11.1 |
| 7 | 4.3 | 7.3 | 3.9 | 11.2 | 4.5 |
| 8 | 13.6 | 17.3 | 9.7 | 27.0 | 13.9 |
| 9 | 9.9 | 14.9 | 9.6 | 24.5 | 8.1 |
| 10 | 4.5 | 8.9 | 4.3 | 13.2 | 1.1 |

Figure 4:
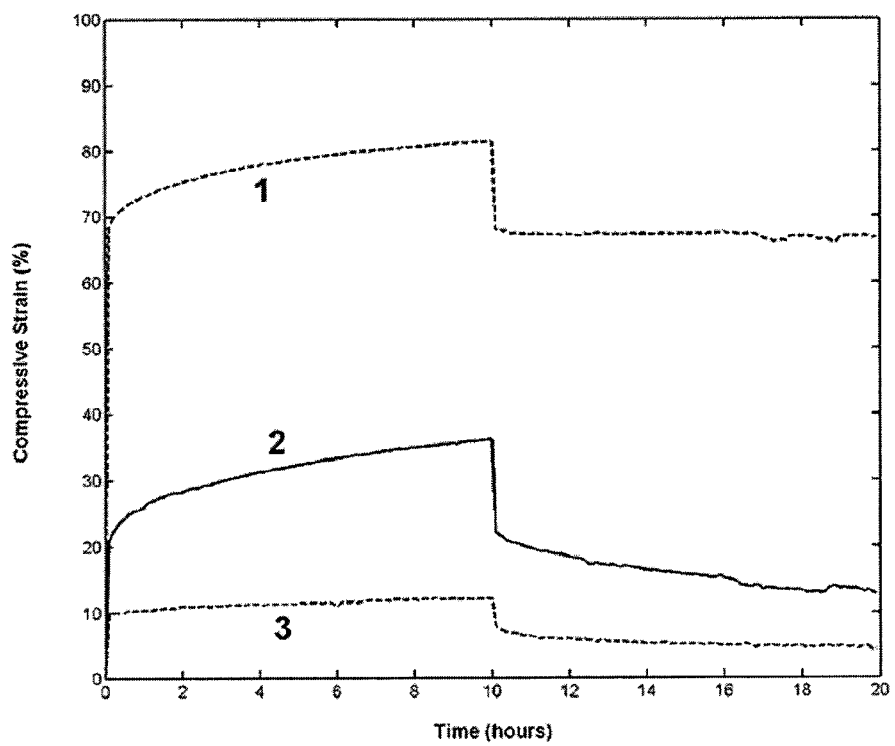
FIG. 4 shows creep behavior in Strain vs. Time plots for the 10 hour loading and unloading cycles, respectively, for the samples 1-3 as shown in Table 7.
Figure 5:
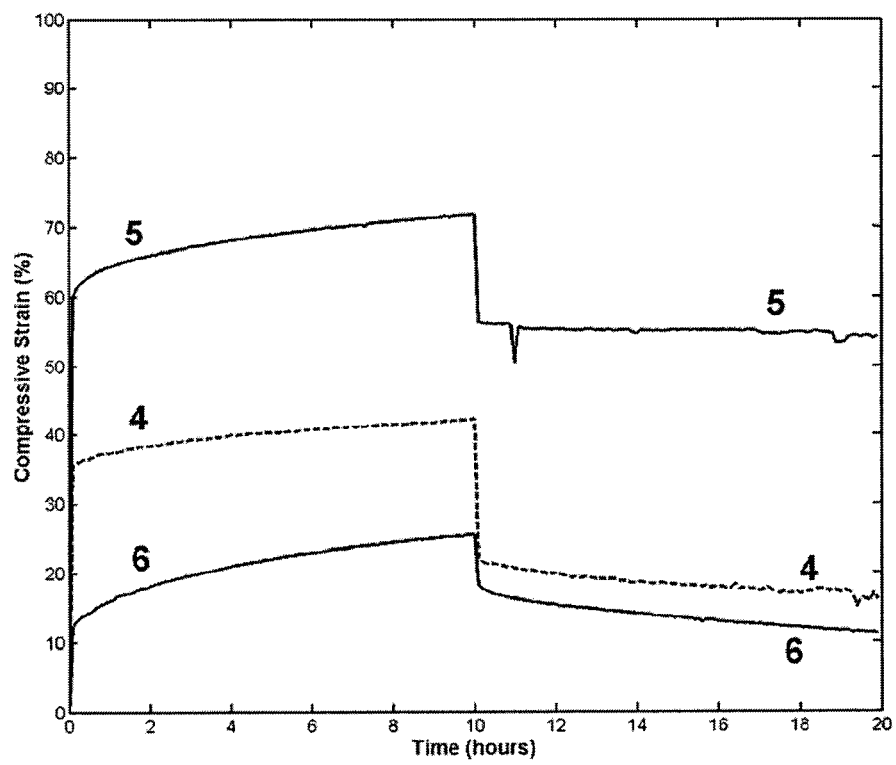
FIG. 5 shows creep behavior in Strain vs. Time plots for the 10 hour loading and unloading cycles, respectively, for samples 4-6 refer as shown in Table 7.
Figure 6:
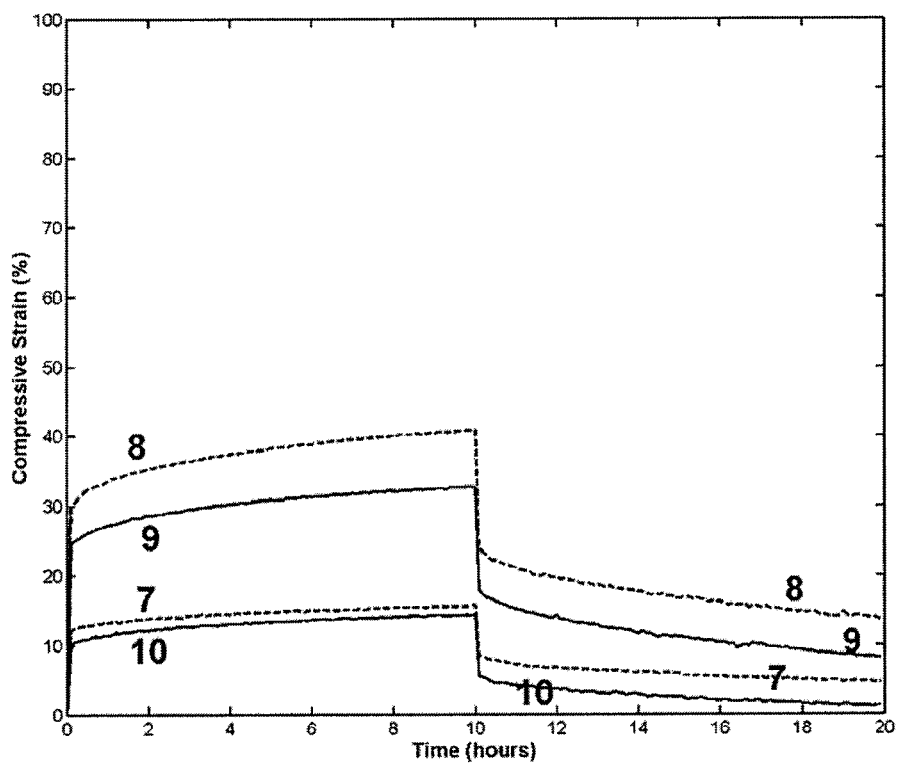
FIG. 6 illustrates creep behavior in Strain vs. Time plots for the 10 hour loading and unloading cycles, respectively, for the samples 7-10 as shown in Table 7.
Figure 7:
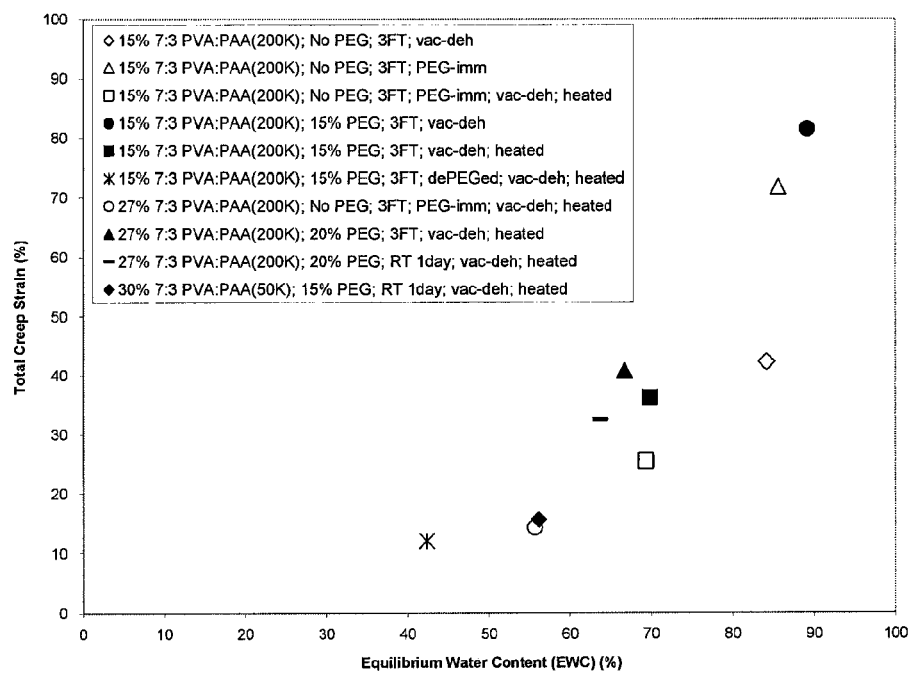
FIG. 7 shows total creep strain of PVA hydrogels obtained from creep test as described in Example 24 and is plotted as a function of equilibrium water content.

FIGS. 4-6 further illustrates creep behavior is characterized in the Strain vs. Time plots for the 10 hour loading and unloading cycles, respectively, for the samples numbers 1-10 as shown in Table 7. FIG. 7 shows total creep strain of PVA hydrogels obtained from creep test as described in Example 24 and is plotted as a function of equilibrium water content.

Example 26

Coefficient of Friction Measurements of PVA Gels Produced by Examples 1-24

Coefficient of friction is measured on hydrogel samples formed by above methods in DI water at 40° C. against CoCr. An aluminum bath is mounted onto the Peltier plate and the hydrogel sample is placed in the bath. In this test, a CoCr ring is mounted into the upper fixture of a shear rheometer (AR-1000, TA Instruments Inc.). The CoCr runs against the hydrogel sample at a constant shear rate of 0.11/s. The torsional load is recorded under normal loads of approximately 1, 2, 4, 6, and 8 N. Using the method of Kavehpour and McKinley (see Kavehpour, H. P. and McKinley, G. H., Tribology Letters, 17(2), pp. 327-335, 2004), the coefficient of friction between the hydrogel and the CoCr counter face can be calculated.

Example 27

Comparison of PVA Gels Having the Same Composition by Different Methods of Making (PEG Presence During PVA-PAA Gelling Vs PEG Sequentially Incorporated after PVA-PAA Gelling)

The PVA hydrogels made by the methods described in Example 1 (where PEG is present during PVA-PAA gelling; denoted as "PVA-PAA-PEG gel") and in Example 8 (where PEG is sequentially incorporated after PVA-PAA gelling; denoted as "PVA-PAA gel with PEG incorporated") essentially contain all three components of PVA, PAA, and PEG before they are further processed, for example, rehydrated in saline or dehydrated by thermal treatment. However, whether PEG is present during the time of PVA gelling or it is incorporated into the already-formed PVA gels result in slightly different PVA microstructures as seen in FIGS. 8 and 9.

Figure 8:
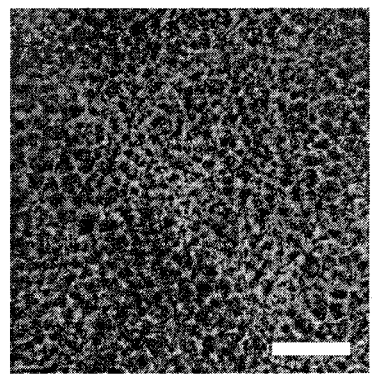
FIG. 8 depicts a confocal micrograph of rehydrated PVA hydrogel made by a method (example 1) where PEG was present in the PVA and PAA solution during the time of gelling process (scale bar=20 µm).
Figure 9:
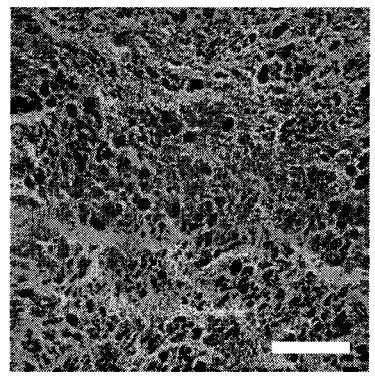
FIG. 9 depicts a confocal micrograph of rehydrated PVA hydrogel made by a method (example 8) where PEG was sequentially incorporated in pre-made PVA-PAA gels (scale bar=20 µm).

FIG. 8 illustrates a confocal micrograph of rehydrated PVA hydrogel made by a method (Example 1) where PEG was present in the PVA and PAA solution during the time of gelling process (scale bar=20 µm). FIG. 9 illustrates a confocal micrograph of rehydrated PVA hydrogel made by a method (Example 8) where PEG was sequentially incorporated in pre-made PVA-PAA gels (scale bar=20 µm). Both gels, as depicted in FIGS. 8 and 9, contain the same composition ratio of PVA and PAA (7:3).

The PVA-PAA-PEG gel in FIG. 1 shows more uniformly sized pores surrounded by finer PVA struts than the PVA-PAA gel with PEG incorporated in FIG. 2, which shows much thicker and web-like polymer matrix with various shaped and sized pores. Presence of PEG during the PVA-PAA gelling tend to increase the final water content in the further processed gel, which closely affects creep resistance. FIG. 3 shows a comparison of creep resistance in such PVA hydrogels that were thermally treated by methods described in Examples 3 and 9, respectively. The PVA-PAA-PEG gel results in a slightly higher total creep resistance with greater elastic response and the same final creep strain compared to the PVA-PAA gel with PEG incorporated.

Figure 10:
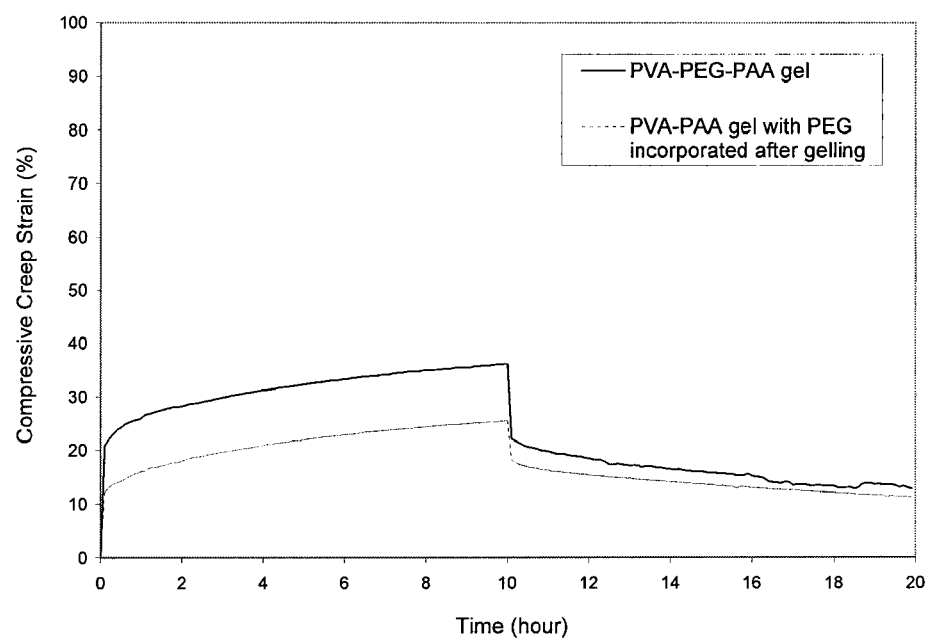
FIG. 10 shows the creep resistance of "The PVA-PAA-PEG gel" where PEG was present during PVA gelling and "PVA-PAA gel with PEG incorporated" where PEG was incorporated after PVA gelling. Both gels were thermally treated and rehydrated in saline prior to creep deformation test.

FIG. 10 shows creep resistance of the PVA-PAA-PEG gel where PEG was present during PVA gelling and PVA-PAA gel with PEG incorporated where PEG was incorporated after PVA gelling. Both gels were thermally treated and rehydrated in saline prior to creep deformation test.

Example 28

Diffusion of PAA into PVA Hydrogels

This example shows another method of including PAA into PVA gels by immersing formed PVA gels into PAA solutions. PEG can be mixed in PAA solutions simultaneously or PAA-absorbed PVA gels can be sequentially immersed in PEG 100% or other PEG containing solvents.

Thirty grams of poly (vinyl alcohol) (PVA, MW=115,000) were added to 170 grams of cold deionized water and stirred while heating for about 2 hours to prepare a fully dissolved 15% (wt) PVA solution. The dissolved PVA solution was kept for in an air convection oven at 90° C. for degassing. PEG was heated to 90° C. in an air convection oven. 66 grams of hot poly (ethylene glycol) (PEG, MW=400) (at approximately 90° C.) was slowly mixed to the hot PVA solution by mechanical stirring while heating. The gelling solution of PVA-PEG was poured into different size molds kept at 90° C. The molds were covered with an insulating blanket and left to cool down to room temperature. The solution formed a hydrogel upon cooling down to room temperature. The hydrogel was removed from the mold and placed in a saline solution for "dePEGing" process, which removes the residual PEG in the gel by exchanging with water during rehydration in saline. Such dePEGed gels are then used as basal PVA gels for diffusion of PAA.

PVA cryogels can be used as basal PVA gels. A hot 15% PVA aqueous solution was poured into pre-heated molds (for example, the mold can be pre-heated to a temperature between about 1 and about 200° C., preferably between about 25° C. and about 150° C., more preferably about 90° C.) and the molds were placed in a −17° C. freezer for 16 hours, and subsequently thawed at room temperature for 8 hours. This process completed one cycle of freeze-thaw procedure. Upon completion of 1 or more freeze-thaw cycles, the hydrogel was removed from the mold and was subject to PAA diffusion.

Figure 11:
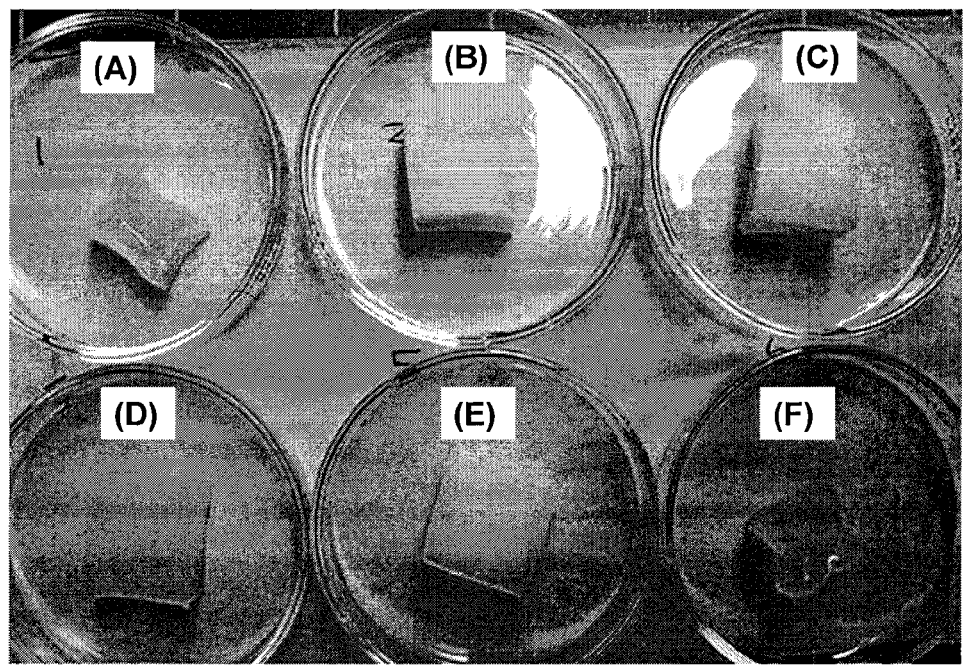
FIG. 11 shows DePEG PVA hydrogels after PAA diffusion by immersion in six different PAA aqueous solutions including; 11(A) 25% PAA (MW=200K) solution, 11(B) 5% PAA (MW=200K), 11(C) 5% PAA (MW=5K), 11(D) 25% PAA (MW=5K), 11(E) deionized water with no PAA (control), and 11(F) about 50% PAA (MW=5K).

Two different molecular weight PAA were (MW=200,000 g/mol (99.7% hydrolyzed), 25 w/w % in water, polysciences; MW=5,000 g/mol, 49.24 w/w % in water) dissolved in deionized water at room temperature to prepare 5% and 25% aqueous solutions of each molecular weight PAA. 49.24 w/w % PAA (MW=5,000 g/mol) was used with no dilution as ~50% concentration. DePEGed gels were cut into six pieces of 20 mm×20 mm×14 mm dimension to ensure uniform surface to volume ratio in each specimen. Each specimen was immersed in six different solutions and mechanically agitated (see FIG. 11). The weight change of each specimen was monitored until the diffusion process reached equilibrium. FIG. 11 depicts DePEGed PVA hydrogels after PAA diffusion by immersion in six different PAA aqueous solutions, as FIG. 11(A) 25% PAA (MW=200K) solution, FIG. 11(B) 5% PAA (MW=200K), FIG. 11(C) 5% PAA (MW=5K), FIG. 11(D) 25% PAA (MW=5K), FIG. 11(E) deionized water with no PAA (control), and FIG. 11(F) ~50% PAA (MW=5K).

Initially opaque dePEGed gel (see FIG. 11E) became translucent and distorted in shape (see FIG. 11A and FIG. 11F), and slightly opaque (see FIG. 11D), which indicates that PAA has been diffused into the gels and water has been extracted out of the gels. The effects of PAA diffusion can be controlled by PAA concentration and PAA molecular weight during the PAA immersion. PAA diffused PVA gels are then subsequently subject to further processing to stabilize the PAA within the PVA-matrix by crosslinking methods such as heating, radiation, chemical reaction, and the like.

Table 8 shows the weight changes of each dePEGed PVA hydrogels after PAA diffusion by immersion in six different PAA aqueous solutions.

TABLE 8

Weight changes of each dePEGed PVA hydrogels after PAA diffusion by immersion in six different PAA aqueous solutions.

| samples | Condition of PAA aqueous solutions used for immersion | | Weight changes (%) |
|---|---|---|---|
| | PAA concentration (w/w %) | PAA molecular weight (g/mol) | |
| A | 25 | 200,000 | −85.36 |
| B | 5 | 200,000 | −0.79 |
| C | 5 | 5,000 | 4.08 |

TABLE 8-continued

Weight changes of each dePEGed PVA hydrogels after PAA diffusion by immersion in six different PAA aqueous solutions.

| samples | Condition of PAA aqueous solutions used for immersion | | Weight changes (%) |
|---|---|---|---|
| | PAA concentration (w/w %) | PAA molecular weight (g/mol) | |
| D | 25 | 5,000 | 6.04 |
| E | 0 | — | 0.35 |
| F | ~50 (49.24) | 5,000 | −55.77 |

Example 29

25% Total Polymer of Various PVA:PAA Ratios, PEG-Doped or PEG-Blended, Followed by Post-Gelation Treatments PVA (MW=115,000 g/mol (99.7% hydrolyzed), Scientific Polymer Products) was mixed into an aqueous solution of PAA (MW=200,000 g/mol, Polysciences) at 90° C. to form a homogenous PVA-PAA solution. The PVA:PAA weight ratio was varied from "PVA only" (i.e., contains no PAA), 9:1, 8:2 to 7:3 with 25 w/w % total polymer content in each blend. Two types of gels, for example, PEG-doped (Type 1) and PEG-blended (Type 2) with different blending ratios of PVA:PAA were used.

Type 1—PEG-Doped Gels:

PVA-PAA solution was poured into pre-heated glass sheet molds and subjected to three freeze-thaw cycles (16 hour-freezing at −17° C. and 8 hour-thawing at room temperature). Subsequently, the molded gels were immersed in 100% PEG (PEG-doping by immersion) followed by vacuum dehydration and annealing at 160° C. in argon in a self-pressurized vessel for an hour. For argon gas atmosphere, the vessel containing the gels was purged with argon gas for at least 5 minutes prior to annealing. It is believed that there were incidents where the argon-purged vessels were not completely sealed during the annealing process. Consequently, the samples were not annealed in 100% inert argon gas, i.e., the samples were exposed to residual air in argon gas during annealing.

Type 2—PEG-Blended Gels:

About 15 w/w % PEG (with respect to the total PEG and the amount of water in the PVA-PAA mixture) was pre-heated at 90° C. and added to a hot PVA-PAA mixture to form a homogeneous solution/blend of PVA-PAA-PEG. The resulting homogeneous polymer blend was poured into a pre-heated glass molds. Subsequently, the molded gels were subjected to three freeze-thaw cycles followed by vacuum dehydration and annealing at about 160° C. under argon in a self-pressurized vessel for an hour. Each gel sheet was immersed in deionized (DI) water to remove residual PEG and to reach an equilibrated rehydration.

The non-annealed "PVA only" (that is, PVA with no PAA) gels in both Types 1 and 2 were made by rehydrating the gels in DI water immediately upon removal from the molds after completion of the freeze-thaw cycles.

Creep Test:

Cylindrical disks were cut from each hydrated hydrogel sheet with a 17 mm diameter trephine. After equilibration in DI water at 40° C. for 24 hours, creep tests were performed in a DI water bath at 40° C. on a multi-station mechanical tester (Cambridge Polymer Group, Boston, Mass.). Gel disks were compressed between polycarbonate plates at a ramping rate of 50 N/min while immersed in DI water at 40° C., to a creep load of 100 Newton (N). The load was maintained constant for 10 hours and subsequently reduced at a rate of 50 N/min to a recovery load of 10 N. This load also was held constant for 10 hours. Time, displacement and load values were recorded during the loading. The total creep strain was taken as a representative characteristic of the results.

Equilibrium Water Content (EWC):

The hydrogel samples were equilibrium hydrated in deionized (DI) water either at 25° C. or at 40° C. at least for 24 hours and dried in vacuum oven for 1 day, subsequently dried in an air convection oven at 90° C. until no significant weight changes were detected. The EWC in a gel was then calculated by the ratio of the difference between the hydrated and dehydrated weights to the weight at the equilibrated hydration state.

Coefficient of Friction:

The COF testing was performed on a AR2000ex rheometer (TA Instruments, Newark, Del.) in DI water at 40° C. using a custom-designed annular CoCr ring (outer diameter 31.2, inner diameter 28.8 mm, and surface roughness, $R_a$=0.08 µm) against flat hydrogels in a custom-designed aluminum bath. The samples were equilibrated in DI water at 40° C. for 1 day prior to the test. Torque, normal force, and velocity data were recorded for 90 seconds at 1, 3, 5 and 7 N with 2 minutes equilibration at the given load in between the runs from low to high loading at a constant shear rate of 0.11/s and analyzed for the coefficient of friction calculation.

Figure 12A:
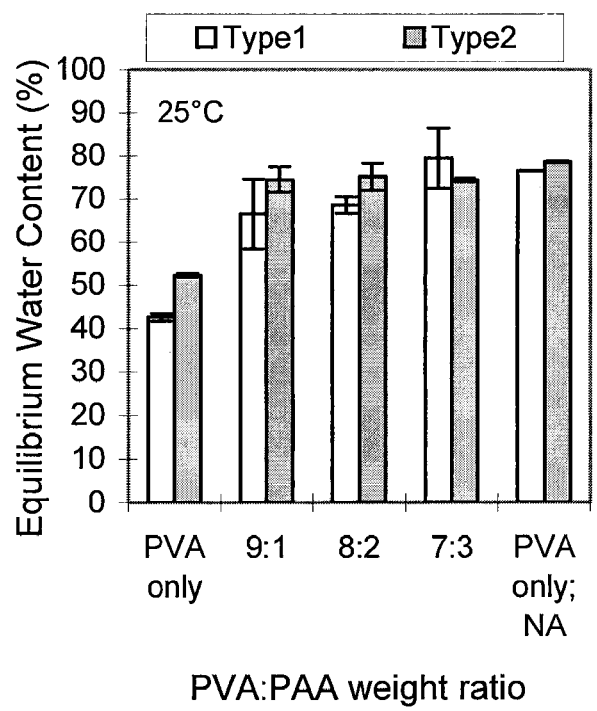
FIGS. 12A and 12B show equilibrium water content (EWC) of the PAA-containing PVA hydrogels. "PVA only; NA" indicates the non-annealed hydrogel made with only PVA without PAA. The hydrogels were equilibrated at 25° C. (12A) or 40° C. (12B) prior to drying for EWC measurement.
Figure 12B:
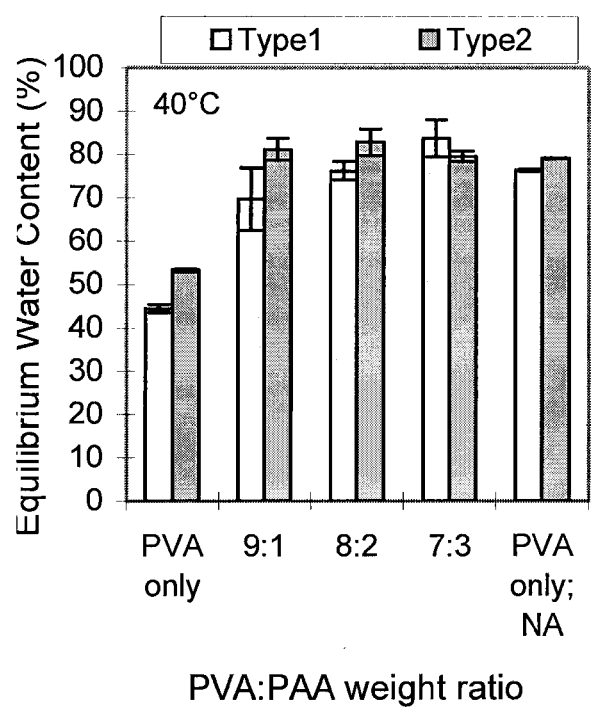
Figure 13:
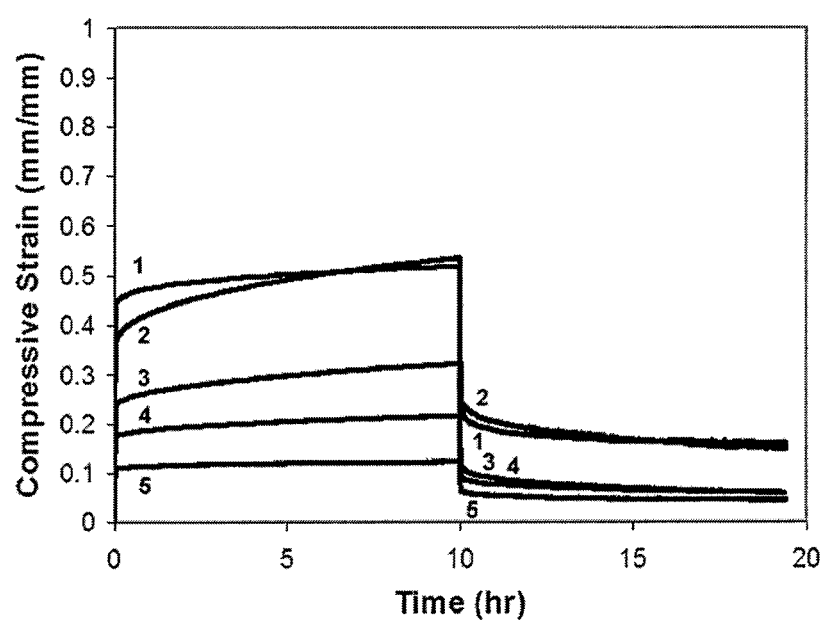
FIG. 13 shows the typical creep behavior of the PAA-containing PVA gels with various PVA-PAA ratios made by type 1 gel method. (1) PVA only, non-annealed (2) 7:3 PVA:PAA, (3) 8:2 PVA:PAA, (4) 9:1 PVA:PAA, and (5) PVA only.
Figure 14:
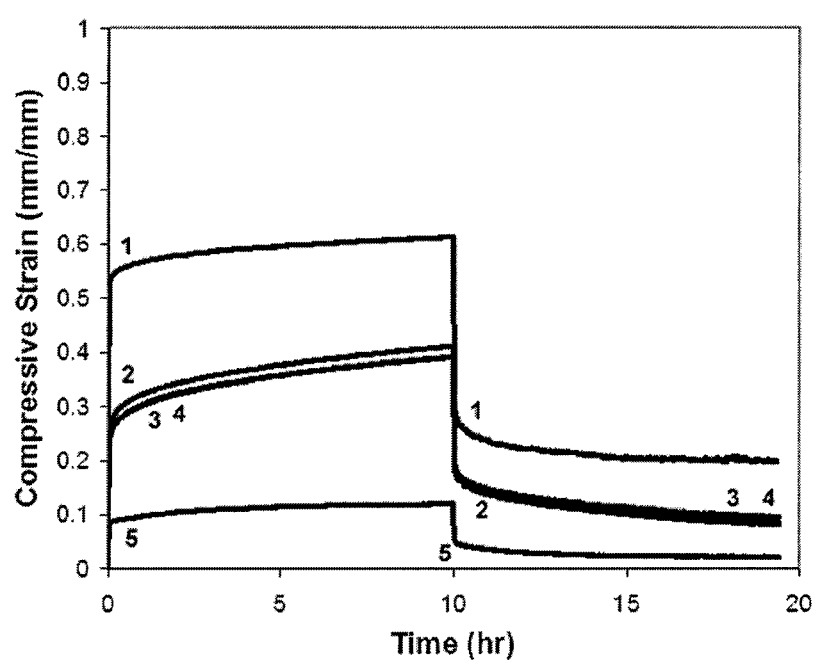
FIG. 14 shows the typical creep behavior of the PAA-containing PVA gels with various PVA-PAA ratios made by type 2 gel method. (1) PVA only, non-annealed (2) 8:2 PVA:PAA, (3) 7:3 PVA:PAA, (4) 9:1 PVA:PAA, and (5) PVA only.
Figure 15:
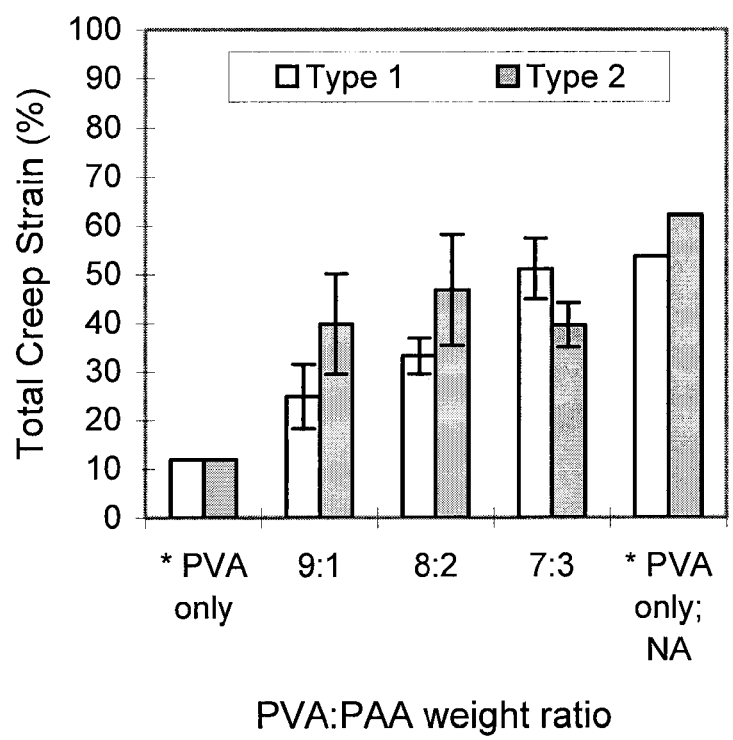
FIG. 15 illustrates total creep strain of the PAA-containing PVA hydrogels. Average numbers of 3 values and standard deviation are shown except for the case of *, for which the average of 2 values were presented.

Results:

Overall, adding PAA in PVA gels significantly increased the EWC after annealing for both type 1 and type 2 gels (see FIGS. 12A and 12B, also see Table 9 for detailed data). FIGS. 12A and 12B illustrates the EWC of the PAA-containing PVA hydrogels ("PVA only; NA" indicates the non-annealed hydrogel made with only PVA without PAA). Such effects were more pronounced for the PVA hydrogels that were equilibrated in DI at 40° C. (FIG. 12B) prior to EWC measurement than the ones equilibrated in DI at 25° C. (FIG. 12A). The presence of PAA increased the EWC of annealed PVA hydrogels up to comparable values to that of the non-annealed PVA hydrogels.

TABLE 9

Equilibrium water content of the PAA-containing PVA hydrogels as illustrated in FIG. 12A and 12B.

| PVA:PAA Weight Ratio | EWC(%) at 25° C. DI | | EWC(%) at 40° C. DI | |
|---|---|---|---|---|
| (25% polymer content) | Type 1 | Type 2 | Type 1 | Type 2 |
| PVA only | 42.7 ± 0.9 | 52.3 ± 0.4 | 44.5 ± 0.9 | 53.3 ± 0.3 |
| 9:1 | 66.6 ± 8.1 | 74.6 ± 2.9 | 69.8 ± 7.2 | 81.2 ± 2.5 |
| 8:2 | 68.6 ± 1.9 | 75.2 ± 3.1 | 76.3 ± 2.0 | 82.9 ± 3.1 |
| 7:3 | 79.6 ± 7.0 | 74.5 ± 0.3 | 83.8 ± 4.3 | 79.6 ± 1.3 |
| PVA only; NA (Non-annealed) | 76.5 ± 0.1 | 78.7 ± 0.2 | 76.5 ± 0.2 | 79.1 ± 0.1 |

Creep resistance of the annealed gels was reduced with the presence of PAA due to increased EWC. (See FIGS. 13 and 14 for typical creep behaviors of the PAA-containing PVA hydrogels made by Type 1 and Type 2 methods, respectively) Nevertheless, except for Type 1 gel with PVA:PAA ratio of 7:3, all of PAA-containing annealed PVA gels showed superior creep resistance to that of the non-annealed PVA gels with no PAA (PVA only; NA) (see FIG. 15 for total creep strain comparison of the PAA-containing PVA hydrogels).

Figure 16:
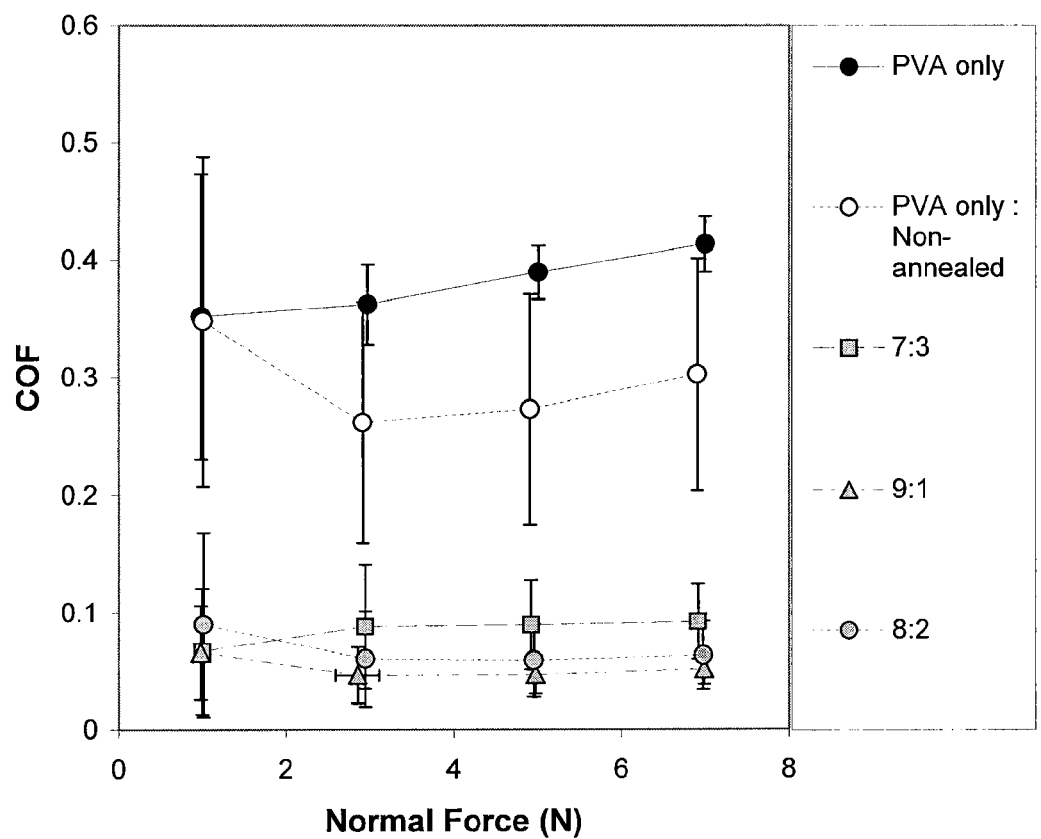
FIG. 16 shows Coefficient of Friction (COF) of the PAA-containing PVA gels made by type 1 gel method.
Figure 17:
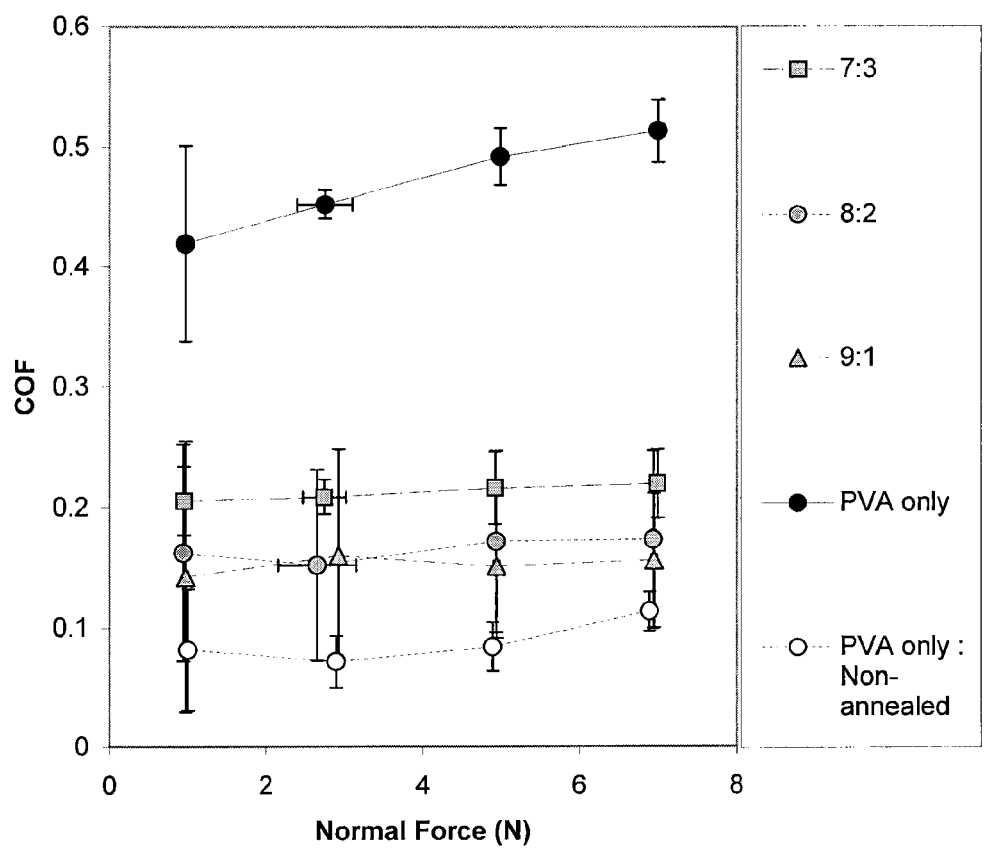
FIG. 17 illustrates Coefficient of Friction (COF) of the PAA-containing PVA gels made by type 2 gel method.
Figure 18:
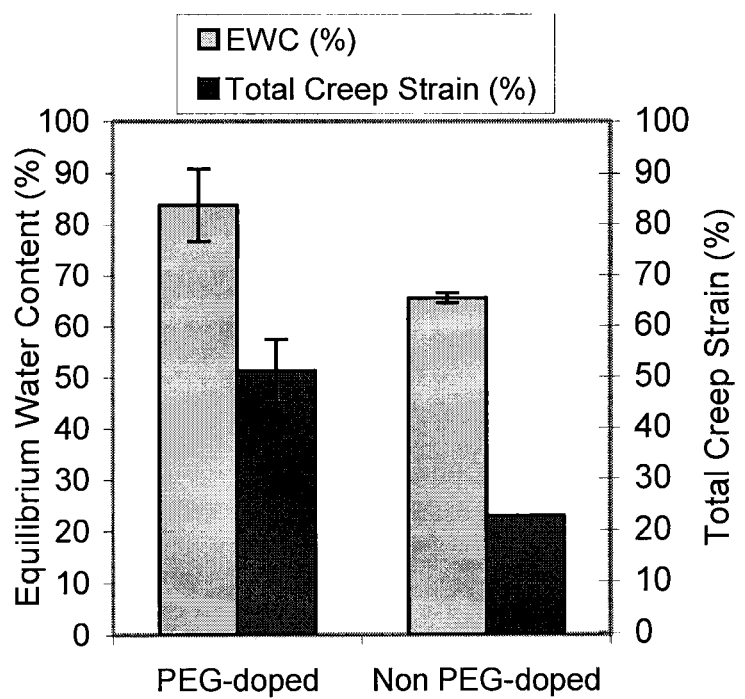
FIG. 18 shows equilibrium water content (EWC) and the total creep strain of 25% total polymer hydrogels of 7:3 PVA:PAA ratio made with or without the PEG doping step as described in Example 30. The hydrogels were equilibrated 40° C. prior to drying for EWC measurement.
Figure 19:
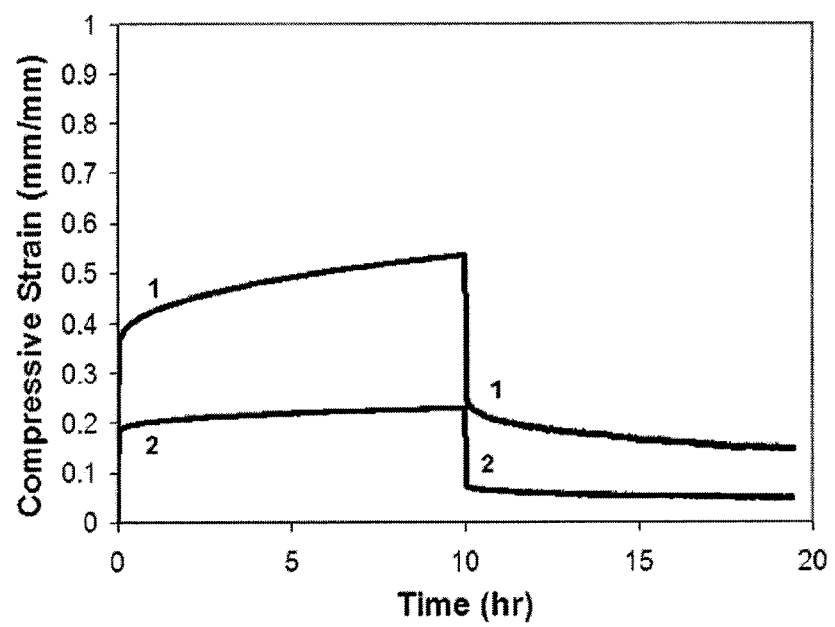
FIG. 19 shows the typical creep behavior of 25% total polymer hydrogels of 7:3 PVA:PAA ratio made with or without the PEG doping step as described in Example 30. (1) PEG-doped and (2) non PEG-doped FIG. 20 Coefficient of Friction (COF) of 25% total polymer hydrogels of 7:3 PVA:PAA ratio made with or without the PEG doping step as described in Example 30.

The lubricity of the annealed PVA gels was significantly improved in the presence of PAA for both type 1 and type 2 gels (see FIGS. 16 and 17), as indicated by their COF values being lower than those of 10:0 gels. FIGS. 16 and 17 illustrate Coefficient of Friction (COF) of the PAA-containing PVA gels made by Type 1 and Type 2 methods, respectively. The 7:3 (PVA:PAA) gels that had the highest amounts of PAA present in the gel seemed slightly less lubricious than 8:2 or 9:1 in both gel types, although the differences were not statistically significant. Note that the presence of PAA resulted in significantly lower COF values than the values that could be obtained by Type 1 PVA only gels whether or not the gels were annealed. Type 1 gel with PVA:PAA ratio of 9:1 is the optimum formulation among the gels described in this example, in terms of minimizing the changes in the COF and creep resistance during annealing.

Example 30

Effects of PEG 400-Doping Step Prior to Annealing in 25% Total Polymer of 7:3 PVA:PAA Ratio with No PEG, 3 Freeze-Thaw Cycles; Vacuum-Dehydrated; and Heated The effects of PEG 400 presence in the PAA-containing PVA hydrogels during heating were quantified in terms of EWC, creep resistance, and coefficient of friction. PVA (MW=115,000 g/mol (99.7% hydrolyzed), Scientific Polymer Products) was mixed into an aqueous solution of PAA (MW=200,000 g/mol, Polysciences) at 90° C. to form a homogenous PVA-PAA solution. 25% total polymer of 7:3 PVA:PAA gels were made by subjecting PVA-PAA solution poured into pre-heated glass sheet molds to three freeze-thaw cycles (16 hour-freezing at −17° C. and 8 hour-thawing at room temperature). Subsequently, the "PEG-doped" group (according to Example 29) was immersed in PEG400 (for PEG-doping), followed by vacuum dehydration and annealing at 160° C. under argon in a self-pressurized vessel for one hour. For argon gas atmosphere, the vessel containing the gels was purged with argon gas for at least 5 minutes prior to annealing. It is believed that there were incidents where the argon-purged vessels were not completely sealed during the annealing process. Consequently, the samples were not annealed in 100% inert argon gas, i.e., the samples were exposed to residual air in argon gas during annealing.

The gels in control group (non PEG-doped) were vacuum dehydrated immediately after removal of gels from molds, omitting the PEG-doping step, followed by the same annealing procedure under argon gas.

Total creep strain, EWC, and COF were measured as described in Example 29. The hydrogels were equilibrated 40° C. prior to drying for EWC measurement.

Figure 20:
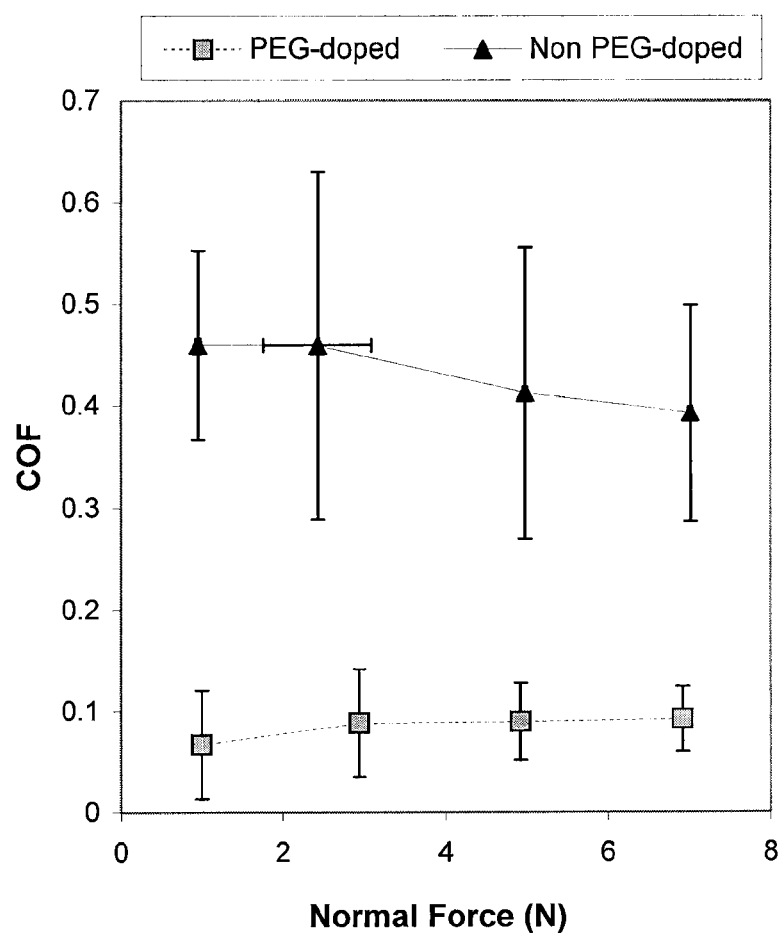
Figure 21:
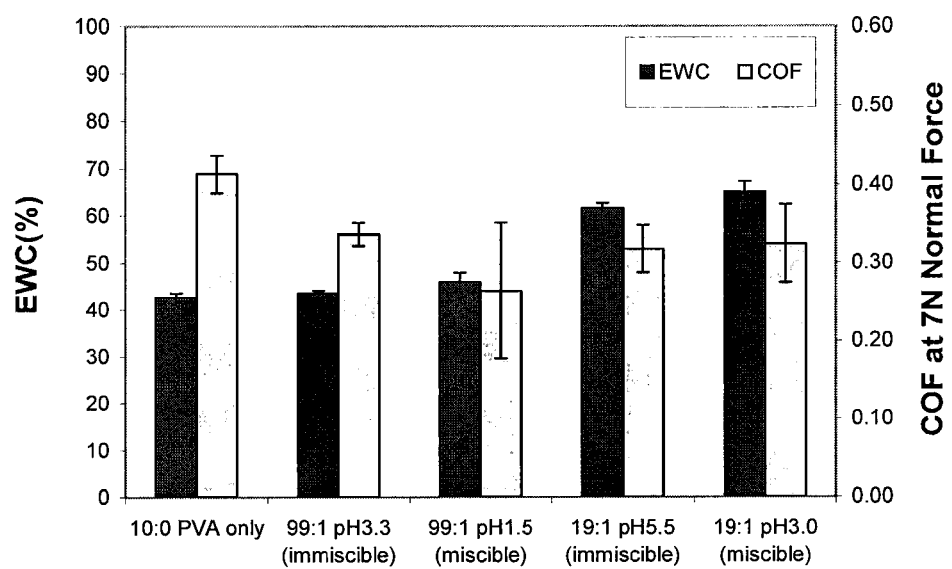
FIG. 21 shows the equilibrium water content (EWC) and coefficient of friction (COF) of the 25% total polymer content PAA-containing PVA gels with various PVA:PAA ratios made by type 1 gel method as described in Examples 31-34. EWC was measured after equilibrating the gels at 40° C. prior to measurement. COF under 7N normal force was taken as the representative COF for each gel. All gels were annealed for 1 hour at 160° C. under argon gas. PVA:PAA ratio is indicated followed by the pH value at which each gelling solution was made. "PVA only" indicates the PVA gels with no PAA. "Miscible" and "immiscible" indicate the miscibility state of each PVA-PAA solution prior to gelling: (1) PVA only, (2) 99:1 PVA:PAA, pH 3.3, (3) 99:1 PVA:PAA, pH 1.5, (4) 19:1 PVA:PAA, pH 5.5, and (5) 19:1 PVA:PAA, pH 3.0.

Results:

The PEG doping step prior to thermal annealing significantly increased EWC (see FIG. 18) in Type 1 gels with 7:3 PVA:PAA ratio. The creep resistance of the PEG doped gels were largely inferior to that of non PEG-doped gel, due to higher EWC. See FIGS. 18 and 19 for the total creep strain and typical creep behaviors of the hydrogels, respectively. However, the presence of PEG during thermal annealing in the PAA-containing Type 1 gel highly improved the surface lubricity as evidenced by the markedly lower COF values of the PEG-doped hydrogels as opposed to that of non PEG-doped hydrogels (see FIG. 20). FIG. 20 shows Coefficient of Friction (COF) of 25% total polymer hydrogels of 7:3 PVA:PAA ratio made with or without the PEG doping step as described in this Example.

Example 31

25% Total Polymer of 19:1 PVA:PAA Ratio with No PEG, pH 3.0, 3 Freeze-Thaw Cycles; PEG-Doped, Vacuum-Dehydration; and Heating

22.5 g of PAA (MW=200,000 g/mol, 25% solid in water, Polysciences) containing 5.625 g of pure PAA is diluted in 317.625 g of deionized water with stirring with no heating to make a 1.654 w/w % PAA solution. The pH value of 1.654% PAA solution is ~3.0 at room temperature. 106.875 g of PVA powder (MW=115,000 g/mol (99.7% hydrolyzed), Scientific Polymer Products) is mixed into the above PAA solution at 90° C. to form a homogenous PVA-PAA solution. The PVA:PAA weight ratio in the final PVA-PAA solution is 19:1 with 25 w/w % total polymer content. The final PVA-PAA solution is a completely clear miscible solution. The PVA-PAA solution is poured into pre-heated glass sheet molds and subjected to three freeze-thaw cycles (16 hour-freezing at −17° C. and 8 hour-thawing at room temperature). Subsequently, the molded gel is immersed in 100% PEG400 followed by vacuum dehydration and annealing at 160° C. under argon in a self-pressurized vessel for one hour. Gel sheets are immersed in deionized (DI) water to remove residual PEG and to reach equilibrated rehydration.

Total creep strain, EWC, and COF can be measured as described in Example 29.

Example 32

25% Total Polymer of 99:1 PVA:PAA Ratio with No PEG, pH 1.5, 3 Freeze-Thaw Cycles; PEG-Doped, Vacuum-Dehydration; and Heating

4.5 g of PAA (MW=200,000 g/mol, 25% solid in water, Polysciences) containing 1.125 g of pure PAA is mixed in 334.125 g of deionized water at room temperature to make a 0.332 wt % PAA solution. The pH of 0.332% PAA solution is initially 3.3 at room temperature and adjusted to pH 1.5 by adding a small amount of hydrochloric acid (HCl) aqueous solution. 111.375 g of PVA powder (MW=115,000 g/mol (99.7% hydrolyzed), Scientific Polymer Products) is mixed into the above PAA solution at 90° C. to form a homogenous PVA-PAA solution. The PVA:PAA weight ratio in the final PVA-PAA solution is 99:1 with 25 w/w % total polymer content. The final PVA-PAA solution is a completely clear miscible solution. The PVA-PAA solution is poured into pre-heated glass sheet molds and subjected to three freeze-thaw cycles (16 hour-freezing at −17° C. and 8 hour-thawing at room temperature). Subsequently, the molded gel is immersed in 100% PEG400 followed by vacuum dehydration and annealing at 160° C. under argon in a self-pressurized vessel for one hour. Gel sheets are immersed in deionized (DI) water to remove residual PEG and to reach equilibrated rehydration.

In making 99:1 PVA:PAA blends, pH adjustment toward acidic condition is critically important in forming a homogenous miscible solution of PVA and PAA prior to gelation through freeze-thawing cycles. When pH of 0.332% PAA solutions is higher than 1.5, for example, pH 2.674 or pH 3.315 before mixing PVA, cloudy and immiscible solution is obtained in 99:1 PVA:PAA ratio mixtures at 90° C.

Total creep strain, EWC, and COF can be measured as described in Example 29.

Example 33

25% Total Polymer of 19:1 PVA:PAA Ratio with No PEG, pH 5.5, 3 Freeze-Thaw Cycles; PEG-Doped, Vacuum-Dehydration; and Heating

22.5 g of PAA (MW=200,000 g/mol, 25% solid in water, Polysciences) containing 5.625 g of pure PAA is diluted in 317.625 g of deionized water with stirring with no heating to make a 1.654 w/w % PAA solution. The pH value of 1.654% PAA solution is 2.998 at room temperature and adjusted to pH 5.5 by adding a small amount of sodium hydroxide (NaOH) aqueous solution. 106.875 g of PVA powder (MW=115,000 g/mol (99.7% hydrolyzed), Scientific Polymer Products) is mixed into the above PAA solution at 90° C. to form a homogenous PVA-PAA solution. The PVA:PAA weight ratio in the final PVA-PAA solution is 19:1 with 25 w/w % total polymer content. The final PVA-PAA solution is homogenous but immiscible with slight opacity. The PVA-PAA solution is poured into pre-heated glass sheet molds and subjected to three freeze-thaw cycles (16 hour-freezing at −17° C. and 8 hour-thawing at room temperature). Subsequently, the molded gel is immersed in 100% PEG400 followed by vacuum dehydration and annealing at 160° C. under argon in a self-pressurized vessel for one hour. Gel sheets are immersed in deionized (DI) water to remove residual PEG and to reach equilibrated rehydration.

Total creep strain, EWC, and COF can be measured as described in Example 29.

Example 34

25% Total Polymer of 99:1 PVA:PAA Ratio with No PEG, pH3.3, Freeze-Thaw Cycles; PEG-Doped, Vacuum-Dehydration; and Heating

4.5 g of PAA (MW=200,000 g/mol, 25% solid in water, Polysciences) containing 1.125 g of pure PAA is mixed in 334.125 g of deionized water at room temperature to make a 0.332 wt % PAA solution. The pH of 0.332% PAA solution is initially 3.315 at room temperature and the PAA solution is used without any pH-adjustment. 111.375 g of PVA powder (MW=115,000 g/mol (99.7% hydrolyzed), Scientific Polymer Products) is mixed into the above PAA solution at 90° C. to form a homogenous PVA-PAA solution.

The final PVA-PAA solution is homogenous but immiscible with slight opacity. The PVA:PAA weight ratio in the final PVA-PAA solution is 99:1 with 25 w/w % total polymer content. The PVA-PAA solution is poured into pre-heated glass sheet molds and subjected to three freeze-thaw cycles (16 hour-freezing at −17° C. and 8 hour-thawing at room temperature). Subsequently, the molded gel is immersed in 100% PEG400 followed by vacuum dehydration and annealing at 160° C. under argon in a self-pressurized vessel for one hour. Gel sheets are immersed in deionized (DI) water to remove residual PEG and to reach equilibrated rehydration.

Total creep strain, EWC, and COF can be measured as described in Example 29.

Example 35

Equilibrium Water Content (EWC) and Coefficient of Friction (COF) Results in 25% Total Polymer of 99:1 or 19:1 PVA:PAA Ratio with No PEG, 3 Freeze-Thaw Cycles; PEG-Immersion; Vacuum-Dehydrated; and Heated

The type 1 PVA gels made with 99:1 or 19:1 PVA:PAA ratio were made as Examples 31-34. Prior to gelling, during PVA-PAA solution preparation, each solution was pH-adjusted to form either a miscible blend or an immiscible blend prior to gelling. Upon gelation, all gels were immersed in PEG, followed by vacuum dehydration and subsequent annealing under argon gas for 1 hour at 160° C.

As compared to the PVA-only gels, EWC remained unchanged with 1% PAA content in the 99:1 PVA:PAA gels. In the 19:1 PVA:PAA ratio gels, EWC increased significantly as opposed to PVA only gels. As low as 1% PAA content showed a detectable decrease in COF values in the PVA gels as opposed to PVA only gels. Miscibility of the gelling solution did not seem to affect the surface lubricity, which implies that the effects of chemical composition of the functional groups can be more substantial than the surface morphology of the PVA gels.

Example 36

Effects of Heating Conditions in 25% Total Polymer of 9:1 PVA:PAA Ratio with No PEG, 3 Freeze-Thaw Cycles; PEG400-Immersed; Vacuum-Dehydrated; and Heated The effects of various heating conditions in the PAA-containing PVA hydrogels with 9:1 PVA:PAA ratio were quantified in terms of EWC, creep resistance, and coefficient of friction. PVA (MW=115,000 g/mol (99.7% hydrolyzed), Scientific Polymer Products) was mixed into an aqueous solution of PAA (MW=200,000 g/mol, Polysciences) at 90° C. to form a homogenous PVA-PAA solution. 25% total polymer of 9:1 PVA:PAA gels were made by subjecting PVA-PAA solution poured into pre-heated glass sheet molds to three freeze-thaw cycles (16 hour-freezing at −17° C. and 8 hour-thawing at room temperature). Subsequently, the gels were immersed in PEG400 (for PEG-doping), followed by vacuum dehydration and heating in a self-pressurized vessel. 1 hour heating at 160° C. under argon gas was used as the reference condition and each parameter such as heating time, temperature, and gas type was varied individually, one at a time, while other parameters were kept unchanged. Four different annealing conditions tested were: (A) 1 hour heating at 160° C. under argon gas, (B) 1 hour heating at 160° C. in air (without argon gas purging), (C) 16 hour heating at 160° C. under argon gas, and (D) 1 hour heating at 200° C. under argon gas. For argon gas atmosphere, the vessel containing the gels was purged with argon gas for five minutes prior to annealing. After annealing, the samples were rehydrated in deionized water until equilibrium hydration was reached. Total creep strain, EWC, and COF were measured as described in Example 29.

Results:

Various heating conditions resulted in changes in the EWC of the gels (see FIG. 21) compared to the EWC value of 80% in the reference annealing condition of 1 hour heating at 160° C. under argon gas. Presence of oxygen in the residual air inside the annealing chamber during annealing slightly reduced EWC by 10% as compared to the inert argon gas environment. Extended annealing time from 1 hour to 16 hour and an increase in heating temperature from 160° C. to 200° C. significantly reduced the EWC to 38% and 45%, respectively.

Figure 22:
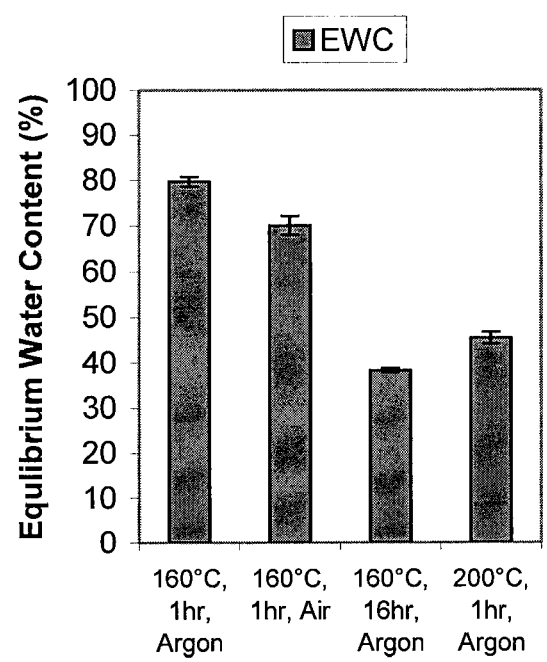
FIG. 22 shows the equilibrium water content of the PAA-containing PVA gels with 9:1 PVA:PAA ratio made by type 1 gel method under various annealing conditions as described in Example 36. EWC was measured after equilibrating the gels at 40° C. prior to measurement. (A) 1 hour heating at 160° C. under argon gas, (B) 1 hour heating at 160° C. in air (without argon gas purging), (C) 16 hour heating at 160° C. under argon gas, and (D) 1 hour heating at 200° C. under argon gas.

Creep response of each gel was also affected by the various annealing conditions (see FIG. 22). Total creep strain (TCS), which is a representative value of creep behavior, was reduced when heated in air instead of argon gas, at the longer annealing duration, or at the higher temperature. The decrease in TCS due to time or temperature changes was more significant than the presence of air during annealing.

Figure 23:
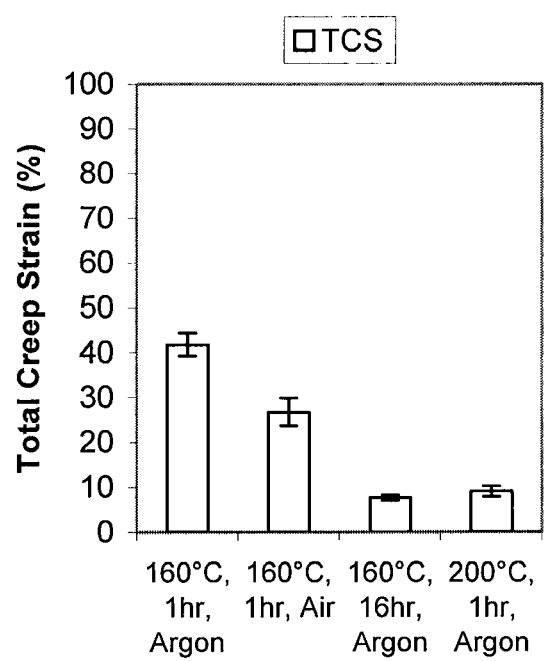
FIG. 23 shows the total creep strain of the PAA-containing PVA gels with 9:1 PVA:PAA ratio made by type 1 gel method under various annealing conditions as described in Example 36. (A) 1 hour heating at 160° C. under argon gas, (B) 1 hour heating at 160° C. in air (without argon gas purging), (C) 16 hour heating at 160° C. under argon gas, and (D) 1 hour heating at 200° C. under argon gas.
Figure 24:
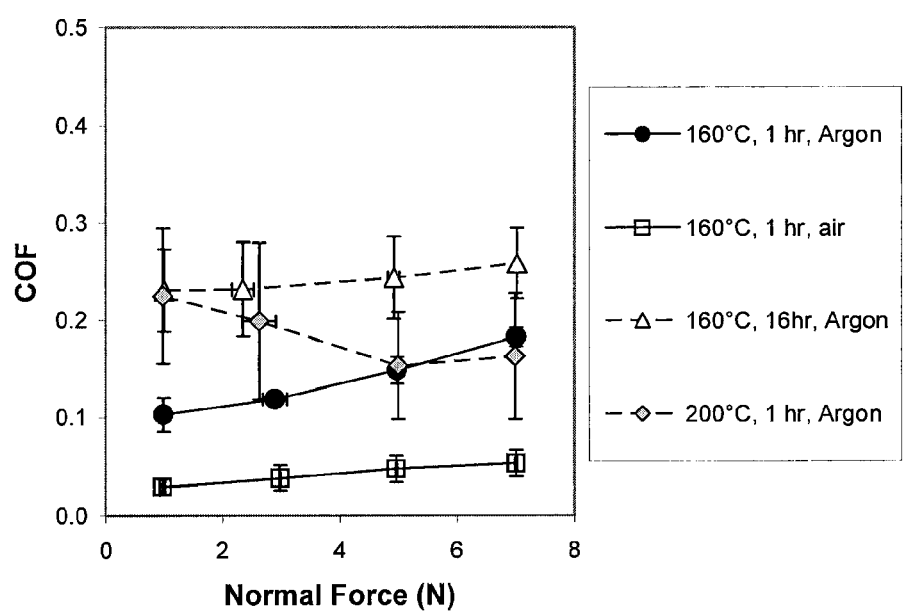
FIG. 24 depicts the coefficient of friction (COF) of the PAA-containing PVA gels with 9:1 PVA:PAA ratio made by type 1 gel method under various annealing conditions as described in Example 36. (A) 1 hour heating at 160° C. under argon gas, (B) 1 hour heating at 160° C. in air (without argon gas purging), (C) 16 hour heating at 160° C. under argon gas, and (D) 1 hour heating at 200° C. under argon gas.
Figure 25:
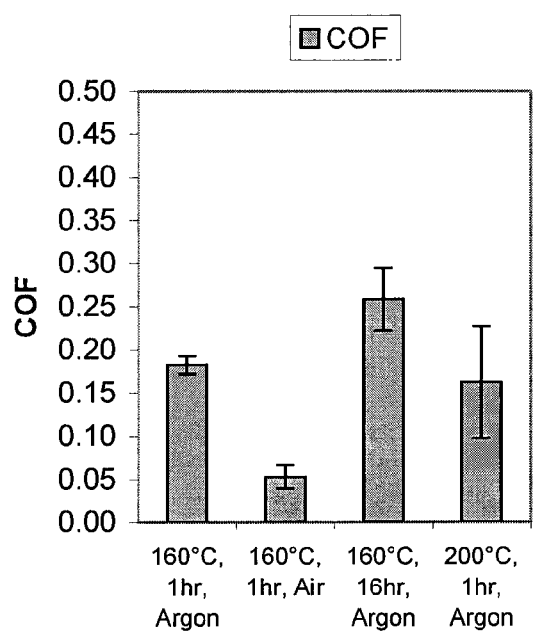
FIG. 25 shows the coefficient of friction (COF) of the PAA-containing PVA gels with 9:1 PVA:PAA ratio made by type 1 gel method under various annealing conditions as described in Example 36. COF under 7N normal force was taken as the representative COF for each gel. (A) 1 hour heating at 160° C. under argon gas, (B) 1 hour heating at 160°

The surface lubricity of the gels was most significantly improved by the presence of air during annealing as evidenced by dramatically low COF values as opposed to the all of the other gels heated under argon gas environment (see FIGS. 23 and 24). Extended heating time and increased heating temperature seemed to adversely affect the surface lubricity of the gels.

Example 37

Effects of the Presence of Air During Annealing in 25% Total Polymer of Various PVA:PAA Ratios with No PEG, 3 Freeze-Thaw Cycles; PEG400-Immersed; Vacuum-Dehydrated; and Heated It was later found that in some of the previous experiments some of the annealing vessels that were purged with argon gas to anneal hydrogels in the absence of air were not completely sealed to maintain inert state during the annealing process. Consequently, some of the type 1 gels described in Examples 29 and 30 were exposed to air during annealing and the COF, EWC, and creep data presented in Examples 29 and 30 were generated from the samples possibly annealed in the presence of residual air instead of solely inert argon gas. In fact, the COF values reported above in Examples 29 and 30 are the average of four samples annealed individually. Some of them showed unusually high variance in COF values. For instance, the COF values under 7N normal force of the 7:3 PVA:PAA gels made by the type 1 gel method were 0.109, 0.128, 0.075, and 0.056 for four samples. Therefore, to ascertain if the presence of air was responsible for this variation, the effects of presence of air during annealing in the PAA-containing PVA hydrogels with various PVA:PAA ratios were quantified in terms of EWC and coefficient of friction in this example. As described below, the presence of air during annealing significantly improved the surface lubricity of PAA-containing PVA gels as opposed to the absence of air during annealing. Thus, the COF values presented in Examples 29 and 30 possibly show lower values than the actual COF values of the gels that were annealed in the absence of air.

PVA (MW=115,000 g/mol (99.7% hydrolyzed), Scientific Polymer Products) was mixed into an aqueous solution of PAA (MW=200,000 g/mol, Polysciences) at 90° C. to form a homogenous PVA-PAA solution. The PVA:PAA weight ratio was varied from "PVA only" (i.e., contains no PAA), 9:1, 8:2 to 7:3 with 25 w/w % total polymer content in each blend. Each PVA-PAA solution was poured into pre-heated glass sheet molds to three freeze-thaw cycles (16 hour-freezing at −17° C. and 8 hour-thawing at room temperature). Subsequently, the gels were immersed in PEG400 for PEG-doping (according to Example 29), followed by vacuum dehydration and annealing at 160° C. in a self-pressurized vessel for one hour. For "argon" group (control), the vessel containing the gels was purged with argon gas for at least 5 minutes prior to annealing. For "air" group, the argon gas purging prior to annealing was omitted and the gels were annealed in a self-pressurizing vessel containing ambient air that were already present prior to placing the gels. After heating, the samples were rehydrated in deionized water until equilibrium hydration was reached. EWC, TCS and COF were measured as described in Example 29.

Results:

Thermal annealing adversely affected the surface lubricity of PVA only gels (containing no PAA) as evidenced by increased COF values after annealing. The increase in COF was more significant when annealing was carried out under argon gas than in air (see FIGS. 26 and 27). Presence of PAA in the PVA gels made by type 1 method completely eliminated such adverse effects on COF due to annealing and further improved the surface lubricity beyond that of non-annealed PVA only gels. Decrease in COF values due to PAA presence in the annealed gel were amplified more significantly for the gels annealed in the presence of air than in inert gas (for example, COF of the 9:1 PVA:PAA ratio gel annealed in the presence of air can be as low as 0.02, as opposed to the COF value of 0.18 in the same composition gel annealed under argon gas in the absence of air), which signifies that residual oxygen from air inside the annealing vessel might cause oxidation and/or other chemical changes on the surface or in the bulk of the gel.

The EWC of PVA gels was increased by the presence of PAA in the gels annealed both under argon gas and in air (FIG. 28). The EWC showed a negligible or slight decrease (less than about 10%) in the gels annealed in the presence of air as opposed to in the absence of air. The total creep strain of the PAA-containing PVA gels showed a slight (less than about 10%) or negligible decrease in the presence of air (i.e., the ambient air containing nitrogen, oxygen, $CO_2$, traces of other gases, water vapor, etc., that were already present in the self-pressurizing vessel prior to placing the gels) during annealing as opposed to in the absence of air (FIG. 29).

In conclusion, the PAA-containing PVA gels that were annealed in the presence of air as opposed to the same PVA:PAA composition gels that were annealed under argon gas in the absence of air showed superior surface lubricity while maintaining the same or slightly improved creep resistance.

It is to be understood that the description, specific examples and data, while indicating exemplary embodiments, are given by way of illustration and are not intended to limit the present invention. Various changes and modifications within the present invention will become apparent to the skilled artisan from the discussion, disclosure and data contained herein, and thus are considered part of the invention.

What is claimed is:

1. A method of making a PVA-hydrogel comprising:
  a) contacting an aqueous solution of poly(vinyl alcohol) (PVA) with an aqueous solution of poly(acrylic acid) (PAA) at a temperature above the room temperature, thereby forming a homogenous PVA-PAA solution wherein the PVA-PAA solution includes no polyethylene glycol (PEG);
  b) pouring the PVA-PAA solution onto a mold followed by cooling down to room temperature, thereby allowing formation of the PVA-hydrogel;
  c) cooling the PVA-hydrogel by freezing at a temperature below 0° C.;
  d) thawing the PVA-hydrogel to a temperature above 0° C.; and
  e) immersing PVA-hydrogel in a PEG solution, thereby allowing diffusion of the PEG into the PVA-hydrogel.

2. The method according to claim 1, wherein the PVA:PAA ratio is about 99.9:0.1 to 5:5.

3. The method according to claim 1, wherein the total polymer content in PVA-PAA solution is about 10% to about 50%.

4. The method according to claim 1, wherein the PVA-PAA solution is poured into a pre-heated mold followed by cooling down to room temperature, thereby allowing formation of the PVA-hydrogel.

5. The method according to claim 1, wherein the PVA-PAA solution is heated to a temperature above room temperature to about 90° C.

6. The method according to claim 1, wherein the PVA-PAA solution is poured into a pre-heated mold followed by freezing below 0° C. and thawing to a temperature above 0° C., thereby allowing formation of the PVA-hydrogel.

7. The method according to claim 1, wherein the PVA-PAA solution is poured into a pre-heated mold followed by freezing below 0° C. and thawing to a temperature above 0° C., thereby allowing formation of the PVA-hydrogel.

8. The method according to claim 1, wherein the PVA-hydrogel is re-hydrated in water or saline.

9. The method according to claim 1, wherein the freeze-thaw step is repeated for at least 2 to 100 cycles.

10. The method according to claim 1, wherein the freeze-thaw step is repeated for at least 2, 3, 4, 5, 6, 7, 8, 9, 10, or more cycles.

11. The method according to claim 1, wherein the PVA-hydrogel is dehydrated to remove part or all of the water content.

12. The method according to claim 1, wherein the PVA-hydrogel is dehydrated by a method comprising the steps of:
  a) contacting the PVA-hydrogel with an organic solvent, wherein the hydrogel comprises a polymer which is not soluble in the solvent, and wherein the solvent is at least partially miscible in water; and
  b) air-drying the hydrogel at room temperature or heat drying the hydrogel.

13. The method according to claim 1, wherein the PVA-hydrogel is dehydrated by a method comprising the steps of:
  a) contacting the PVA-hydrogel with an organic solvent, wherein the hydrogel comprises a polymer which is not soluble in the solvent, and wherein the solvent is at least partially miscible in water; and
  b) subjecting the hydrogel to at least one freeze-thaw cycle and allowing the hydrogel to warm-up room to temperature.

14. The method according to claim 11, wherein the dehydration is carried out by placing the hydrogel in:
  a) a non-solvent, wherein
    i) the non-solvent is PEG, alcohols, acetones, saturated salinated water, vitamin, or carboxylic acid, aqueous solution of a salt of an alkali metal, and
    ii) the non-solvent contains more than one ingredient including water, PEG, vitamin, polymer, ester, proteoglycan, and carboxylic acid, or
  b) in a supercritical fluid.

15. The method according to claim 11, wherein the dehydration is carried out at about 40° C. to above 200° C.

16. The method according to claim 11, wherein the dehydration is carried out in an atmosphere containing 100% air, 100% inert gas, a mixture of one or more inert gases mixed with 0.1% to 99.9% air, or a mixture of one or more inert gases containing 0.1% to 99.9% oxygen.

17. The method according to claim 11, wherein the dehydrated hydrogel is re-hydrated by placing the dehydrated hydrogel:
  i) in water, saline solution, Ringer's solution, salinated water, buffer solution, and the like,
  ii) in a humid chamber, and/or
  iii) at room temperature or at an elevated temperature.

18. The method according to claim 1, wherein the PVA-hydrogel is re-hydrated to reach an equilibrium.

19. The method according to claim 1, wherein the $pH_{mt}$ of a PVA-PAA solution containing 1.654 w/w % aqueous PAA solution and 25% total polymer having a PVA:PAA ratio of 19:1 is between about 3.0 and about 5.5.

20. The method according to claim 1, wherein the PVA-hydrogel comprises one or more hydrophilic polymers selected from the group consisting of: PVA-PAA copolymer, poly(ethylene oxide) (PEO)-PAA copolymer, Poly(methacrylic acid) (PMAA), polyvinylpyrrolidone (PVP), hyaluronic acid (HA), and poly(allylamine hydrochloride) (PAH).

21. The method according to claim 1, wherein the hydrogel comprises water and/or one or more other ingredients, wherein the ingredient is PEG of different molecular weights or a blend of PEGs of different molecular weights.

22. The method of claim 1 further comprising dehydrating the hydrogel.

23. The method of claim 1 further comprising forming a medical implant from the PVA-hydrogel.

* * * * *